United States Patent [19]

West et al.

[11] Patent Number: 4,602,011

[45] Date of Patent: Jul. 22, 1986

[54] ANTIMICROBIAL COMPOSITIONS AND METHODS OF USING SAME

[75] Inventors: Michael H. West; Fritz J. Nagel, both of Memphis, Tenn.

[73] Assignee: Chapman Chemical Company, Memphis, Tenn.

[21] Appl. No.: 419,396

[22] Filed: Sep. 17, 1982

Related U.S. Application Data

[63] Continuation of Ser. No. 175,073, Aug. 4, 1980, abandoned, which is a continuation-in-part of Ser. No. 002,555, Jan. 11, 1979, abandoned, which is a continuation of Ser. No. 842,933, Oct. 17, 1977, abandoned, which is a continuation-in-part of Ser. No. 625,741, Oct. 24, 1975, abandoned, which is a continuation-in-part of Ser. No. 364,018, May 25, 1973, abandoned.

[51] Int. Cl.$^4$ .................... A01N 55/02; A61K 31/555
[52] U.S. Cl. .................................... 514/187; 514/191; 514/576
[58] Field of Search ......................................... 514/187

[56] References Cited

U.S. PATENT DOCUMENTS

| | | | |
|---|---|---|---|
| 2,755,280 | 7/1956 | Feigin et al. | 424/245 X |
| 3,141,821 | 7/1964 | Compeau | 424/347 X |
| 3,223,584 | 12/1965 | Luckenbauch et al. | 424/273 R |

OTHER PUBLICATIONS

Chemical Abstracts, 62:123920, (1965).
Chemical Abstracts, 72:65702m, (1970).
Chemical Abstracts, 52:12437h, (1958).

*Primary Examiner*—Leonard Schenkman
*Attorney, Agent, or Firm*—Fred Philpitt

[57] ABSTRACT

Our invention pertains to various new compositions, methods for using such compositions and products treated with such compositions. Our new compositions include, among other things, certain antimicrobial agents solubilized with certain disubstituted aryl compounds.

19 Claims, No Drawings

ANTIMICROBIAL COMPOSITIONS AND METHODS OF USING SAME

RELATED APPLICATIONS

This application is a continuation of Ser. No. 175,073 filed Aug. 4, 1980 (now abandoned) which is in turn a continuation-in-part of Ser. No. 2,555 filed Jan. 11, 1979 (now abandoned) which in turn is a continuation of Ser. No. 842,933 filed Oct. 17, 1977 (now abandoned) which in turn is a continuation-in-part of Ser. No. 625,741 filed Oct. 24, 1975 (now abandoned) whicn in turn is a continuation-in-part of Ser. No. 364,018 filed May 25, 1973 (now abandoned). The benefits of 35 USC 120 are claimed relative to all of these prior applications.

SECTION 1

One embodiment of our invention pertains to an antimicrobial agent solubilized with a disubstituted aryl compound having a hydrophilic and an oleophilic substituent. In one preferred embodiment the antimicrobial agent is an organometal compound, such as a metal complex of 8-hydroxy quinolinol (oxine), and the disubstituted aryl compound is an alkyl benzene sulfonic acid.

This invention relates to antimicrobial compositions and places particular emphasis on antimicrobial compositions that have low toxicity to plant and animal life. The increasing pressures of government and the awakening concern of the public to environmental protection are greatly restricting the use of time-honored antimicrobials for toxicological reasons. For example, in the case of fungicides which have been widely used in the outdoor environments of agriculture and lumber treatment, many of the known effective fungicides are based upon compounds of toxic metals, such as mercury and lead, and organic compounds such as chlorinated phenols. With increasing population growth, the demands for more and more food production and the increased need for wood and its preservation have caused these classic fungicides to be overworked to the extent that observable adverse effects upon man's environment have been felt.

Vast demands exist for compounds to control microorganisms in fields other than agriculture and wood preservation. These include the treatment of fabrics to prevent mildew and rot; to inhibit and kill bacterial growth; the treatment of surfaces and substrates to obtain antiseptic conditions for medical, industrial, food processing and household purposes; the formulation of ink and paints to prevent mold growth and bacterial decomposition; the prevention and treatment of human and animal diseases; and on through an almost infinite spectrum of applications touching out daily lives.

The disruption of the life cycle of microcellular structures has received considerable study and, while there are still many unproved theories as to their mechanism, a number of generalities may be made. For example, it has been suggested that in probably a majority of instances, the toxic effect of an antimicrobial agent depends upon its gaining access to the interior of the cell. In somewhat lesser instances, the antimicrobial may be an effective agent through the functions it performs outside the cell. In this latter regard, such as in the case of fungi that excrete enzymes to metabolize cellulosic materials around them and absorb the digested materials, it has been proposed that some fungi may be "starved" by chemically disrupting or sequestering the excreted enzymes.

With respect to those antimicrobials that penetrate the semipermeable membranes of the cell, little is known of the nature of their activity once inside the cell. Some researchers believe that they may chelate trace amounts of metals that are necessary to support the life of the microorganism, others have suggested that they bring with them small amounts of metals, such as mercury, silver and copper, that are toxic to the organism, others have suggested that some antimicrobials may oxidize fatty acids and proteins within the cell, and, in the absence of any positive proof of the precise activity within the cell, one expert has suggested that when an effective antimicrobial agent enters the highly complex and delicately balanced chemical system of the microbe, the result is massive disruption of the system, not unlike throwing several cats over a clothesline while their tails are tied together.

In those instances in which the antimicrobial must pass through the wall and enter the microorganism cell to be effective, it was believed to follow that, since practically all microorganisms live in an aqueous environment, it should be a criterion that these antimicrobials be hydrophilic. While this supposition was correct with respect to penetration of the outermost layers of the microorganisms, it was later recognized that hydrophilic materials would be repulsed by the lipoid layers of the cell. It was then theorized that an oleophilic antimicrobial agent should be selected, but, of course, this was not always effective since the oleophilic (hydrophobic) agent could not traverse the outer aqueous barrier of the cellular structure. It is now recognized that this dilemma may be solved by structuring a composite compound in which one portion of it is hydrophilic and another portion of it is oleophilic.

It has also been recognized for a number of years that an oleophilic material, in order to penetrate the walls of a microorganism, must have some degree of steric compatibility with the structure of the cell wall. At least one respected writer, James G. Horsfall, in *Principals of Fungicidal Action (Chronica Botanica Co.* 1956, Library of Congress No. 56-8265), likens the nature of an effective oleophilic group to a shaped charge such as may be used in armor-piercing explosive shells. Horsfall suggests that the oleophilic or fat-soluble groups should more or less match the shape of the fatty groups in the cell's semipermeable membrane as, by so "shaping the charge," it will permit permeation through the critical fatty barrier of the cell. This may be taken to mean, first of all, that the fat-soluble group must have a length that is significant with respect to the thickness of the cell wall. Next, the oleophilic group should not be unduly branched nor contain substituents so large so as to cause steric hindrance to the penetration of the "shaped charge" into and through the cell wall. A simple illustration of an oleophilic "shaped charge" is a straight-chained hydrocarbon having at least about six carbon atoms in the chain.

A classic example of the use of a "shaped charge" to penetrate a semipermeable membrane of a microcell lies in the discovery of hexylresorcinol. Here the inventor found that the germicidal properties of resorcinol, which were known to be only mediocre, could be significantly improved by substituting a straight-chained six-carbon alkyl group on the benzene ring of a resorcinol molecule. The effect was dramatic, at least from the viewpoint of commercial success, as hexylresorcinol a generation or so ago became a household word and was a disinfectant that could be found in many a home medicine cabinet.

To summarize, the prior art recognizes that it is often necessary for an effective antimicrobial agent to pass through the semipermeable membrane of a microcell if it is to be effective in disrupting the microcellular life. It is also known that penetration of the cell may be enhanced by the use of certain oleophilic "shaped charges" that have stereochemical compatibility with the structure of the lipid layer of the cell membrane. It is further known that the ability of the oleophilic "shaped charge" to penetrate a cell wall will be increased if the oleophilic group is associated with a hydrophilic group that will serve as its passport through the outer aqueous barrier layer of the cell. It has also been recognized that many surfactants, due to their combined hydrophilic and oleophilic properties, are sometimes effective as antimicrobials to varying degrees and in certain environments.

An objective of our invention is to provide an antimicrobial composition that is effective in controlling a wide spectrum of microorganisms and which has relatively low toxicity toward animal and plant life. These and other objects of this invention are accomplished by formulating a solution comprised of an active antimicrobial agent and a disubstituted aryl compound in which the first substituent is an oleophilic group adapted to penetrate the lipid layers of microcells and the second substituent is a hydrophilic group. While it is believed necessary to form an initial solution of the antimicrobial agent with the disubstituted aryl compound, the antimicrobial agent may, when diluted for use, begin to precipitate from solution. This preceipitation from solution may and usually will become complete after the composition has been applied to a substrate.

DETAILED DESCRIPTION

The Oleophilic Substituent

The oleophilic substituent of the composition of this invention should have a degree of stereochemical compatibility with the structure of the semipermeable membrane of the cell of a microorganism. As recognized in the prior art, a common structure meeting this criterion is an assentially unsubstituted straight-chained hydrocarbon having a length that is significant with respect to the thickness of a cell wall. This generally requires, as a minimum, an alkyl chain with about six carbon atoms in it. The alkyl chain, on the other hand, should not be too long since the mobility of an alkyl chain increases with increasing chain length and alkyl chains will begin to coil if they are too long. When the coiling becomes significant, it can cause steric hindrance and make permeation of the cell wall difficult. While the maximum length of the alkyl chain can only be determined with respect to a given environment and a specific cell structure, it is believed to be a fair generalization to suggest that an alkyl chain much longer than 18 carbon atoms and, more especially, one longer than 24 carbon atoms, will lose its effectiveness in penetrating the cell wall.

The preferred alkyl groups of this invention are not excessively branched or substituted in the sense that they will result in steric hindrance. Nonetheless, some substitutes along the hydrocarbon chain, such as chlorine, may improve the oleophilic properties of the "shaped charge" and may be used to advantage. It has been observed that judicious chlorine substitution may permit the use of shorter alkyl chains.

Throughout the specification and examples, the alkyl aryl sulfonic acids are referred to in language that might suggest pure substances. For instance, dodecyl benzene sulfonic acid (DDBSA) is benzene sulfonic acid with a 12-carbon alkyl chain attached to the benzene ring, but the DDBSA actually employed in the examples is a typical sulfonic acid commercially available comprised of a complex alkyl benzene which is a reaction product of benzene with the tetramer of propylene. Such alkyl benzenes are mixtures wherein the average alkyl chain length determines the name given to the product. This so-called DDBSA, with a typical M.W. of 237 as specified by one manufacturer, may contain side chain lengths from about $C_2$ to $C_{20}$, more than one side chain, and side chains in varying positions on the aryl ring. A usual specification for DDBSA will call for a minimum of 85% $C_{10}$ through $C_{12}$ alkyl side chain lengths.

Similarly, while $C_6$ to $C_{24}$ side chain lengths are claimed in this invention, this actually refers to the approximate average length, such averages being obtainable by use of alkyl aryl sulfo compounds as received from a producer, or by mixtures of two or more compounds, each with a different average alkyl side chain length.

Pure long-side-chain alkyl aryl sulfonic acids will function in this invention, but have no practical value because they are not available commercially and because of the extremely high cost.

To determine differences in antifungal efficacy and physical characteristics of compositions of the invention prepared with Cu-8-Q and a range of alkyl aryl sulfonic acids, carbon chain lengths of the alkyl group attached to the aryl group varying from $C_8$ to $C_{15}$ were tested. These included $C_8$ (octyl benzene sulfonic acid), $C_{10}$ (decyl benzene sulfonic acid), $C_{12}$ (dodecyl benzene sulfonic acid—DDBSA), $C_{13}$ (tridecyl benzene sulfonic acid) and $C_{15}$ (pentadecyl benzene sulfonic acid). Determination of antifungal efficiency was made by the test method of Example 1 set forth below.

It was determined that optimum antifungal efficacy was obtained in the $C_{10}$ to $C_{13}$ range, with $C_{12}$ (DDBSA) being the best, by a small margin of little practical consequence for most applications, all-around solubilization of antimicrobial agents such as metal complexes of oxine. A small but significant reduction in efficacy resulted from the use of $C_8$ and $C_{15}$, although use of both are within the scope of this invention.

It also was determined that optimum handling characteristics—concentrate and use-dilutions stability, ease of dilution with water, low temperature concentrate viscosity, maximum amount of antimicrobial agents incorporatable in the concentrate, etc.—of compositions of the invention were obtained generally with $C_{12}$, although differences with $C_{10}$ and $C_{13}$ were small to insignificant in most use instances.

$C_{15}$, because of its greater lipophilic character, exhibits diminished water solubility, a matter of practical consequence since water is the preferred use diluent for most end uses of the compositions of this invention. The increased lipophilic character imported to the compositions of the $C_{15}$ alkyl chain exerted no adverse effect upon general organic solvent solubility of the invention compositions and is of benefit in those end uses where, for a variety of reasons, a non-water carrier is desired.

Lastly, it is within the scope of the invention to employ mixtures of sulfonic acids including alkyl side chains of $C_0$ and $C_1$ with $C_8$ to $C_{24}$.

No rigid definition can be given as to the length, composition and configuration of the oleophilic group and these parameters necessarily must be adjusted for the microbial genus and species that are to be controlled. It is believed, however, that given the insight provided by this specification, it will be within the skill of a worker of ordinary skill in the art to select, with minimum effort, an oleophilic substituent that will permeate the lipoid layer of a microcellular organism in the practice of this invention.

The Hydrophilic Substituent

The hydrophilic substituent of the aryl compound should be ionizable and contribute to the solubilization of the antimicrobial agent. Two of the most effective and chemically accessable such substituents that will accomplish this purpose are the sulfo and the hydroxyl radicals.

The Aryl Compound

A preferred aryl compound is benzene which is believed to be most effective and, perhaps to a lesser extent, naphthalene. Aryl compounds comprised of more than two ring structures may lose their effectiveness for several reasons, among them being the fact that their size becomes large as compared with the oleophilic substituent and will tend sterically to hinder the oleophilic substituent in penetrating the wall of the microorganism. While not essential in the practice of this invention, tertiary substituents of the aryl group may sometimes prove desirable, particularly if they are capable of withdrawing electrons to improve the solubilization of the antimicrobial agent. Substituents which may function in this manner are, for example, $-NO_2$, $-CN$ and $-CHO$. Electron-withdrawing substituents should be used sparingly and with discretion to avoid overloading of the ring structure of the aryl compound.

The Antimicrobial Agent

As set forth above, the antimicrobial agent must be able to form a solution with the substituted aryl compound, at least in the initial formation of a concentrate which may later be diluted prior to use.

One particular advantage of this invention lies in the fact that antimicrobial agents that have known low toxicity toward plant and animal life may be made more effective by solubilizing them in accordance with this invention, thus greatly increasing their utility. Of these, for example, the metal complexes (chelates) of 8-hydroxy quinolinol (oxine), and especially copper-8-quinolinolate (Cu-8-Q), are quite prominent due to their comparatively low toxicity toward human, animal and plant life.

Another unexpected result that accrues through the practice of this invention lies in the fact that when an aryl-alkyl sulfonic acid is solubilized with a metal-8-Q, the solution is far less irritating to body tissue and skin than is the aryl-alkyl sulfonic acid by itself. For example, in tolerance tests conducted on sensitive areas of the human skin, solutions of DDBSA and Cu-8-Q diluted 1:200 with water were not only found to be less irritating than DDBSA at the same dilution, but also less irritating than cleansing agents generally accepted as being "mild" such as Ivory Soap.

It has been discovered that not only are antimicrobial agents such as metal complexes of oxine readily soluble in the substituted aryl compounds of this invention, but also their effectiveness as an antimicrobial is materially increased over formulations of these antimicrobial agents known to the prior art. As will be demonstrated in the following examples, when Cu-8-Q, for example, is solubilized by dodecyl benzene sulfonic acid (a substituted aryl compound of this invention), its effectiveness in controlling the growth of microorganisms improves dramatically.

In addition to Cu-8-Q, other metal complexes of oxine are known to be effective antimicrobials. Of these, mercury is generally regarded as being more effective than copper, and the following is a listing taken from literature references of the relative effectiveness of several metal quinolinolates in descending order of activity: mercury, copper, cadmium, nickel, lead, cobalt, zinc, iron and calcium. Aluminum and tin are also useful.

Antimicrobials other than metal oxines may be solubilized in the alkyl aryl sulfonic acids of the invention, both alone and in the presence of the metal oxines. For a variety of specialized requirements, such other antimicrobials have significant utility, not only for antimicrobial properties, but also because of the considerable handling and application advantages of true solution formulations inthose instances where the antimicrobial normally is not water-soluble and must be applied either as a dust or as a particulate suspension in water. Among the antimicrobials which are useful are these classes:

1. Oxine and derivatives thereof.
2. Chlorophenols such as tri-, tetra- and pentachlorophenol.
3. Anilides such as 2,5-dimethyl-3-furylanilide.
4. Benzimidazoles such as 2-(methoxy-carbamoyl)-benzimidazole.
5. Nitrophenols such as dinitrophenol.
6. Nitrocresols such as dinitrocresol.
7. Crotonates such as 2,4-dinitro-6-(2-octyl)phenyl crotonate.
8. Organotins such as triphenyltin acetate and tributyl tinoxide.
9. Antibiotics such as streptomycin and griseofulvin.
10. Organic acids such as acetic, sorbic, salicylic, benzoic, dehydroacetic and undecylenic acids.
11. Oxathiius such as 5,6-dihydro-2-methyl-1,4-oxathiin-3-carboxanilide.
12. Sulfones such as diiodomethyl-p-tolyl sulfone.
13. Iodine, compounds thereof, and iodofors.
14. Aliphatic alcohols from $C_1$ to $C_{18}$ chain length.
15. Alkyl, benzyl and phenyl alcohols.
16. Hydroxyl diphenyl oxide and sulfide isomers.
17. Carbanilides such as trichlorocarbanilide.
18. Bis phenols such as hexachlorophene.
19. Phenyl mercurials such as phenyl mercuric acetate and nitrate.
20. Complex organic mercurials such as thimersol and nitromersol.
21. Aldehydes such as formaldehyde and glutaraldehyde.
22. Aniline derivatives such as 2,6-dichloro-4-nitroaniline.
23. Diphenyl ethers such as 2,4,4'-trichloro-2'-hydroxyl diphenyl ether.
24. Miscellaneous types including silver oxine; chlorhexidine and water-soluble acetate and gluconate derivatives thereof; imidazolidinyl urea; hexylresorcinol;

3(2-(3,5-dimethyl-2-oxycyclohexyl)-2-hydroethyl)-glutarimide; benzoaminobenzene sulfonate; 3,ethylidene-L-azetidine-2-carboxylic acid; 4,6-dichloro-N-(2-chlorophenyl)-1,3,5-triazin-2-amine; N,N'-(piperazinediyl bis(2,2,2-trichloroethylidene))bis(formamide); salicyanilide-2-hydroxy-N-phenylbenzimide; hexachlorobenzene; boric acid; 5,6,7,8-tetrachloroquinoxaline; 1-hydroxypyridine; 2-n-octyl-4-isothiazolin-3-one; 1,2-benzisothiazolin-3-one; p-chlorophenyl-3-iodopropargyl formol; dimethylol dimethylhydantoin-1,3-bis(hydroxymethyl)-5,5-dimethyl-2,4-imidazolidine-dione; 7-(cis-3-chloro-2-propenyl-1,3,5-triazo-7-azoniatricyclo[3.3.1.1.$^{3,7}$]decane.

In the examples that follow, two methods were used for incorporating a metal-oxine complex into the composition of the invention: (a) the addition of the complex itself, and (b) the in situ formation of the complex in the compositions. The latter often is preferable for economic and versatility reasons.

For in situ formation, an appropriate metal compound is used for reaction with oxine. In the case of Cu-8-Q, for example, copper hydrate, copper sulfate, copper acetate, copper chloride and copper naphthenate are among the suitable sources of copper. The actual choice depends on the economics (some copper compounds are cheaper copper sources than others), nature of by-product (copper hydrate and oxine form water; copper acetate plus oxine form acetic acid, etc.); ease of reaction (some copper compounds release copper to form the copper-oxine chelate easily; others do so more slowly and only under more severe reaction conditions). All are within the scope of this invention. This is true also of in situ formation of metal-oxine chelates other than copper.

Generally, oxine itself is the preferred raw material for preparation of the metal chelate inasmuch as oxine itself is effective, more readily available and lower in cost than substituted chelating oxines. The latter, however, are within the scope of this invention and have utility in certain medical applications where more costly substituted oxines is not such a significant limitation.

Generally, the full metal chelate of oxine is the preferred form, but two variants of full chelates are within the scope of this invention: (a) half-chelates in the case of metals with a valency of two or more, such as copper, and (b) a stoichiometric excess or deficiency of metal required to produce the full chelate.

A polar diluent is used with the mixture of DDBSA and Cu-8-Q which not only serves as a viscosity-reducing agent, but also permits ionization of the alkyl benzene sulfonic acid to achieve complete solubility of the Cu-8-Q. It has been found that complete solubilization is effected through the use of a highly polar organic solvent which, for purposes of economy in diluting the solution for end use applications, is preferably water-miscible. A partial list of suitable diluents for use in the present invention is given below:

Methanol
Ethanol
Isopropanol
n-Butanol
Dimethylformamide
N-methyl-2-pyrrolidone
Ethylene glycol
Propylene glycol
Water Broadly speaking, for every part by weight of the metal-8-quinolinolate, it is preferred to include from 5 to 50 parts by weight DDBSA and 1 to 50 parts by weight of the polar diluent. The most preferred composition according to the present invention contains from 'to 10 parts by weight of Cu-8-Q, 25 to 83 parts by weight of the alkyl benzene sulfonic acid, and 15 to 35 parts by weight of the diluent per 100 parts by weight of the concentrate. One specific composition produced according to the present invention contains about 5 parts by weight of Cu-8-Q, about 64 parts by weight of DDBSA, and about 31 parts by weight of methanol. Additionally, it has been found useful to add minor amounts, e.g., 5% by weight, of ethylene glycol to improve shelf life.

The concentrates prepared as above are diluted with a carrier, preferably water, prior to use, and essentially may be diluted to any degree. Other carriers may be used, including xylene, isopropanol, ethylene glycol and naphtha. The diluted solutions can be applied by a known technique, such as brushing, spraying, dipping or wiping.

EXAMPLES

Examples 1-22

In the examples that follow, the effectiveness of the various formulations was determined by treating freshly cut pine boards by dip immersion for 10 seconds in the formulation to be tested. The boards, along with an untreated control, were placed in a chamber for the period of time indicated and maintained at a temperature of about 80° F. and a humidity of about 70%.

At the end of the test period, the boards were removed from the chamber and rated for effectiveness in terms of percentage of total surface area covered by fungal stain and mold growth. Accordingly, the lower the percentage, the higher the effectiveness of the test formulation.

Unless otherwise indicated, the tabularized formulations were concentrates that were diluted with a carrier, as indicated, prior to application to the substrate. All parts given in these and other examples are parts by weight, unless otherwise noted.

| Example | Cu—8-Q Amount | Solubilizing Agent (amount) | Diluent (amount) | % Fungal Growth (42 days) |
|---|---|---|---|---|
| 1 | 10 | DDBSA (50) | Methanol (40) | 29 |
| 2 | 10 | 98% H$_2$SO$_4$ (20) | Water (70) | 53 |
| 3 | 10 | Maleic acid (50) | Water (40) | 58 |
| 4 | | Untreated control boards | | 74–90 |
| 5 | 5 | DDBSA (64) | Methanol (31) | 17 |
| 6 | 5 | p-toluene sulfonic acid (64) | Methanol (31) | 52 |
| 7 | 5 | 1-naphthalene sulfonic acid (64) | Methanol (31) | 74 |
| 8 | 5 | Benzene sulfonic acid (64) | Methanol (31) | 92 |
| 9 | 5 | Methane sulfonic acid (64) | Methanol (31) | 62 |
| 10 | | Untreated control boards | | 90 |

(Use dilution in above examples 400:1 with water carrier.)

In each of the above examples, the Cu-8-Q formed a true solution with the solublizing agent, both as a concentrate and when diluted for use with the water carrier. These examples show that solubilization of the antimicrobial agent is not sufficient to obtain the desired results of this invention, but that the solubilizing agent must be selected in accordance with the criteria discussed above, such as is the case with DDBSA which is a disubstituted aryl compound having the defined oleophilic and hydrophilic substituents.

In the following examples, the very real improved antifungal activity achieved in the practice of this invention is demonstrated. Cu-8-Q and DDBSA were tested separately and combined to determine efficacy in control of sapstain and mold on fresh cut green lumber. Also compared is Nylate 10 (Seymour Chemical Company), a commercially available, solubilized Cu-8-Q and water emulsifiable concentrate (10% Cu-8-Q). For use, Nylate 10 was diluted 1:200 with water.

| Example | Composition | % Fungal Growth (28 days) |
|---|---|---|
| 11 | Nylate 10 aqueous emulsion, 0.05% Cu—8-Q | 72 |
| 12 | 0.025% Cu—8-Q aqueous suspension (prepared by ball milling) | 89 |
| 13 | 0.35% DDBSA aqueous solution | 49 |
| 14 | Prepared by mixing the composition of Examples 12 and 13 to form a solution comprised of 0.025% Cu—8-Q and 0.35% DDBSA | 6 |

The performance of the composition of the invention (Example 14) is much superior to that of Cu-8-Q or DDBSA alone and to that of a conventional solubilized Cu-8-Q/water emulsion.

In order to demonstrate the effectiveness of this invention as an antifungal, sapstain and mold control, comparisons were made with two standard, widely used antifungal compositions.

| Example | Composition | | % Fungal Growth (28 days) | |
|---|---|---|---|---|
| | | | Test #1 | Test #2 |
| 15 | Sodium tetrachlorophenate | 16.40% | 20 | 7 |
| | Other sodium chlorophenates | 4.43% | | |
| | Phenyl mercuric lactate | 0.40% | | |
| | Inerts | 78.77% | | |
| | (Use dilution - 1:100 in water) | | | |
| 16 | Sodium pentachlorophenate | 31.6% | 20 | 0 |
| | Other sodium chlorophenols | 4.4% | | |
| | Borax (sodium tetraborate 10 H$_2$O) | 57.0% | | |
| | Inerts | 7.0% | | |
| | (Use dilution - 10 pounds per 100 gallons of water) | | | |
| 17 | Cu—8-A | 10.0% | 17 | 0 |
| | DDBSA | 50.0% | | |
| | Methanol | 40.0% | | |
| | (Use dilution - 1:200 in water carrier) | | | |

To demonstrate the antifungal properties of various metal-oxine chelates, compositions were prepared using 6 parts by weight of the indicated metal-oxine plus 64 parts DDBSA plus 31 parts methanol. These compositions were diluted 1:200 with a water carrier for use.

| Example | Metal-Oxide | % Fungal Growth (28 days) |
|---|---|---|
| 18 | Copper | 17 |
| 19 | Tin | 20 |
| 20 | Aluminum | 28 |

-continued

| Example | Metal-Oxide | % Fungal Growth (28 days) |
|---|---|---|
| 21 | Nickel | 39 |
| 22 | Zinc | 46 |

The foregoing metal-oxines (metal-8-quinolinolates) also may be prepared in situ in the compositions by reacting oxine with any of a number of appropriate metal compounds. Although the copper chelate of oxine generally is the most effective and versatile for a broad range of end uses, other metal-oxine chelates have utility.

Example 23

The following DDBSA/Cu-8-Q solution was prepared in accordance with previously stated techniques. (In this instance, Cu-8-Q was formed in situ from copper hydrate and oxine, also known as 8-hydroxy quinoline.)

| | |
|---|---|
| Copper hydrate | 1.70 |
| Oxine | 4.44 |
| DDBSA | 64.81 |
| Methanol | 15.05 |
| Isopropanol | 14.00 |

This composition was diluted with a water carrier, as tabularized below, and tested in comparison with a sodium tetrachlorophenate (23%) liquid concentrate, also diluted in a water carrier, against organisms on three species of green lumber—Douglas fir, Amabilis fir and Ponderosa pine. The organisms were:

| | |
|---|---|
| *Cephaloascus fragans* | a brown mold that infects certain wood species |
| *Trichoderma virgatum* | a common cold |
| Mixed spores | a combination of two molds (Penicillium sp. and *Aspergillis niger*) and a fungus (*Ceratocystis pilifera* that causes blue stain in wood. |

The freshly cut wood samples were dip treated (15-second immersion) with the test fungicides and then innoculated with spore suspensions of the above-described fungi. The test boards plus untreated control boards were then placed in a warm, humid chamber for four weeks. The results are set forth in the table below in which:

| | Use Dilution | C. fragans | | | T. virgatum | | | Mixed spores | | |
|---|---|---|---|---|---|---|---|---|---|---|
| | | A | B | C | A | B | C | A | B | C |
| Tetrachlorophenol composition | 1:100 | 4 | 4 | 4 | 0 | 0 | 3 | 3 | 4 | 4 |
| DDBSA/Cu—8-Q solution | 1:240 | 2 | 0 | 1 | 3 | 0 | 4 | 4 | 3 | 4 |
| Tetrachlorophenol composition | 1:50 | 2 | 0 | 4 | 0 | 0 | 1 | 3 | 2 | 4 |
| DDBSA/Cu—8-Q solution | 1:120 | 0 | 0 | 1 | 3 | 0 | 1 | 2 | 2 | 2 |
| Tetrachlorophenol composition | 1:25 | 2 | 2 | 3 | 0 | 0 | 1 | 0 | 0 | 3 |
| DDBSA/Cu—8-Q solution | 1:60 | 0 | 0 | 0 | 1 | 0 | 0 | 0 | 0 | 0 |
| Tetrachlorophenol composition | 1:12.5 | 0 | 1 | 0 | 0 | 0 | 0 | 0 | 0 | 2 |
| DDBSA/Cu—8-Q | 1:30 | 0 | 0 | 0* | 0 | 0 | 0 | 0 | 0 | 0 |

-continued

| | Use Dilu-tion | C. fragans | | | T. virgatum | | | Mixed spores | | |
|---|---|---|---|---|---|---|---|---|---|---|
| | | A | B | C | A | B | C | A | B | C |
| solution | | | | | | | | | | |
| Control (no treatment) | | 4 | 4 | 4 | 3 | 4 | 4 | 4 | 4 | 4 |

A = Douglas fir
B = Amabilis fir
C = Ponderosa pine
0 = no growth
1 = no growth for 2 weeks
2 = medium growth
3 = heavy growth in 4 weeks
4 = heavy growth in 2 weeks

Example 24

To further illustrate the antifungal properties of compositions of the invention, the formulation below was prepared and tested as a preservative against microbiological deterioration of 10 oz. cotton duck cloth and compared with untreated cotton duck as a control and with Cunilate 2174, a commercially available concentrate containing 10% Cu-8-Q which is made soluble in petroleum hydrocarbon solvents via use of nickel acetate and 2-ethyl hexoic acid. The previously described Nylate 10 also was tested.

| Oxine | 4.1 parts by weight |
|---|---|
| Copper hydrate | 1.4 parts by weight |
| DDBSA | 64.0 parts by weight |
| Propylene glycol methyl ether | 30.5 parts by weight |

This composition was use-diluted 1:24 with a water carrier; the Cunilate 2174 was diluted 1:19 and 1:9 with mineral spirits for use; the Nylate 10 was diluted 1:19 and 1:9 with water. The cotton samples were dipped to refusal in the test compositions, air-dried and buried at 75° F. for 29 days in sheep manure moistened with water. Microorganism attack on the cotton cloth in this test medium is both rapid and severe as can be noted from the essentially total destruction of the untreated control cloth sample. The results of this test are tabulated as follows:

| Composition (dilution) | Weight of Cu—8-Q in Cloth | Estimated Strength Loss* |
|---|---|---|
| Untreated control | 0 | 100% |
| Cunilate 2174 (1:19) | 0.41 gram | 50% |
| Cunilate 2174 (1:9) | 0.84 gram | 25% |
| Nylate 10 (1:19) | 0.61 gram | 50% |
| Nylate 10 (1:9) | 1.21 gram | 0% |
| DDBSA/Cu—8-Q (1:24) | 0.18 gram | 0% |

*As measured by tear strength reduction:
100% = total loss of strength
50% = moderately difficult to tear by hand
25% = difficult to tear by hand
0% = impossible to tear by hand The superiority of the formulation of the invention over other Cu-8-Q compositions is clearly evident.

Example 25

The following composition was tested for minimum fungicidal concentration and compared to two well known antifungal chemicals—pentachlorophenol and 2,3,5 trichloro-4-propyl-sulfonyl pyridine—and DDBSA.

| Oxine | 8.2 parts by weight |
|---|---|
| Copper hydrate | 2.8 parts by weight |
| DDBSA | 59.0 parts by weight |
| Propylene glycol methyl ether | 30.0 parts by weight |

All of the test composition concentrations to be tested were incorporated in the fungal growth media (agar) in accordance with standard microbiological practices. Agar plugs containing the test fungicides then were inoculated with a sporulating culture and inoculated at the temperatures and times specified by The American Type Culture Collection (ATCC) recommendations. The plugs were then scored for absence or presence of organism growth. The results are shown in the following table. Minimum fungicidal concentrations were determined against a broad spectrum of fungi that are detrimental to man, foodstuffs and materials and which can result in metabolite formations (mycotoxins) of extreme toxicity to man and animals.

In the table below, Composition A is that of this Example 25 and the active ingredient is Cu-8-Q; Composition B is DDBSA; Composition C is pentachlorophenol; and Composition D is 2,3,5-trichloro-4-propyl-sulfonyl pyridine. Where no concentration is listed, no data is available. The stated value of "1" means 1 or fewer ppm.

| | Minimum Fungicidal Concentration (ppm of active ingredient) | | | |
|---|---|---|---|---|
| | A | B | C | D |
| Aspergillis niger (ATCC 9642) | 1 | 10,000 | 1-3 | — |
| Aspergillis terreus (ATCC 10609) | 1 | 100 | — | 36 |
| Aspergillis flavus (ATCC 11655) | 1 | 1,000 | 22-54 | — |
| Alternaria alternata (ATCC 13963) | 1 | — | — | — |
| Aureobasidium pullulans (ATCC 16624) | 1 | 100 | — | — |
| Lenzites trabea (ATCC 11539) | 1 | 100 | 1-3 | — |
| Polyporus tulipiferae (ATCC 11245) | 1 | 100 | 1-3 | — |
| Penicillium brevi compactum (ATCC 16024) | 1 | 100 | — | — |
| Rhizopus stolonifer (ATCC 24794) | 1 | 100 | 1-3 | — |
| Trichoderma viride (ATCC 8678) | 10 | 100 | — | — |
| Trichoderma sp. (ATCC 12668) | 1 | 100 | — | — |
| Candida albicans (ATCC 10259) | 1 | 1,000 | — | 3 |

These results illustrate the high efficacy of the composition of this invention and confirm the fact that an antifungal composition prepared from a Cu-8-Q/DDBSA solution is much superior to DDBSA alone. The results also indicate the favorable relative efficacy of the test composition compared to the two commercially available fungicides of recognized high performance.

Example 26

Test compositions were evaluated as wood preservatives via a standard soil block culture procedure (ASTM D4131-61) wherein the wood blocks were water-leached in accordance with standard technique prior to exposure to the test fungus. The test fungi were those specified for wood decay evaluation by the American Wood Preservers' Association (AWPA)—namely, *Lenzites trabea* (Madison 617, ATCC 11539) which is a standard test fungus for above-ground wood exposure, and *Poria monticola* (Madison 698, ATCC 11538) which is the standard copper-tolerant fungus for ground contact wood use.

In the table below, the results are expressed as percentage weight loss of the wood test blocks from decay fungi attack.

Composition A is comprised of:

| | |
|---|---|
| Oxine | 4.42 parts by weight |
| Copper hydrate | 1.51 parts by weight |
| DDBSA | 64.07 parts by weight |
| Methanol | 30.00 parts by weight |

The composition was diluted 1:110 in a water carrier for impregnation of the *L. trabea* test blocks and 1:55 for test against *P. monticola*.

Composition B was the same as Composition A except that it was diluted 1:55 with toluene carrier for block impregnation for test against both test fungi.

Composition C was the same as the DDBSA/Cu-8-Q solution of Example 25 diluted with a water carrier 1:220 for test against *L. trabea* and 1:55 against *P. monticola*.

Cunilate 2174 was diluted 1:110 with a toluene carrier.

The abbreviation "pcf" means pounds of Cu-8-Q per cubic foot of wood.

| | Lenzites trabea | | Poria monticola | |
|---|---|---|---|---|
| Composition | Retention (pcf) | Weight Loss (%) | Retention (pcf) | Weight Loss (%) |
| A | 0.021 | 0.3 | 0.040 | 1.3 |
| B | 0.025 | 5.0 | 0.029 | 11.3 |
| C | 0.018 | 2.0 | 0.036 | 8.1 |
| Cunilate 2174 | 0.024 | 13.6 | 0.026 | 43.4 |
| Untreated control | 0 | 45.3 | 0 | 55.1 |

These results demonstrate the efficacy of the compositions of the invention in both a water and an organic solvent (toluene) carrier. Also illustrated is the greatly improved efficacy over Cunilate 2174, especially for wood in ground contact service. The wood protection results with Compositions A, B and C compare favorably with those of pentachlorophenol (PCP), tested simultaneously, wherein PCP, a world standard for wood preservation, exhibited 1.4% weight loss at 0.30 pcf retention against *L. trabea* and 3.1% weight loss at 0.27 pcf retention in the wood against *P. monticola*.

Employing AWPA Test Method M12-72 (revised 1973) for testing wood block resistance to termite (*Reticulitermes flavipes*) attack, it was determined that no attack occurred at retentions of Composition A adequate to protect the wood from decay.

Example 27

The purpose of this test was to determine antifungal efficacy of DDBSA/Cu-8-Q solutions and to compare their efficacy to that of a world standard, sodium pentachlorophenate, and a mixture of two well-known agricultural fungicides, Topsin M (a thiophenate) and Nabam (a thiocarbomate). The test method is designated as a proposal for the Finnish NWPC Standard No. 1.4.1.3/1974. The test substrate was fresh cut, green pine wood. The test fungi were:

Blue stain fungi—mixture of
  Ceratocystis pilifera Z11
  Schlerophoma entoxylina Z17
  Pullularia pullulans U2
Mold fungi—mixture of
  Paecilomyces varioti X15
  Cladosporium sphaerospermum R7
  Aspergillis amstelodami X19

In the table below, Composition A is the formulation of Example 5 diluted 1:200 with a water carrier.

Composition B is the formulation of Example 5 diluted 1:100 with a water carrier.

Composition C is a 1.5% concentration of sodium pentachlorophenate in water.

Composition D is a 0.4% concentration in water of a 47:53 weight ratio of Topsin M:Nabam.

E refers to untreated control pine boards.

The rating index is:

| | Test Composition | | | | |
|---|---|---|---|---|---|
| | A | B | C | D | E |
| Blue stain fungi growth | 0.8 | 0.3 | 0.5 | 2.5 | 3.9 |
| Mold fungi growth | 0.5 | 0 | 0.3 | 1.3 | 3.6 |

0 = no visible growth
1 = traces of growth
2 = slight growth
3 = moderate growth
4 = covered with fungi The demonstrated efficacy of Compositions A and B against the six listed fungal organisms has utility not only on the tested substrate—wood—but also for protection of a variety of other materials that are attacked by one or more of the fungi, including paint, concrete, brick, textiles and leather.

Example 28

Using the standard AOAC fungicidal test method (12th Edition, 1975), the composition below was evaluated against two widespread fungi.

| | |
|---|---|
| Oxine | 2.08 parts by weight |
| Copper hydrate | 0.70 parts by weight |
| DDBSA | 40.00 parts by weight |
| Isopropanol | 32.00 parts by weight |
| Demineralized water | 25.22 parts by weight |

The two fungi were *Aspergillis niger*, a ubiquitous black fungus which flourishes on a broad range of substrates, and *Trichophyton mentagrophytes*, a cause of "athlete's foot."

*A. niger*—at 1:200 use dilution in a water carrier, no growth after 10 minutes' exposure.

*T. mentagrophytes*—at 1:750 use dilution in a water carrier, no growth after 10 minutes' exposure.

Similar but somewhat lower efficacy results were obtained by substituting zinc-8-Q or aluminum-8-Q in the composition of this example, produced by reacting zinc oxide and aluminum hydroxide respectively with oxine.

Example 29

The compositions of this invention exhibit efficacy against a broad spectrum fungal plant pathogens, as illustrated by various use dilutions in a water carrier of the following composition:

| | |
|---|---|
| Copper hydrate | 1.70 parts by weight |
| 8-hydroxy quinoline | 4.44 parts by weight |
| Isopropanol | 35.00 parts by weight |
| DDBSA | 58.86 parts by weight |

A. Valencia Oranges

Tested on harvested fruit against Phomopsis stem-end rot and Diplodis rot, at a 1:100 use dilution, 2-minute dip application. After 3 weeks at 70° F., the following percentages of decay were noted:
Control (untreated)oranges—9.5% decay
Treated oranges—5.3% decay B. Sugar Cane An agar seeding test against *Ceratocystis paradoxa* (pineapple disease) at a 1:10,000 (100 ppm) use dilution yielded a 3.0 mm. inhibition zone.

C. Peach Trees

Tested against *Taphrina deformans* (causes leaf curl disease). Four test trees were sprayed twice, two weeks apart, with a 1:400 use dilution. Three months later, 100 leaves on each test tree were rated for leaf curl:
Control (untreated) leaves—100% leaf curl
Treated leaves—13.5% leaf curl D. Cotton Effectiveness against 11 fungi and 1 bacterium (*Xanthomonas malvacearum*) that are associated with disease of cottonseed, seedlings and other plants were evaluated in vitro, using the following compositions:

| | | |
|---|---|---|
| Composition #1 | Copper hydrate | 1.70 parts by weight |
| | 8-hydroxy quinoline | 4.44 parts by weight |
| | Methanol | 4.00 parts by weight |
| | Isopropanol | 30.86 parts by weight |
| | DDBSA | 59.00 parts by weight |
| Composition #2 | Copper hydrate | 2.80 parts by weight |
| | 8-hydroxy quinoline | 8.20 parts by weight |
| | Methanol | 4.00 parts by weight |
| | Isopropanol | 26.00 parts by weight |
| | DDBSA | 59.00 parts by weight |

Both compositions were prepared in accordance with procedures stated in previous examples.

The following results were obtained, expressed in parts per million (ppm) of total test composition in water carrier and the relative growth inhibition provided at each test strength on each tested organism. In the tables below:

| Test Organisms | contractions (ppm) | | | | | | |
|---|---|---|---|---|---|---|---|
| | 0 | 1 | 5 | 25 | 100 | 500 | 1000 |
| Composition #1 | | | | | | | |
| *Pythium ultimum* (41B) | 0 | 0 | 0 | 1 | 2 | 3 | 3 |
| *Rizoctonia solani* (1D) | 0 | 0 | 0 | 1 | 2 | 3 | 3 |
| Fusarium (4A) | 0 | 0 | 0 | 3 | 3 | 3 | 3 |
| Fusarium (4D) | 0 | 1 | 1 | 2 | 2 | 2 | 3 |
| *Fusarium roseum* (4C) | 0 | 0 | 0 | 1 | 2 | 2 | 3 |
| *Colletotrichum gossypii* (35A) | 0 | 0 | 0 | 1 | 2 | 2 | 2 |
| *Xanthomonas malvecearum* (2A) | 0 | 0 | 0 | 0 | 2 | 2 | 3 |
| Composition #2 | | | | | | | |
| *Pythium ultimum* (41B) | 0 | 0 | 1 | 2 | 2 | 2 | 2 |
| *Rhizoctonia solani* (1D) | 0 | 0 | 1 | 2 | 2 | 2 | 2 |
| Fusarium (4A) | 0 | 0 | 1 | 1 | 1 | 2 | 2 |
| Fusarium (4D) | 0 | 0 | 1 | 1 | 2 | 2 | 2 |
| *Fusarium roseum* (4C) | 0 | 0 | 0 | 2 | 2 | 2 | 2 |
| *Colletotrichum gossypii* (35A) | 0 | 0 | 0 | 2 | 2 | 2 | 2 |
| *Xanthomonas malvecearum* (2A) | 0 | 0 | 0 | 1 | 2 | 2 | 2 |
| Composition #1 | | | | | | | |
| Aspergillis sp. | | | | | | 1 | 1 |
| *Helminthosporium oryzae* | | | | | | 2 | 2 |
| *Mucor mucedo* | | | | | | 1 | 1 |
| Penicillium sp. | | | | | | 1 | 1 |
| Rhizopus sp. | | | | | | 1 | 1 |

0 = no apparent inhibition
1 = some inhibition
2 = considerable inhibition (little growth
3 = total inhibition (no growth)

Example 30

The composition of Example 23 was screened for fungal pathogen response as a foliar spray on beans and rice. The rating scale is from 0 (no pathogen control) to 10 (complete pathogen control). The concentration of active ingredient (in a water carrier) of all compositions tested is 33 parts per million (ppm). The active ingredient in the composition of Example 28 is expressed in terms of Cu-8-Q and the chemical as listed below for four comparative products. The comparative products tested were Karathane (2,4-dimitro-6-(2-octyl phenyl crotonate), Vitavax (5,6-dihydro-2-methyl-1,4-oxathiin-3-carboxanilide), Daconil (tetrachloroisophthalonitrile) and Maneb (manganese ethylenebisdithiocarbamate). The plants and diseases tested were bean mildew (*Erysiphe polygoni*), bean rust (*Uromyces phaseoli typica*) and rice spot (*Helminthosporium orazae* and *Cerocospora orazae*).

| | Bean Mildew | Bean Rust | Rice Spot |
|---|---|---|---|
| Example 28 composition | 8 | 10 | 10 |
| Karathane | 10 | — | — |
| Vitavax | — | 9 | — |
| Daconil | — | — | 10 |
| Maneb | — | — | 8 |

Example 31

The following composition was evaluated (diluted with water for use) in vitro for inhibition against two fungal pathogens, Botrytis sp and Alternaria sp., causal agents of a variety of plant diseases.

| | |
|---|---|
| Oxine | 2.08 parts by weight |
| Copper hydrate | 0.70 parts by weight |
| DDBSA | 40.00 parts by weight |
| Triton X-100 | 20.00 parts by weight |
| Isopropanol | 22.00 parts by weight |
| Water (demineralized) | 15.22 parts by weight |

The zone of inhibition agar plate test also was used to test Cunilate 2174 (diluted in mineral spirits for use) for comparison. The composition concentrations in the table of results below are expressed in parts per million (ppm) of Cu-8-Q. The larger the inhibition zone, the greater is the efficacy of the composition.

| | Botrytis | | | Alternaria | | |
|---|---|---|---|---|---|---|
| DDBSA/Cu—8-Q | | | | | | |
| Concentration (ppm) | 21 | 50 | 125 | 21 | 50 | 125 |
| Inhibition zone (mm) | 13 | 15 | 22 | 0 | 16 | 21 |

-continued

|  | Botrytis | | | Alternaria | | |
|---|---|---|---|---|---|---|
| Cunilate 2174 | | | | | | |
| Concentration (ppm) | 83 | 200 | 500 | 83 | 200 | 500 |
| Inhibition zone (mm) | 13 | 14 | 16 | 0 | 0 | 14 |

The DDBSA/Cu-8-Q solution of this invention exhibits an improvement in efficacy against the tested organisms by a factor of 4× in the case of Botrytis to 10× in the case of Alternaria.

Example 32

The DDBSA/Cu-8-Q solution of the preceding example (31), diluted 1:400 in a water carrier, was applied by spray nine times, at two-week intervals, to peach and nectarine cultivars during the growing season. The results against brown rot (*Monolinia fructocola*), compared to nontreated trees, is presented below.

|  | % Fruit Affected | |
|---|---|---|
|  | Peach | Nectarine |
| At harvest (treated) | 1 | 3 |
| At harvest (untreated) | 15 | 43 |
| Five days later (treated) | 3 | 6 |
| Five days later (untreated) | 60 | 67 |

Example 33

The DDBSA/Cu-8-Q solution of Example 31 was tested in vitro against a major turf pathogen, *Helminthosporium vagans*, via a standard agar plate culture technique, with these results:

|  | Fungus Colony Diameter |
|---|---|
| 1:6700 use dilution in water carrier | 1 mm |
| 1:3350 use dilution in water carrier | 0 |
| Control | 21 mm |

The results demonstrate very high efficacy in controlling this important pathogen. Complete control of *H. vagans* was achieved in this assay between 3.7 and 7.5 ppm of Cu-8-Q.

As illustrated in the examples to follow, the compositions of this invention have high efficacy against a broad spectrum of bacteria that are pathogenic to mammals and plant life, that contribute to reduced water quality, that cause deterioration of foodstuffs, that degrade a broad range of manufactured and natural materials and products, and which generate toxic metabolites (bacteria-toxins) that are among the most poisonous substances known to man.

Of particular interest is high efficacy against Gram-negative as well as Gram-positive microorganisms. Few antibacterial materials now available are effective against the Gram-negatives and still fewer provide economical control of them. A number of available antibacterials toxic to Gram-negative organisms have practical limitations which severely restrict use, including high mammalian toxicity, phytotoxicity, corrosiveness to skin and a variety of materials, strong odor, strong color, high volatility, low or erratic shelf stability, low or nonexistent residual activity, and prohibition of use at elevated temperatures.

The basic significance in the need for Gram-negative control lies in the fact that this bacterial category includes a number of widespread, virulent pathogens which are difficult to impossible to control with presently available antibiotics, notably Pseudomonas sp. typified by *Pseudomonas aeruginosa* PRD-10, the standard strain in the United States for evaluation of antibacterials for mandatory Gram-negative control applications.

The compositions herein disclosed eliminate or substantially reduce these use limitations inherent in many other germicides. The compositions are quite unique in having strong Gram-positive and Gram-negative activity combined with broad versatility of formulation and use plus a high degree of safety (low toxicity and zero to low skin and eye irritation). Add to this the high efficacy, broad spectrum antifungal activity of the compositions of this invention and the resulting range of toxicity to target organisms and safety to man, the most sensitive of hosts, is unique indeed.

The balance of toxicity provided by this invention to Gram-positive, Gram-negative and fungal microorganisms has special value in the broad consumer field of skin deodorancy. Present antibacterials suffer from the fact that they are effective primarily against Gram-positives, allowing Gram-negative and fungi overgrowth, a condition considered dangerous by many authorities.

Example 34

The DDBSA/Cu-8-Q solution of Example 25 was tested, along with a number of well known antimicrobial agents, against a broad spectrum screen of economically important Gram-positive and Gram-negative bacteria. All antimicrobial agents were incorporated in the agar bacterial growth media according to standard microbiological practices. The bacterial species were grown in nutrient broth; 24-hour cultures, the inoculum, then were streaked onto the nutrient agar plates containing the test antimicrobials. After a 24-hour incubation at the appropriate temperature, the plates were rated for presence or absence of bacterial growth.

Minimum bactericidal concentrations for each of the tested agents are stated in the following tabulation of results in parts per million (ppm) of active ingredient as defined in the description of each agent.

| Bacteria (ATCC No.) | Antimicrobial Agent (ppm* of active ingredient) | | | | | | |
|---|---|---|---|---|---|---|---|
|  | A | B | C | D | E | F | G |
| Gram-positive: | | | | | | | |
| *Bacillus cereus* | 1 | 100 | — | 7 | 8 | 5–10 | — |
| *Bacillus lichenforms* (27326) | 1 | 100 | — | 7 | 8 | 2–5 | — |
| *Bacillus megaterium* (27327) | 1 | 100 | — | 7 | 8 | — | — |
| *Bacillus subtillis* (37328) | 1 | 100 | — | 750 | 8 | — | 3 |
| *Micrococcus flavus* (10240) | 1 | 100 | — | 7 | 8 | — | — |
| *Mycobacterium phlei* (15610) | 1 | 10 | — | 7 | 8 | — | 3 |

-continued

| Bacteria (ATCC No.) | Antimicrobial Agent (ppm* of active ingredient) | | | | | | |
|---|---|---|---|---|---|---|---|
| | A | B | C | D | E | F | G |
| *Staphylococcus aureus* (6538) | 1 | 100 | 2083 | 7 | 8 | 1–3 | 3 |
| Gram-negative: | | | | | | | |
| *Alcaligenes faecalis* (337) | 10 | 1000 | — | 750 | 80 | — | — |
| *Alcaligenes marshalii* (21030) | 104 | 100 | — | 7 | 8 | — | — |
| *Escherichia coli* (11229) | 104 | 10,000 | — | 750 | 80 | 250–500 | 165 |
| *Flavobacterium arboresceus* (4358) | 10 | 10 | 4166 | 7 | 8 | — | — |
| *Klebsiella pneumoniae* (4356) | 10 | 10,000 | — | 750 | 8 | — | — |
| *Proteus vulgaris* | 10 | 1000 | — | 750 | 800 | — | — |
| *Pseudomonas aeruginosa* (15442) | 104 | 1000 | 4166 | 750 | 800 | 1000–2500 | 165 |
| *Salmonella cholerasuis* (10708) | 104 | 1000 | — | 750 | 80 | 250–500 | 165 |
| *Salmonella typhi* (6539) | 104 | 1000 | 2083 | 750 | 80 | — | 165 |

*stated value of "1" means 1 or less
A = the DDBSA/Cu—8-Q solution of Example 25 with the active ingredient expressed in terms of Cu—8-Q.
B = DDBSA.
C = phenol
D = Betadine, an iodine/polyvinylpyrrolidone complex containing 0.75% iodine. The active ingredient is iodine.
E = Alkyl dimethyl ammonium chlorides (61% $C_{12}$, 23% $C_{14}$, 11% $C_{16}$ and 3% $C_{10}$).
F = sodium pentachlorophenate
G = 2,3,5-trichloro-4-propylsulfonyl pyridine.
See Previous list of antimicrobial agents These data demonstrate the high efficacy of the composition of Example 25. On the basis of the average of the efficacies against all the test organisms, Composition A is 45 times superior to Composition B; 88 times better than Composition C; 10.7 times better than Composition D; and 3.5 times superior to Composition E.

On the basis of the average of the efficacies against the three test bacteria (*Staphylococcus aureus, Salmonella cholerasuis* and *Pseudomonas aeruginosa* PRD-10) required by the Environmental Protection Agency of a "hospital grade" disinfectant, Composition A is 10 times better than Composition B; 7.2 times better than Composition D; and 1.6 times better than Composition E.

Example 35

The composition set forth below was prepared by previously described procedures:

| | |
|---|---|
| Oxine | 2.08 parts by weight |
| Copper hydrate | 0.70 parts by weight |
| Isopropanol | 32.00 parts by weight |
| DDBSA | 40.00 parts by weight |
| Water (demineralized) | 25.22 parts by weight |

When evaluated as a bactericide by the AOAC Use Dilution Method (12th Edition, 1975), 10 ring carriers per organism, the following results were obtained (A=subculture and B=resubculture):

| | Use Dilution in Water Carrier | Negative | | Positive | |
|---|---|---|---|---|---|
| | | A | B | A | B |
| *Staphylococcus aureus* | 1:1000 | 10 | 10 | 0 | 0 |
| *Salmonella cholerasuis* (PRD-10) | 1:1000 | 10 | 10 | 0 | 0 |
| *Pseudomonas aeruginosa* | 1:400 | 10 | 10 | 0 | 0 |
| *Aerobacter aerogenes* | 1:400 | 10 | 10 | 0 | 0 |

A ten-minute kill is required against the first three pathogens for sale as a hospital grade disinfectant. Efficacy against the fourth organism, a major cause of slime in recirculated cooling water systems and pulp and paper mills, demonstrates utility of the composition as a slimcide.

Example 36

This composition was prepared and tested at one use dilution, 1:50 in water carrier, against the causal agent of potato ring rot bacteria (*Corynebacterium sepedonicum*):

| | |
|---|---|
| Oxine | 2.08 parts by weight |
| Copper hydrate | 0.70 parts by weight |
| DDBSA | 40.00 parts by weight |
| Triton X-100 | 20.00 parts by weight |
| Isopropanol | 22.00 parts by weight |
| Water (demineralized) | 15.22 parts by weight |

Infected potato seed readily contaminate potato seed cutters, sacks, bins, cellars, trucks and planting equipment with the highly infectious ring rot bacteria. The result may be infected potato plants, tubers and reduced yields.

The test procedure consisted of dipping unpainted, planed wood laths (6") into a slurry of infected ring rot tuber tissue, allowing excess slurry to drain off (3–5 minutes) and then spraying the contaminated lath with the test antibacterials. Three to five minutes later, healthy Norgold Russet potato seed pieces were rubbed vigorously against both sides of the contaminated and antibacterial-treated laths. The process was repeated using laths not contaminated with *C. sepedonicum* but treated with the test antibacterial agent. The rubbed seed pieces were stored in bags and later planted at the appropriate time.

In addition to the composition of the invention, untreated controls, 20% Clorox (1.05% sodium hypochlorite in water), formaldehyde (37% formalin diluted 1:120 in water) and Roccal (benzalkonium chloride or zephiran chloride) diluted with water to 800 ppm concentration were tested. The results of the test are tabulated below and refer to plants and tubers produced from the tubbed test seed pieces.

| Antimicrobial | Ring Rot Contaminated | % Plant Stored | % Ring Rot Plants | % Ring Rot Tubers | Yield cwt/acre |
|---|---|---|---|---|---|
| None (control) | Yes | 98 | 23 | 8 | 493 |

| Antimicrobial | Ring Rot Contaminated | % Plant Stored | % Ring Rot Plants | % Ring Rot Tubers | Yield cwt/acre |
|---|---|---|---|---|---|
| None (control) | No | 95 | 0 | 0 | 609 |
| DDBSA/Cu—8-Q | Yes | 98 | 0 | 2 | 631 |
| DDBSA/Cu—8-Q | No | 100 | 0 | 0 | 602 |
| 20% Clorox | Yes | 98 | 20 | 9 | 500 |
| 20% Clorox | No | 98 | 0 | 0 | 602 |
| Roccal | Yes | 98 | 20 | 9 | 515 |
| Roccal | No | 98 | 0 | 0 | 638 |

The composition of this example demonstrates superior control of the ring rot bacterium. Other species of the genus Corynebacterium are causal agents of disease in man and a variety of plant life.

Example 37

The composition below was prepared and tested for speed and range of antibacterial activity, in the absence and presence or organic matter (blood) for use in hospital disinfection, cold sterilization and antisepsis.

| | |
|---|---|
| Oxine | 4.1 parts by weight |
| Copper hydrate | 1.4 parts by weight |
| DDBSA | 65.0 parts by weight |
| Propylene glycol methyl ether | 29.5 parts by weight |

Many antimicrobial agents are partially or totally deactivated in the presence of organic matter, constituting a severe limitation to effectiveness of such agents for a number of uses such as wound antisepsis and medical instrumentation and surface disinfection where large amounts of organic matter often are encountered and sometimes are unavoidable.

The AOAC Use Dilution Confirmation Test (12th Edition, 1970) was modified as follows:

(a) The test temperature was 37° C.

(b) The ring carriers were soaked in sheep blood for two hours, air-dried for one hour, then contaminated with the test pathogen.

(c) The contaminated rings were contacted with the test antibacterial agent for 30-second, one-minute and three-minute periods.

The results are set forth in the following table, in which:

| Test Pathogen | Use Dilution in Water Carrier | In Absence of Blood | | | In Presence of Blood | | |
|---|---|---|---|---|---|---|---|
| | | 30 sec. | 1 min. | 3 min. | 30 sec. | 1 min. | 3 min. |
| Staphylococcus aureus | Undiluted | 0 | 0 | 0 | 0 | 0 | 0 |
| (ATCC 6538) | 1:10 | 0 | 0 | 0 | 0 | 0 | 0 |
| | 1:100 | 0 | 0 | 0 | 3 | 6 | 3 |
| Salmonella typhi | Undiluted | 0 | 0 | 0 | 0 | 0 | 0 |
| (ATCC 6539) | 1:10 | 0 | 0 | 0 | 0 | 0 | 0 |
| | 1:00 | 0 | 0 | 0 | 0 | 0 | 0 |
| Pseudomonas aeruginosa | Undiluted | 0 | 0 | 0 | 0 | 0 | 0 |
| (ATCC 15442) | 1:10 | 0 | 0 | 0 | 10 | 10 | 0 |
| | 1:100 | 0 | 0 | 0 | 10 | 3 | 3 |

0 = no growth in 10 of 10 tubes tested
1 = growth in 1 of 10 tubes tested
2 = growth in 2 of 10 tubes tested
3 = growth in 3 of 10 tubes tested
etc.

These results indicate that the test composition is capable of rapid antibacterial action in the presence of substantial amounts of organic matter against the three human pathogens generally considered as definitive for antibacterial efficacy evaluation.

Example 38

The composition of Example 28 was prepared for evaluation as a skin degerming agent against resident and transient flora. Six subjects were tested using the Modified Prices Multiple Basin Technique which measures reduction of skin flora as a percentage of that achieved by washing the hands with unmedicated soap. Bacterial counts were taken from the first, fourth and fifth basins. The counts from the first basin represent the transient bacterial flora and that of the fourth and fifth basins the resident flora. Prior to the test, none of the subjects used a medicated soap for one week.

The results set forth in the following table demonstrate a very high order of efficacy for the test composition for critical degerming uses such as a surgical scrub for operating room personnel and skin preparation at the surgical site.

| Subject | Basin | Unmedicated Soap Average No. of Organisms/Basin | Test Composition Average No. of Organisms/Basin | % Reduction |
|---|---|---|---|---|
| 1 | 1 | 2,500,000 | 60,000 | 97.6 |
| | 4 | 1,900,000 | 25,000 | 98.7 |
| | 5 | 1,300,000 | 15,000 | 98.8 |
| 2 | 1 | 1,700,000 | 30,000 | 98.2 |
| | 4 | 1,100,000 | 20,000 | 98.2 |
| | 5 | 800,000 | 1,000 | 99.9 |
| 3 | 1 | 800,000 | 40,000 | 95.0 |
| | 4 | 600,000 | 20,000 | 96.7 |
| | 5 | 500,000 | 1,000 | 99.8 |
| 4 | 1 | 2,000,000 | 50,000 | 97.5 |
| | 4 | 1,000,000 | 1,000 | 99.9 |
| | 5 | 800,000 | 1,000 | 99.9 |
| 5 | 1 | 1,500,000 | 40,000 | 97.3 |
| | 4 | 800,000 | 1,000 | 99.9 |
| | 5 | 500,000 | 1,000 | 99.8 |
| 6 | 1 | 1,900,000 | 50,000 | 97.4 |
| | 4 | 800,000 | 15,000 | 98.1 |
| | 5 | 520,000 | 1,000 | 99.8 |

Example 39

| | |
|---|---|
| Oxine | 2.08 |
| Copper hydrate | 0.70 |
| Nonyl phenol/EO surfactant* | 20.00 |
| DDBSA | 45.00 |
| Isopropanol | 15.00 |
| Water (distilled) | 17.22 |

(*1 mol nonyl phenol to 6 mols ethylene oxide)

The above composition was prepared by the procedure already described and evaluated for efficacy against ciliated protozoan and two types of viruses.

Hemaglutination Assays

| | HA Titre | | |
|---|---|---|---|
| Virus | Untreated | Treated (1:50)* | Treated (1:200) |
| Adenovirus | 128 | 0 | 0 |
| Newcastle Disease virus | 512 | 0 | 0 |

(*1:50 and 1:200 use dilutions of composition in a water carrier in contact with virus suspensions for 15 minutes)

The HA titre is a measure of the number of infectious virus particles present in the test suspension.

Plaque Assays

Via the same procedure as above, the untreated virus suspensions contained $6.4 \times 10^4$ pfu/ml of Adenovirus virus particles and $21 \times 10^5$ pfu/ml Newcastle Disease virus particles respectively. After treatment with the 1:50 and 1:200 use dilutions, readings of 0 pfu/ml were obtained. Each pfu represents one infectious virus particle. A zero pfu reading represents total inactivation of the infectious virus.

Protozoan Inhibition

Inhibition of growth of ciliated protozoan (Tetrahymena) in pond water was obtained at a 6 ppm concentration (based on Cu-8-Q) of the above test composition of DDBSA and Cu-8-Q after 6 hour and 72-hour contacttimes. The 6 ppm reading represents the MIC (Minimum Inhibitory Concentration). These results demonstrate high efficacy of the test composition against the test microorganisms.

Example 40

In some instances, it may prove advantageous to include other microbicides in a given formulation to increase the over-all spectrum of antimicrobial activity. Such additional microbicides need not necessarily be of the type thus far described in this specification. For example, when treating green lumber to inhibit sapstain or mold, it is sometimes desirable, to get broader protection, to include a chlorophenol such as pentachlorophenol, tetrachlorophenol, or 2,4,5-trichlorophenol, in the composition of this invention. Also, to provide additionally against insect attack, it is within the scope of this invention to include insecticides such as Lindane or DDT.

Further, it has been found that boric acid can be added to the class of compositions of this invention with beneficial microbiocidal results:

| | |
|---|---|
| Copper hydrate | 0.035 |
| 8-hydroxy quinoline | 0.104 |
| Methanol | 0.736 |
| DDBSA | 1.630 |
| Orthoboric acid | 2.500 |
| Water | 94.995 |

The above concentrate, prepared as previously described, was diluted 1:9 with water and fresh, rough-sawn, green southern yellow pine lumber was treated by 10-second dip immersion. Sample boards were placed, together with an equal number of untreated control boards and other test specimens in a chamber maintained at 75° F. and 70% relative humidity for 28 days.

| | % Stain and Mold |
|---|---|
| DDBSA/Cu-8-Q composition of Example 5 1:200 use dilution in water | 6 |
| DDBSA/Cu-8-Q/orthoboric acid solution described immediately above | 7 |
| DDBSA/Cu-8-Q composition of Example 5 1:400 use dilution in water | 14 |
| Orthoboric acid, 0.50% in water | 62 |
| Orthoboric acid, 0.25% in water | 86 |
| Untreated control boards | 88 |

Example 41

Some of the compositions of this invention exhibit unexpected insecticidal activity when compared to the conventional solubilized Cu-8-Q compositions and when compared to a known insecticide (pentachlorophenol). Against termites in a soil burial test in Memphis, Tenn., the following compositions were evaluated:

(a) Example 12, diluted with water to a 0.25% Cu-8-Q content;

(b) Example 18, diluted with mineral spirits to a 0.25% Cu-8-Q content;

(c) Cunilate 2174, diluted with mineral spirits to a 0.25% Cu-8-Q content; and (d) A 5.0% pentachlorophenol solution in mineral spirits containing 4% propylene glycol ether to provide sufficient pentachlorophenol solubility and to prevent sublimation from the wood.

Dry southern yellow pine stakes, ¾" square × 24" long, were dip-impregnated with the test solutions, allowed to dry for one week, and then buried to a depth of 12" in the ground for 15 months, at which time these results were observed:

| Treatment | Solution Pickup (lbs/ft$^3$) | Termite Rating* |
|---|---|---|
| None (control stakes) | — | 36 |
| Example 12 | 1.79 | 83 |
| Example 18 | 1.13 | 80 |
| 5% pentachlorophenol solution | 1.28 | 84 |
| Cunilate 2174 | 1.26 | 56 |

(*Termite rating:
0 = stakes totally destroyed
100 = stakes unattacked)

Both compositions of this invention exhibited termite control essentially equal to that of the pentachlorophenol solution and definitely superior to both the untreated control stakes and those treated with Cunilate 2174.

Examples 42 to 50

As further evidence of the effectiveness of antimicrobials prepared in accordance with this invention, a number of tests were conducted utilizing DDBSA as the disubstituted aryl compound of this invention as a solution with the below-listed microbicidal agents. A 1:200 use dilution in a water carrier was prepared from concentrates containing 65 parts DDBSA, 30 parts methanol, and 5 parts of the antimicrobial agent. Fresh-cut green pine test boards were dip-treated and evaluated for stain and mold after 30 days in the aforementioned constant atmosphere test chamber:

| Example | Antimicrobial Agent | % Mold and Stain |
|---|---|---|
| 42 | Cu-8-Q | 3 |
| 43 | 2-(4-thiazolyl) benzimidazole | 14 |
| 44 | cis-N—(trichloromethyl) thio-4-cyclohexane-1,2-dicarboximide | 23 |
| 45 | diiodomethyl-para-tolyl sulfone | 8 |
| 46 | para-chlorophenol diiodomethyl sulfone | 6 |
| 47 | 2-n-octyl-4-isothiazolin-3-one | 10 |
| 48 | 2-benzisothiazolin-3-one | 14 |
| 49 | Mergal BCM | 2 |
| 50 | 8-hydroxy quinoline | 10 |

Example 51

The following composition was prepared and evaluated for control of pineapple disease of sugar cane (*Ceratocystis pilifera*):

| | |
|---|---|
| 2-(methoxy-carbamoyl)-benzimidazole | 4.0 |
| DDBSA | 70.0 |
| Propylene glycol methyl ether | 26.0 |

Sugar cane seed was treated with this solution as diluted with a water carrier. Seed also was treated with benomyl, thiophanate methyl, Panoctine (9-aza-1,17-diquanidinoheptadecane triacetate), hot water and cold water. The results are tabulated below:

| | Concentration, ppm of active ingredients (1) | % Emergency Inoculated (2) |
|---|---|---|
| DDBSA/2-(methoxy-carbamoyl)-benzimidazole | 50 | 48 |
| | 100 | 54 |
| | 200 | 53 |
| Thiophanate methyl | 50 | 55 |
| | 150 | 51 |
| | 300 | 49 |
| Panoctine | 50 | 48 |
| | 100 | 48 |
| | 200 | 53 |
| Benomyl | 150 | 50 |
| Hot water | 0 | 36 |
| Cold water | 0 | 27 |

(1) The active ingredient for the composition of this example is stated in terms of the benzimidazole content; all others are stated in terms of the listed chemical compound.
(2) Prior to planting, the seed was inoculated with the causal disease organism, *Ceratocystis pilifera*. Emergence data was collected 56 days after planting.

These results demonstrate the in vivo efficacy of the compositions of this example. Additionally noteworthy is the fact that, at the 27-day mark, the emergence rate was noticeably higher for the composition of this example as compared to all other treatments.

Example 52

The foregoing examples involve complexes between the disubstituted aryl compound and known antimicrobials. Another feature of the invention is the discovery that some agents not ordinarily considered to be antimicrobial are effective when dissolved in the disubstituted aryl compounds of this invention. A case in point is phthalimide which is not offered commercially as a fungicide and which Horsfall, in *Principles of Fungicidal Action*, describes as having very little fungicidal activity. Yet the composition described below exhibits excellent control of stain and mold fungi in green lumber.

| | | |
|---|---|---|
| Phthalimide | 0.44 | lbs. |
| DDBSA | 0.88 | lbs. |
| Sodium hydroxide | 0.44 | lbs. |
| Water | 100.00 | gallons |

The sodium hydroxide was dissolved in one quart of water, the phthalimide then added and the mixture stirred until a clear solution resulted. The DDBSA was then added with stirring, followed by the balance of the water. The composition was evaluated by treating green, rough-sawn southern yellow pine boards. After two weeks' exposure:

| | % Mold and Stain |
|---|---|
| DDBSA/phthalimide solution | 0 |
| Untreated control boards | 45 |

It is theorized, and indicated by Horsfall, that phthalimide is an active toxiphore, yet is essentially ineffective as an antimicrobial because of its low fat solubility.

According to the concept of this invention, when a solution is formed between phthalimide and the disubstituted aryl compound, the oleophilic substituent may lead the toxiphore into the microbial cell and act as an active antimicrobial. Other active toxiphores, such as benzimidazole, which lack only fat solubility for antimicrobial activity, can be converted by this same concept into active antimicrobials.

Example 53

High water hardness and/or high use dilutions can cause precipitation of the composition of this invention which otherwise would remain in true solution in water. In some instances of use, it is desirable to maintain the true solution character of the diluted composition. It has been found that a number of modifications to the composition will either eliminate or delay the formation of solid matter in the use solution, the presence of such particulate matter being evidenced generally by a cloudy appearance. Among the more effective of such modifying agents are (1) partial or total replacement of the diluting water with a lower alcohol such as methanol, ethanol or isopropanol, or (2) additional of nonionic surfactants such as alkyl phenol ethoxylates.

The following compositions were prepared:

| | A | B |
|---|---|---|
| Oxine | 2.07 | 0.72 |
| Copper hydrate | 0.70 | 0.25 |
| DDBSA | 40.00 | 14.00 |
| Isopropanol | 20.00 | 7.00 |
| Distilled water | 37.23 | 52.03 |

-continued

|                          | A    | B     |
|--------------------------|------|-------|
| Octyl phenol ethoxylate (9 EO) | —    | 26.00 |

Composition A exhibited solution clouding when diluted 1:300 with water containing 120 ppm hardness (total dissolved solids), whereas Composition B did not. In terms of the Cu-8-Q/DDBSA content, a 1:300 dilution of Composition B is the equivalent of a 1:857 dilution of Composition A.

Example 54

The alkyl aryl sulfonic acids of this invention, typified by DDBSA, are strong acids and, as such, are harmful to many substrates and, in particular, are highly corrosive to human skin and capable of producing severe irritation and burns. The addition of metal-oxine compounds to DDBSA, as described herein, reduces the corrosive action of DDBSA significantly, even in small amounts. This is entirely unexpected and no adequate explanations for this fact has yet been found.

The following compositions were prepared (all parts by weight):

|                          | A    | B    | C    | D    |
|--------------------------|------|------|------|------|
| Oxine                    | 8.2  | 4.1  | 2.1  | —    |
| Copper hydrate           | 2.8  | 1.4  | 0.7  | —    |
| DDBSA                    | 59.0 | 59.0 | 40.0 | 59.0 |
| Propylene glycol methyl ether | 30.0 | 35.5 | 57.2 | 41.0 |

These compositions were tested for skin irritation by rubbing 2 ml of each onto the hands of six test subjects. After 60 seconds, Compositions A, B and C were rinsed off the hands with water. None of the test subjects noted any adverse effect such as stinging, burning, itching or warming during the test or thereafter. The results with Compositions D and E were observably different. With 5 seconds after application, all test subjects noted a strong heating, burning sensation that required immediate and thorough removal with running water. A relatively mild stinging sensation was noted thereafter by four of the six test subjects for periods of about thirty minutes to two hours.

The compositions of this invention exhibit a unique combination of cleaning effectiveness and mildness heretofore unknown in cleaning agents. More specifically:

Effectiveness—Equal to superior to the best traditional types of cleaning agents. Cleaning efficacy, particularly notable on metals, concrete, brick, porcelain and grouting, is applicable both to inanimate substrates and human uses.

Mildness—Even at concentrations much higher than normal use dilutions, no adverse effects upon the hose substrate are noted when employed in typical cleaning procedures. Such substrates include painted surfaces, most metals, concrete, brick, porcelain enamel, wood, plastics, wool, leather, glass, cotton, linen, synthetic fabrics and the like. This unusual mildness and lack of irritation is observed also in human uses, even upon the most delicate skin areas, eyes and mucous membranes. On delicate body surface areas, the compositions proved significantly less irritating than Ivory Soap, a long-time standard for mildness.

High cleaning efficacy for general purpose uses coupled with unusually low substrate damage potential to inanimate substrates and lack of irritation to humans and animals is uncommon in low pH products and unusual even in conventional cleaners in the relatively neutral pH range (6 to 8). By comparison, the pH of use concentrations of the composition of the invention most generally range from about 1.5 to about 2.5.

Historically, cleaning agents have been alkaline, and the higher the alkalinity, the greater is the effectiveness and harshness. In recent years, a trend toward mildly acid chances (pH 5 to 6) for certain specialty uses—hair shampoos, for example—has been underway, and highly acidic and oxidizing cleaning materials are traditional for certain highly specialized applications such as metal, dairy equipment and toilet bowl cleaning. In these cases, the acidity serves a specific purpose, such as removal of oxide (metals), hardened milk deposits (dairies) and iron discoloration (toilet bowls). Such products, however, damage most substrates and are much too corrosive for human use. The low pH compositions disclosed herein not only are contrary to traditional concepts, but exhibit an extremely broad range of consumer, commercial and industrial uses ranging from a vaginal douche at one extreme to cast iron engine block cleaning at the other end of the spectrum. In certain specialized applications where highly acid cleaners have long been used, the compositions will provide equal to superior cleaning action without the associated dangers. For example, the compositions will clean most leather surfaces more effectively than an oxalic acid/water solution, a recommended leather cleaner which is toxic, and corrosive to humans, animals and most substrates.

It is within the scope of this invention to modify the disclosed compositions to improve performance or alter physical properties and meet final product needs for a wide range of end uses in many fields, including product material and process preservation, medical, animal health care, water treatment, plant disease control, disinfection, sanitization and cleaning, cosmetics and toiletries.

In many instances, the compositions of the invention constitute only a minor portion of the final product formulation, in substantial measure because the high efficacy requires only small amounts. The rule for use of other ingredients in the disclosed compositions is simple and obvious—namely, such ingredients must be compatible with the compositions and must not deactivate the antimicrobial activity below a usable level. Among the types of usable and desirable other ingredients are wetting agents, detergents and surfactants, emollients, other pesticides, thixotropes, film-formers, foam-builders and antifoamers, soil antideposition and antiredeposition agents, wet slip enhancers, fillers, colorants, taste modifiers, odor masking agents and fragrances, fire retardants, corrosion inhibitors, chelators for undesirable metals including those causing water hardness, and acidification and alkalization agents. Generally, the compositions of this invention must be maintained, at the desired use dilution and at the time of use or incorporation into another composition, material or product, at a pH of about 3.5 or below. The preferred pH, at least when metal oxines are used, is below 2.8.

The antimicrobial compounds of this invention are effective to control odors caused by biological activity. Since many of the compounds become affixed to many substrates, their value as an antimicrobial and odor destroyer will remain for a prolonged period of time and even survive many washings of certain substrates, such as garments.

The physical form of the compositions of this invention can vary widely. The most commonly desirable form is a low viscosity liquid—the form of the examples given above. But other forms fall within the scope of the invention and may be preferred for certain end uses, including solids, powders, high viscosity liquids, ointments and creams, and gels. All of the foregoing examples consist of compositions that are true solutions, both in concentrate and use-diluted form. Such true solution compositions generally are preferred for the majority of cases for a number of practical handling and application reasons. However, compositions that are in emulsion form or which exist as liquid or solid suspensions are within the scope of this invention and have definite utility.

The compositions described above will hereinafter be referred to as the "compositions of section 1".

SECTION 2

We have also discovered that the antimicrobial activity of known phenolic antimicrobials can be improved by mixing a minor amount of such known phenolic antimicrobials with a major amount of a solution prepared by solubilizing a nonphenolic antimicrobial agent as set forth in section I with a disubstituted aryl compound having a hydrophilic and an oleophilic substituent (as described in section I hereinabove). In one preferred embodiment said second antimicrobial agent is an organometallic compound (as described in section I above) such as a metal chelate of oxine and the disubstituted aryl compound is alkyl benzene sulfonic acid (most preferably DDBSA in which the alkyl chain predominates in $C_{10}$ to $C_{13}$.)

Certain phenolic compositions are known to the prior art that have efficacy against certain microbials including fungi and Gram-positive and Gram-negative bacteria. Many of these phenolics are falling into disfavor because of their relatively high toxicity toward animal and plant life. This is particularly true since, for many applications, an undesirably large amount of phenolics must be used to achieve a desired degree of antimicrobial activity against certain microbes. The utilization of phenolic antimicrobials is further limited in that they are frequently limited in the spectrum of microbes against which they display effective antimicrobial activity.

Accordingly, a further object of this invention is to improve the efficacy of phenolic antimicrobial agents.

A related object of this invention is to formulate phenolic antimicrobial compositions in a manner in which effective antimicrobial activity can be achieved with a minimum quantity of the phenolics.

Another object of this invention is to widen the spectrum of microbes over which phenolic compositions display effective antimicrobial activity.

These and other objects of this invention are achieved by including a minor amount of an antimicrobial phenolic composition in a solution comprised of a non-phenolic antimicrobial composition as set forth in section I and a disubstituted aryl compound as set forth in section I.

This embodiment of our invention is illustrated by the following examples:

EXAMPLE 1

The following two compositions were prepared (amounts are weight percent):

|  | A | B |
|---|---|---|
| Oxine | 2.05 | 2.05 |
| Copper hydrate | 0.70 | 0.70 |
| DDBSA | 40.00 | 40.00 |
| Isopropanol | 32.00 | 32.00 |
| Distilled water | 25.25 | 15.25 |
| Orthophenyl phenol | — | 10.00 |

Both compositions were tested against the Gram-positive *Staphylococcus aureus* bacterium in accordance with the AOAC Use Dilution Confirmation Method with these results:

|  | Use Dilution in Water | No. of Tubes Tested | |
|---|---|---|---|
|  |  | Positive* | Negative* |
| A | 1:1000 | 0 | 10 |
| A | 1:1250 | 1 | 9 |
| B | 1:1250 | 0 | 10 |
| B | 1:1500 | 1 | 9 |

(*positive - growth; negative - no growth)

These results indicate that efficacy of Composition A was improved by about 20–25% by addition of 10% orthophenyl phenol to Composition A (forming Composition B). By calculation, using technical bulletins published by the producer of orthophenyl phenol for disinfectant formulation, the efficacy improvement should have been about 4%. In short, the orthophenyl phenol addition actually improved efficacy by a factor of five to six times the calculated theoretical improvement.

EXAMPLE 2

Composition C was prepared as follows (amounts are weight percent):

| Oxine | 2.05 |
|---|---|
| Copper hydrate | 0.70 |
| DDBSA | 40.00 |
| Isopropanol | 32.00 |
| Distilled water | 15.25 |
| 4-chloro-2-phenyl phenol | 10.00 |

Composition C was tested and compared with Composition A of Example 1 against the standard Gram-negative bacterium *Pseudomonas aeruginosa* PRD-10 in accordance with the aforementioned AOAC Use Dilution procedure, with these results:

|  | Use Dilution in Water | No. of Tubes Tested | |
|---|---|---|---|
|  |  | Positive* | Negative* |
| A | 1:500 | 1 | 9 |
| C | 1:750 | 0 | 10 |

(*positive - growth; negative - no growth)

Reference tests on antibacterials and the manufacturer's technical literature on 4-chloro-2-phenyl phenol indicate that this phenol has very low activity against *P. aeruginosa* (a phenol coefficient of "less than 10"). Even assuming a phenol coefficient of as high as 10, the amount of 4-chloro-2-phenyl phenol in Composition C should have improved, by calculation, the use dilution efficacy of Composition C by about 4% over that of Composition A which contains no phenol. Instead an improvement of an indeterminate amount in excess of 50% was obtained, indicating that the addition of the phenol to Composition A improved its antibacterial activity out of all proportion to the amount of phenol added.

The antifungal efficacy of these phenolics is improved by formulation in accordance with this invention. Orthophenyl phenol, 2,3,5-trichlorophenol, tetrachlorophenol and pentachlorophenol, for example, exhibit antifungal efficacy improvement significantly higher than would be expected when formulated conventionally, especially for use in a water carrier where customary formulation methods employ a water-soluble alkaline salt of such phenols, such as the sodium or potassium salts.

The quantity of phenolic antimicrobial added to the antimicrobial solution is not critical and can be varied depending on the microorganism that it is desired to control and the permitted toxicity of the total composition. As noted in the examples, a 10% inclusion of a phenolic is quite effective and can vary over a wide range, although 5-20% is generally preferred.

SECTION 3

We have also discovered a method for reducing the skin and eye irritation of alkyl aryl sulfonic acids (as set forth in Section 1). In a preferred embodiment, the irritation-reducing agent is an organometallic antimicrobial agent (as set forth in section I) which is solubilized in the alkyl aryl sulfonic acids and which in addition provides for antimicrobial efficacy. The irritation of the solution can further be reduced by including a second irritation-reducing agent such as polyvinyl pyrrolidone or selected surfactants such as ethoxylated and prothoxylated long-chain aliphatic alcohol type surfactants, ethoxylated alkyl phenol type surfactants or a sulfosuccinate of a higher fatty acid monoethanolamid. The following Examples are illustrative:

EXAMPLE 1

A commercial grade of undiluted DDBSA was poured onto and spread over the hands of several persons. An almost immediate warm and uncomfortable sensation was noted, causing the persons to flood their hands with water to remove the DDBSA.

The experiment was repeated, using DDBSA into which had been dissolved 10% by weight of copper-8-quinolinolate (Cu-8-Q). No immediate sensation of discomfort was felt as had been the case with the unmodified DDBSA.

EXAMPLE 2

The following composition was prepared:

| Oxine | 2.05 parts by weight |
| Copper hydrate | 0.70 parts by weight |
| DDBSA | 40.00 parts by weight |
| Isopropanol | 15.00 parts by weight |
| Water | 42.75 parts by weight |

A second test solution also was prepared wherein five parts of the water in the above composition was replaced by an equal amount of polyvinyl pyrrolidone (PVP) solution in water (GAF's NPK-60).

The two compositions were tested for skin irritation by placing two drops of one composition on the skin at the inside of one elbow of five test subjects and two drops of the other composition on the same spot on the other elbow of each subject. In all cases, the composition was smeared over about a one-half square inch of skin and the subjects' reactions were noted over a 20-minute test period.

The first composition (no PVP) was described variously as "burning," "stinging," "tingling" and "warming". The second composition (containing PVP) was described by the subjects over the range of noticeably milder skin sensation to none at all.

A third composition was prepared, identical to the second except that the PVP content was increased to twenty parts, again replacing an equal amount of water. Tested as before, no skin sensation was reported by any of the test subjects.

EXAMPLE 3

These compositions were prepared (all parts by weight):

|  | A | B |
| --- | --- | --- |
| Oxine | 4.1 | 4.1 |
| Copper hydrate | 1.4 | 1.4 |
| DDBSA | 60.0 | 60.0 |
| Isopropanol | 34.5 | 24.5 |
| PVP (NPK-60) | — | 10.0 |

The compositions were tested on three subjects for skin irritation by spreading two drops of each composition over a one square inch area of skin just below one eye of each test subject and the other composition on the same spot beneath the other eye.

Composition A became uncomfortable on the three test subjects within one to three minutes and was removed. Composition B exhibited no sensation of discomfort to much milder sensation than Composition A for the ten-minute duration of the test.

EXAMPLE 4

The first composition of Example 1 was prepared containing 30% PVP solution. When tested in accordance with the procedure of Examples 1 and 2, no sensation of skin discomfort was noted by any of the test subjects.

EXAMPLE 5

It further has been discovered that a range of ethoxylated and prophoxylated long-chain aliphatic alcohol type surfactants and ethoxylated alkyl phenol type surfactants provide noticeable skin irritation reduction for compositions of the type disclosed in previous examples, using the same test procedures. These nonionic surfactant types do not appear, however, to be as effective as PVP, but have proved particularly useful for many applications where the detergency characteristics of these additives to the basic compositions of the invention are desirable. Examples of useful surfactants in these classes include phenols with $C_8$ through $C_{12}$ alkyl side chains, alcohols with $C_{10}$ to $C_{22}$ chain lengths and ethylene oxide and propylene oxide adducts thereon from about 4 to about 100. Suitable alkyl phenols include octyl phenol, nonyl phenol and dodecyl phenol plus dinonyl and didodecyl phenols.

By way of example, the first composition of Example 2 was prepared except that 20 parts of water were replaced with an equal amount of octyl phenol ethoxylate (9 EO). Tested as before, this composition exhibited distinctly less skin irritation than without the octyl phenol ethoxylate.

Another additive found to reduce the irritation of the compositions of the invention is a sulfosuccinate of a higher fatty acid monoethanolamid sold by Cyclo Chemicals Corporation under the designation Cyclopol SBR-3. Significant improvement in irritation characteristics was observed using 3%. 10% and 20% replacements of water in the first composition of Example 2 with this material, which has a 40% active ingredient content.

It should be noted that no critical lower or upper limits have been noted as to the amounts of these irritation reduction agents which may be used in the practice of this invention. Generally, increased amounts produced greater reductions in irritation. The quantity added may be varied not only to obtain the desired irritancy reduction, but also to obtain other desired properties in the final formulation.

SECTION 4

We have also discovered a method for materially increasing the solubility of compounds having insecticidal properties. Other compounds heretofore recognized as having only antimicrobial activity become useful for insecticidal purposes when solubilized, particularly through the use of a disubstituted aryl compound described in section 1, particularly an alkyl benzene or naphthylene sulfonic acid.

Thus, our invention also includes insecticides which may be made water-soluble, at least in concentrated form, and which may, in some of the formulations display reduced toxicity towards mammalian and plant life.

The compositions set forth in section I have been found to exhibit an unexpected degree of insect control. This has importance in a variety of end uses, notably wood preservation, wherein there is little advantage in protecting wood from fungal decay if the wood is preserved only for insects, such as termites, to destroy. In many areas of the world, including those with high decay rates, destruction of wood by termites occurs more rapidly than does fungal degradation.

It also has been found that the compositions set forth in section 1 are compatible with a broad range of well-known insecticidal chemicals in use for a broad range of agricultural, medical, animal health care, product and material preservation, and miscellaneous pest control applications. This discovery extends the end use range of the compositions of section 1 where insect control in addition to that afforded by the composition itself is desired, or in those instances where the basic composition provides no control of the target pests. Providing insect and antimicrobial control in one composition also has both economic and convenience advantages.

Entirely unexpected is our discovery that a number of standard insecticides incorporated in the compositions of section 1, including DDBSA alone or in combination with an antimicrobial, form true solutions in the formulation concentrates and, of far greater significance, true solutions when water-diluted for use. Most insecticides are water-insoluble and consequently must be formulated for use as wettable powders, flowables, or as emulsifiable liquid concentrates. Generally, these products, when diluted for use with water as the carrier, form suspensions or emulsions of mediocre stability, requiring frequent agitation to maintain an acceptable degree of dispersion in the carrier. True solutions are easier to use and provide more uniformity of coverage of the substrate or host organism for protection against the target organisms. True solutions also make practical certain end uses where suspensions and emulsions of inadequate stability and poor substantivity are not functionable. Such suspensions and emulsions, for example, will not penetrate wood adequately. For long-term protection of wood for many uses, deep impregnation is mandatory.

A number of additional standard insecticides form true solutions when incorporated into the compositions of section 1 in concentrated form, but form-stable colloidal emulsions when water-diluted for use. Such emulsions for most uses offer all of the advantages of true water solutions in terms of desired stability and ability to penetrate and adhere to substrates such as wood and tight-weave fabrics.

While water generally is the carrier of choice for preparing dilutions, other carriers have utility in certain instances, including hydrocarbons and a variety of polar organic solvents.

A criterion for combining insecticides with compositions of the basic invention is stability of the insecticide to acidic media. The amount of insecticide practically incorporatable into composition concentrates for subsequent use dilution in true solution or stable emulsion form depends upon a number of factors including inherent solubility characteristics of the insecticide in the basic composition of section 1 and the make-up of this basic composition. The larger the amount of DDBSA in said basic composition the larger the quantity of a given insecticide that may be solubilized in the basic composition. The ratio of insecticide to said basic antimicrobial composition is relatively noncritical and the choice in large measure depends upon the desired combination of antimicrobial-to-insecticidal performance.

Among the useful insecticides that may be incorporated into the solubilizing disubstituted aryl compounds of section 1, either with or without antimicrobials according to section 1, are carbaryl, methoxychlor, lindane, chlordane, malathion, parathion and methyl parathion, toxaphene, dieldren, aldrin, endrin, heptachlor, baygon and cygon. TBTO (tributyl tin oxide) which is not a recognized insecticide, also has utility against marine wood borers.

In cases where antimicrobial action is not wanted, it is within the scope of this invention to incorporate the insecticide in the disubstituted aryl compounds of section 1 plus a diluent. However, some insecticides seemingly exhibit reduced solubility characteristics in the absence of a metaloxine chelate according to section 1.

An important area of use for the insecticide-antimicrobial compositions described in this section relates to the known usefulness of certain insecticides for protection of wood in marine service against marine borers which attack and destroy wood rapidly. There are three important species of wood-destroying borers in two classes: (1) Molluscan—Teredo and Martosia sp., and (2) Crustacean—Limnaria sp. It is near-axiomatic that no one toxicant is effective against all three species, and it is a fact that in certain tropical waters, no single wood impregnant has provided satisfactory durability. For example, some waters off Key West Florida are inhabited by combinations of marine borers which will destroy a wood piling impregnated with 20 lbs of creosote per cubic foot in five years, despite the fact that heavy creosote loadings in wood are considered to be the preservative of choice for marine applications the world over. Additions to creosote of chlordane, dieldrin, and TBTO among other insecticides is reported to substantially improve creosoted wood piling durability in certain waters.

Accordingly, addition of these insecticides to the basic antimicrobial composition of section 1 provides improved wood durability in marine environments. Additionally, our discovery allows use of suitable insecticides in a water carrier for impregnation of wood for the first time.

Many of the known insecticide compounds presently available are objectionable in varying degrees due to the toxicity they display toward animal and plant life. This is in distinction to the antimicrobial compounds of section 1, which at use dilutions, are generally considered non-toxic. Thus, when both toxicity and efficacy are important, it is possible to use the antimicrobials in combination with known insecticides in order to substantially retain effectiveness while reducing the amount of the toxic insecticides that must be used.

The examples which follow demonstrate the uses and practice of our discoveries:

EXAMPLE 1

The composition below was prepared and tested for protection of wood against termite attack (amounts are parts by weight):

| | |
|---|---|
| Oxine | 4.1 |
| Copper hydrate | 1.4 |
| DDBSA | 65.0 |
| Methanol | 29.5 |

The test procedure was AWPA (American Wood Preservers' Association) Method M12-72, revised 1973. The termite species employed was *Reticulitermes flavipes*. The test blocks were southern pine sapwood and the test period was four weeks.

| Composition Retention in Wood (pcf)* | | % Weight |
|---|---|---|
| Total Composition | Cu-8-O | Loss |
| 0 | 0 | 10.1 |
| 0.38 | 0.201 | 0.1 |
| 0.62 | 0.033 | 0.6 |
| 0.84 | 0.045 | 0 |

(*"pcf" means pounds per cubic foot of wood)

These data indicate that the test composition provides adequate protection against termites at the lowest concentration evaluated.

EXAMPLE 2

The following composition was prepared (amounts are parts by weight). The composition was a true solution. When diluted 1:9 with water for use, a true, stable solution resulted.

| | |
|---|---|
| Oxine | 7.4 |
| Copper hydrate | 2.5 |
| DDBSA | 53.0 |
| Chlordane | 10.0 |
| Propylene glycol methyl ether | 27.1 |

EXAMPLE 3

The following compositions were prepared (amounts are parts by weight):

| | A | B |
|---|---|---|
| Oxine | 7.4 | 7.8 |
| Copper hydrate | 2.5 | 2.7 |
| DDBSA | 53.0 | 53.0 |
| TBTO | 10.0 | 5.0 |
| Propylene glycol methyl ether | 27.1 | 31.5 |

Both formed true solutions are prepared. Diluted 1:9 with water, Composition A formed a stable colloidal emulsion. Diluted 1:9 and 1:99 with water, Composition B formed true solutions.

EXAMPLE 4

The following compositions were prepared (amounts are parts by weight):

| | A | B |
|---|---|---|
| Oxine | 7.4 | 7.8 |
| Copper hydrate | 2.5 | 2.7 |
| DDBSA | 53.0 | 53.0 |
| Toxaphene | 10.0 | 5.0 |
| Propylene glycol methyl ether | 27.1 | 31.5 |

Both produced true solutions as prepared. Composition A formed a stable colloidal emulsion when diluted 1:9 with water. Composition B produced 1:9 and 1:99 dilutions in water with a slightly hazy appearance, indicating a borderline condition between a true solution and a colloidal emulsion.

EXAMPLE 5

The following composition was prepared (amounts are parts by weight):

| | |
|---|---|
| Oxine | 4.1 |
| Copper hydrate | 1.4 |
| DDBSA | 65.0 |
| Malathion | 5.0 |
| Methanol | 24.5 |

As prepared, the composition was a true solution. Dilution 1:99 with water for use also produced a true solution.

EXAMPLE 6

The following composition was made (amounts are parts by weight):

| | |
|---|---|
| Oxine | 4.1 |
| Copper hydrate | 1.4 |
| DDBSA | 65.0 |
| Carbaryl | 5.0 |
| Methanol | 24.5 |

The composition as prepared formed a true solution. When diluted 1:99 with water, a true solution resulted.

EXAMPLE 7

The following compositions were prepared (amounts are parts by weight):

|  | A | B |
|---|---|---|
| Oxine | 4.1 | 4.1 |
| Copper hydrate | 1.4 | 1.4 |
| DDBSA | 65.0 | 65.0 |
| Malathion | 5.0 | — |
| Methyl parathion | — | 5.0 |
| Methanol | 24.5 | 24.5 |

Both compositions produced true solutions as prepared and when diluted 1:100 with water.

EXAMPLE 8

The following compositions, all dilutable for use with either water or petroleum hydrocarbon solvents, and diluted in the range of 1:9 to 1:19, provide excellent marine and land service protection to wood when impregnated into the wood at a 20–25 pcf retention.

|  | 1 | 2 | 3 | 4 | 5 | 6 | 7 | 8 |
|---|---|---|---|---|---|---|---|---|
| Oxine | 4 | 8 | 4.1 | 8.2 | 4.1 | 4.0 | 4.0 | 8.2 | 4 |
| Copper hydrate | 3 | 7 | 1.4 | 2.8 | — | — | — | 2.8 | 1 |
| DDBSA | 60 | 60 | 60.0 | 60.0 | 60.0 | 60.0 | 60.0 | 60.0 | 60 |
| Stannous Sulfate | — | — | — | — | 7.0 | 4.5 | 4.5 | — | . |
| Chlordane | 10 | — | — | — | — | 10.0 | — | — |
| Toxaphene | — | 5 | 5.0 | — | — | — | 6.0 | — |
| TBTO | — | — | — | — | — | — | — | 10.0 | 10 |
| Methanol | 23 | 20 | 29.5 | 29.0 | 28.9 | 21.5 | 25.5 | 19.0 | 24 |

EXAMPLE 9

The following antifouling compositions (to reduce barnacle and other marine organism encrustation of ship hulls), suitable as additives to marine hull coatings, were prepared. The amounts listed are parts by weight:

|  | 1 | 2 | 3 |
|---|---|---|---|
| Oxine | 9.0 | 9.0 | 15.0 |
| Copper hydrate | 7.0 | — | 10.0 |
| Stannous sulfate | — | 7.5 | — |
| DDBSA | 60.0 | 60.0 | 40.0 |
| Methanol | 24.0 | 23.5 | 35.0 |

These compositions can be incorporated in a number of marine coating formulations in amounts up to 15%. Conventional antifouling components, each as cuprous oxide, may be used to augment the protection against fouling organisms.

EXAMPLE 10

The following compositions form true solutions in water as prepared, and true solutions when diluted 1:100 with water.

|  | A | B | C | D |
|---|---|---|---|---|
| DDBSA | 60 | 60 | 60 | 60 |
| Chlordane | 5 | — | — | — |
| Toxaphene | — | 5 | — | — |
| Melathion | — | — | 5 | — |
| Methoxyclor | — | — | — | 5 |
| Methanol | 35 | 35 | 35 | 35 |

In general terms, the diphenyl, carbamate and chlorinated cyclo organic compound classes of insecticides function well in this invention. A number of insect control compounds in the organic phosphate class perform satisfactorily although stability time usually is reduced compared to the preceding classes.

SECTION 5

We have also discovered that the compositions of section 1 (comprising said antimicrobial agent and said disubstituted aryl compound) are useful for protecting various manufactured goods and industrial commodities from microbial attack or degradation. The compositions disclosed in section 1 exhibit broad spectrum antimocrobial efficacy against microorganisms which degrade materials of economic value. The range of activity and high per unit efficiency covers all classes of fungi and both Gram-positive and Gram-negative bacteria. Coupled with a number of auxiliary properties which have few undesirable side effects during application or in service, said compositions have unexpected and unique versatility for preservation of a wide range of materials and products. Heretofore available high-efficacy, broad-spectrum antimicrobial agents have one or more of a wide range of undesirable properties that can severely limit their utility. Among the frequently encountered limitations are mammalian toxicity, odor and color, skin and eye irritation, volatility and instability, low persistence, and narrow antimicrobial spectrum. The compositions of section 1 eliminate these and other bars to usage.

The combination of properties of said compositions meet the specialized needs of a broad and diverse range of material preservation applications, including both finished products and in-process manufacturing steps. Among the suitable uses providing one or more unique results, the following may be given as representative:

Leather—The compositions of section 1 have high substantivity to protein substrates, low toxicity, low irritation to human and animal tissues, and high antimicrobial efficacy against the fungal, and especially the bacterial, organisms that deteriorate leather.

Paints and adhesives—Water-based paints and adhesives require an antibacterial and antifungal agent for in-can preservation. Oil-based paints for exterior service frequently include antifungal agents. The compositions of section 1 possess an unusual degree of appropriate antifungal and antibacterial action relative to persistence of action after application. Heretoform antibacterial action has been limited to in-can prevention of product deterioration and to exterior service control of fungi that aesthetically disfigure paint and cause its deterioration.

Cutting oils and metal drawing compound—These water-based materials required antifungal and antibacterial protection to prevent rancidity, slime development, and possible growth of organisms pathogenic to man. The compositions of section 1 provide the needed broad spectrum antimicrobial activity with an unusual degree of safety to metal fabrication operating personnel.

Asphalt roofing—Both the asphalt and the cellulosic felt core in shingle and roll roofing are degraded by a variety of fungal species. The first major indication is product embrittlement which also is the standard criterion of roofing failure. The compositions of section 1 have unique utility by reason of high substantivity, resistance to water extraction, and heat resistance. Roofing is a severe long-term test of these properties.

Plastics—A substantial number of formulated polymers for a wide range of interior and exterior applications are subject to fungal deterioration and aesthetic disfigurement, from bathroom shower curtains to exterior building panels. The compositions of section 1 offer unusual heat stability for these uses.

Textiles and fiber products—These products, including rope, netting, yarns, twine and carpeting, and particularly those made from natural products such as cotton, hemp, linen and wool, generally are more susceptible to biological breakdown than the synthetics although the latter are not immune generally. Fungal deterioration is the most common, except in the case of wool which is highly subject to bacterial degradation. Protection from microorganism attack is difficult in severe service conditions because of the very rapid rate of product failure. The compositions of section 1 are uniquely suited for many such preservative uses because of high unit efficacy, low toxicity, low skin irritation, and resistance to actinic ray deactivation of antimicrobial efficacy.

Wood disinfection—Wood is employed in a number of applications involving direct (butcher blocks) and indirect (pallets) contact with a broad range of foodstuffs. The porosity of wood and other factors makes disinfection, often a mandatory requirement, very difficult. Complicating this problem is the need for safety and low odor, taste and color in the antimicrobial composition. The compositions of section 1 uniquely fit these needs and, in addition, provides uniformity of penetration into the substrate.

Water flood oil recovery—Bacteria introduced with water for secondary oil field recovery may proliferate, clogging porous oil sands and initiating corrosion of pipe and other equipment. The two most important organisms, *Desulfovibrio desulfuricans* and *Thiobacillus suboxydans,* are controlled with high efficacy by the compositions of section 1 which also provide the ecological safety that is desirable in this use because of the enormous quantities of water involved.

Petroleum fuels—A number of fungal genera, including Hormodendrum, and bacterial genera, including Pseudomonas, Bacillus and Aerobacter, grow abundantly at the water/oil interface of many petroleum fuels causing slime deformation and metallic corrosion. This may have especially grave consequences in critical fuel uses such as for jet aircraft engines. The high efficacy of the compositions of section 1 plus long-term antimicrobial stability is of substantial value for fuel preservation use.

Chemical toilets—The high efficacy of the compositions of section 1 plus low environmental contamination are of special value for such devices as planes, trains, boats, buses and campers, as well as in stationary uses, for chemical toilets.

Logs—Logs for lumber and paper conversion frequently are stored under water (water-sprayed piles or in ponds) for protection against fungal degradation. While generally useful, this procedure has limited value because high moisture content in the wood does not inhibit growth of many bacterial and certain soft-rot fungi, and because of the considerable difficulty, especially with water-sprayed piles of logs, in achieving all-over water/log contact. The compositions of section 1 are uniquely useful for addition to the water because they have the necessary high broad-spectrum efficacy and they are environmentally safe.

Breweries—The brewing of beer is a microbiological process with high susceptibility to ruinous results from even minor contamination with stray organisms of many types. The broad-spectrum, safe effectiveness of the compositions of section 1 provides unique equipment protection, and the persistence of antimicrobial activity is of great value in the dual area of fungal and bacterial control on walls, ceilings and floors in the vicinity of storage, processing and handling facilities.

SECTION 6

We have also discovered that the compositions of section 1 are useful for the treatment of mammalian diseases.

The compositions of section 1 are generally distinguished from the useful antimicrobials known to the prior art in that they exhibit a high efficacy against a broad and non-selective range of numerous types of microorganisms that are pathogenic to man and animals. These microorganisms include both Gram-positive and Gram-negative bacteria, the four primary classes of fungi (Ascomycets, Basidiomycetes, Phycomycetes and Fungi Imperfecti), yeasts envelope (lipoid) and naked (hydrophilic) viruses, protozoa and helminthes including mematoda and trematoda. Broad spectrum antimicrobials that are safe for human and animal use and have useful efficacy against Gram-positive and Gram-negative bacteria and fungi are relatively rare and essentially unknown in the field of antimicrobials.

Broad spectrum antimicrobials are highly significant in overgrowth control. Since various types of micro organisims compete with each other for survival, both inside and outside the mammalian body, many widely employed narrow-spectrum antimicrobials which control only selected organisims, provide an environment for the growth of other organisims. This is of notable concern to the medical profession in the widespread consumer use of medicated soaps and other preparations for the topical application in which, as a rule, the antimicrobial agents used in the preparations have practical effectiveness essentially only against Gram-positive bacteria. This can and does allow establishment and poliferation of Gram-negative bacterial and fungal pathogens not usually present on the skin, which organisms can be considerably more dangerous to the host than Gram-positive bacterial that are brought under control. By way of specific example, many of the common preparations will, with continued use, encourage the growth of the Gram-negative Pseudomonas sp., which is difficult to control even with antibiotics.

Many known antimicrobials for use in treating mammilian disease are also deficient in that they have relatively high toxicity and may have such high irritability to animal tissue as to render them practically of little use. These problems, particularly that of toxicity, are assuming particular importance in more recent times as various health and governmental agencies place increasingly stringent requirements on antimicrobials before permitting their use.

It has been found that the compositions of section 1 are efficacious against a broad and non-selective range of microorganisms that cause mammiliary disease, and are relatively nontoxic to mammals and have low irritation to mammal tissue. The compositions of section 1 are relatively low in color, odor and taste; have long stability under normal ambient conditions; have low volatility; are heat and light stable; can be diluted for use in many carriers; become insoluable and substantive to a host upon application; and are effective cleaning and wetting agents.

While it is believed necessary in the practice of this invention to form an initial solution of the antimicrobial agent with the disubstituted aryl compound (as these are defined in section 1) the antimicrobial agent may, when diluted for use, begin to form a very fine precipitate. This precipitation from solution may and usually will become complete after the composition has been applied to a substrate.

The compositions of section 1 eliminate overgrowth by reason of broad-spectrum control of all major types of microbiological flora. This range of activity is both microbiostatic and microbiocidal, in contrast to many present products which are effective primarily as biostats. The activity is both initial and residual, exhibiting both rapid initial organism kill or inhibition, depending upon the concentration of active ingredients employed, and considerable residual persistence of antimicrobial effectiveness.

The compositions of section 1 combine a number of auxiliary properties that not only are prerequisites for human and animal use, but which, in total, are unique in the field of antimicrobials. These include:

Low mammalian toxicity. The compositions of section 1 have much lower toxicity than the majority of anticicrobials in use today and have been given laboratory ratings of "not toxic orally."

Low skin and eye irritation. The range of skin and eye irritation is from low for concentrates to low to zero in dilute concentrations effective for use. Opthalmic preparations containing the compositions of section 1 for antimicrobial eye medication exhibit no eye irritation.

Low color, odor and taste. Concentrates of the compositions of section 1 exhibit a low inherent odor level, and impart minor to no color to most substrates. At suitable use dilutions, such compositions impart no color, no odor, and very low to zero taste. It therefore is generally practical in formulated products containing the compositions of section 1 to incorporate colorants, fragrances or masking agents, and taste flavoring agents as may be desired.

Shelf stability. No significant changes take place in antimicrobial properties in the composition of section 1 even after long storage periods under normal ambient conditions.

Low volatility. Use dilutions of the compositions of section 1 maintain initial efficacy upon standing in open containers for long time periods. Evaporation of carriers, usually water, will increase efficacy by raising the ratio of composition to carrier in the use of dilution A number of presently used antimicrobials require special use precautions because of volatility or sublimation processes.

High air, heat and light stability. In contrast to a number of present products, the compositions of section 1 exhibit no deterioration or loss of efficacy from prolonged exposure to air or light. Heat stability up to an estimated 300° F. allows a range of use conditions not feasible with many currently available antimicrobials. Heat plus inherent antimicrobial action of the compositions provide a flexibility of use and performance unmatched by any narrow-spectrum antimicrobials. This increased flexibility is particularly useful in that no special equipment is needed for utilization to offset volatility, light or air instability, active ingredient sublimation or the like.

Carrier versatility. While water is the most widely used and versatile use diluent for antimicrobials, the compositions of section 1 may be carried in a very broad range of polar (including water) and non-polar solvents, and combinations thereof. Carriers other than water may be very useful in a variety of end uses for a number of reasons including enhanced antimicrobial action, need for rapid carrier evaporation, general unsuitability of water, need for low or non-volatility of the carrier, the desire for carrier lubricity or emolliency, the adverse effect of water upon the host organism or substrate and the like. Suitable carriers include a broad range of hydrocarbons, alcohols, ketones, ethers, glycols, chlorinated organic solvents, esters, acetyls, phtalates, adipates, aldehydes, anhydrides, acids, silicone fluids, nitroparaffins plus a variety of the more exotic solvents such as N-vinyl-2-pyrrolindone, dimethyl sulfoxide and dimethyl formamide. This carrier versatility is in sharp contrast with most antimicrobials which are either incompatible with, or are insoluble in, many types of carriers.

Insolubility after application. For general use, the preferred embodiment of compositions of section 1 are soluble in the use-dilution carriers. Such ready-for-use compositions, notably in a water carrier, become water-insoluble after application to the host. This is in sharp contrast to most antimicrobials which retain water solubility after application. This feature offers obvious residual persistence advantages since removal by aqueous media is a major means by which initial effectiveness of antimicrobial agents is rapidly diminished.

Substantivity The compositions of section 1 not only turn water insoluble rapidly after application as just mentioned, but also exhibit strikingly high affinity for a number of surfaces, most notably cellulosic and proteinaceous substrates. This is true under usual parameters of use. It normally occurs near-instantly and in the wet condition. The result for a number of uses is unusually high retention of antimicrobial action yielding surprisingly long efficacy life.

Wetting-cleaning action. The compositions of section 1 possess strong, inherent wetting and detergent activity. This feature is a significant aid in penetrating crevices and areas of difficult access. Further, the high detergent-cleaning action is an important adjunct for many medical antisepsis and disinfection applications.

Efficaceous in the presence of organic matter. Unlike many antimicrobial compositions such as a number of the quaternary amines, the efficacy of the compositions of section 1 are not destroyed by the presence of organic material.

The following is an incomplete, but representative listing of uses for the compositions of section 1 which uses are unique in kind or degree of effectiveness. A feature common to these uses is effective control of an uncommonly large number of the major classes of pahogens as previously described. This feature has primary importance where kill or inactivation is mandatory and in uses where non-selective control of all organisms is desirable to prevent overgrowth of pathogenic flora otherwise not controlled by selective-spectrum antimicrobials. Such overgrowth can be both rapid and dangerous.

Surgical antiseptics. The compositions of section 1 provide extremely high skin degerming capacity as measured by reduction in the transient and resident flora count as shown in Example. It is believed that, in addition to the demonstrated high antimicrobial efficacy, the compositions of section 1 may have exceptional capacity to act upon the difficult to reach flora under the outer, cutaneous layer of skin which consists of the flat plaques of keratin. In view of the generally held belief that total degerming is not possible short of destruction of the skin itself, the greater the reduction of flora, the lower the risk of the patient from a surgeon who is compelled to operate with hands that cannot be fully disinfected and to make incisions through skin that cannot be made entirely germ-free. The exceptional flora count reduction afforded on the skin by the compositions of section 1 is unexpected in view of the long known difficulty of the skin degerming and the acknowledged fact that, as the count reduction approaches the theoretical 100% maximum, the problems of achieving even a very small incremental improvement in the count becomes progressively more difficult by orders of magnitude.

Another reason for desiring to achieve the highest reduction in skin count that is feasible, both on the surgical team and the patient, is the fact that surgical gowns, gloves, patient draping, folds in the skin, the perineal and umbilicus areas and the like provide both protection and favorable (warm and moist) conditions for rapid and accelerated growth of the remaining organisms. Hence the high order of initial flora reduction, and the substantivity and persistence of antimicrobial activity of the compositions, has important utility when consideration is given to the fact that containment of the rapid regrowth generally is very difficult. For instance, perforation of gloves worn by the surgical team is a frequent occurrence with numbers as high as 70% being reported. With glove punctures or tears, flora ladened sweat and the like may leak large numbers of micro organisms into a surgical wound.

The ultimate in degerming effectiveness of the composition is obtained by means of an after-application of the composition following the surgical scrub or patient preoperative skin preparation. This may be a rinse in a water solution of the composition, or an alcoholic tincture, or most effective of all, an ointment carefully rubbed into the skin, under the fingernails and into protective folds of the skin and mucous membranes. For the hands of operating personnel, an ointment which leaves the hands non-slippery can be readily formulated. Not only does such an ointment or cream present physical barrier of sorts to the movement of microflora, but much more importantly, a finite layer of the highly toxic composition is interposed between the organisms remaining after the degerming step and the surgical wound or any other area of the patient and surgical personnel subject to pathogenic contamination.

Where desired, the compounds clean as well as disinfect. The cleaning action can be applied to unbroken skin, wounds and body cavities.

Disinfection of medical and surgical materials. The compositions of section 1 are suitable for disinfection of critical items, such as scalpel blades, transfer forceps and cardiac catheters; semi-critical items such as thermometers, aspirator tubes and cystoscopes; and noncritical items such as face masks, rebreathing bags and a variety of accessory items.

The broad antimicrobial spectrum of the compositions coupled with ready adaptability to the use of heat, and compatibility with water carriers and mixtures with higher solvents such as propylene glycol, provides unique high level disinfection of critical items. Items of lesser criticality are disinfected rapidly in the cold.

Dental antisepsis and disinfection. Hot and cold disinfection and sterilization of instruments and a broad range of other items is practical with the compositions of section 1. For scrub-up of oral surgery personnel the just preceding procedures are highly effective. The compositions of section 1 exhibit particularly useful efficacy for the frequent daily hand washings required of dental personnel between patients and for routine procedures.

The oral cavity harbors large microbial polulations which are most difficult to control. Limited and general oral antisepsis, particularly for prevention of post-treatment infections, is effectively accomplished with the compositions of section 1.

Disease control. The broad spectrum antimicrobial activity of the compositions of section 1 make these uniquely suitable for a wide range of pathogenic conditions including mastitis in lactating females, bacterial and fungal hemorrhoidal conditions; ringworm; vulvovaginal candidiasis; athlete's foot; oral moniliasis; mycotic skin infections with casual agents that include *Candida albicans,* Trichophyton sp., *Epidermaphyton floccosum, Microsporus canis* and *Microsporum audouini;* Trichomonal and non-specific vaginitis, urinary infections; hair and scalp conditions; a variety of nemotodal and tremotodal conditions.

Contraception. The compositions of this invention are spermicidal.

Specialty water disinfection. The compositions of section 1 find utility in therapeutic baths and various water soaking treatments.

Environmental control of fungal allergies. A substantial portion of human allergic conditions is caused by a wide range of molds and mildews which infest homes, living quarters and other habitated buildings. Such allergies can be alleviated by control of the fungal organisms. To be effective, antifungal application must be made to all surfaces and articles including walls, floors, ceilings, craw spaces and basements, furniture, drapes and carpets, mattresses and pillows.

The compositions of section 1 have the necessary prerequisites for such application, e.g., no color or odor, low taste, and no damage to or unacceptable residue on treated surfaces: These requirements are combined with extremely high fungistatic and fungicidal efficacy. Such antifungal treatment can be coupled in a number of cases with cleaning, leaving a substantive and persistent residue on carpets, upholstery, walls, floors, tiles and other surfaces.

Pharmaceutical, toiletry and cosmetic product preservation. The compositions of section 1 possess near-ideal properties for these uses, including very high microbiological activity against the representative organisims that cause product deterioration and disease to the user such as *Staphylococcus aureus, Escherichia coli, Candida albicans, Pseudomonas aeruginosa* and *Aspergillis niger* spores. Control of the latter generally is difficult to achieve. Control of *Ps. aeruginosa* also is difficult and of considerable importance because this organism causes pathogenic conditions in man and animals, against which antibotic treatment is relatively ineffective. Control of Pseudomonas is particularly important in critical products such as opthalmic preparations. *Ps. aeruginosa*, which few antimicrobials control reliably, is considered by some authorities to be the most troublesome as well as the most ubiquitous.

Skin odor control. The compositions of section 1 offer unique performance in this area. Skin odor, bacterial in origin, generally is caused by resident Gram-positive skin flora picked up in sweat containing nutrients for rapid bacterial growth. Presently available antimicrobials to underarm and foot deodorants, medicated soaps and the like, are relatively effective against these offensive odor-producing organisms, but generally are ineffective against a variety of other organisms that, while not necessarily causing disagreeable odor, are dangerous to man, especially if given the earlier described opportunity to proliferate in the relative absence of Gram-positive bacteria. This is especially true of the Gram-negative Pseudomonas and to a lesser extent *Candida albicans*. Present antimicrobials capable of overall broad spectrum control are not suitable for wide consumer use for a number of reasons including toxicity, odor, color, skin sensivity or irritation. Indeed many have been banned by governmental agencies except for perscription use.

The compositions of section 1 have a prerequisite safety and other features needed for broad consumer usage. These compositions uniquely provide a balance of antimicrobial activity that prevents overgrowth of uncontrolled organisms. Entirely unexpectedly, perhaps due to their substantive nature, the compositions exhibit skin odor control for much longer periods than present products.

Even more unexpected is the long term odor protection provided by residual action only. When the formulated compositions are applied with water, and dried, no odor will develop for much longer periods than present underarm deodorants allow.

Medicated, deodorant soaps are in wide use for bathing. Used regularly, these provide a significant degree of body odor control, although the magnitude of control is considerably less than that afforded by underarm deodorants. Further the more effective medicants, such as hexachlorophene, have been banned for general use. Bathing with formulated compositions of section 1 provide cleaning power equal to the best of current products and, quite remarkably, provide sole control of body and skin odor for much longer periods of time than present medicated soaps for underarm and foot deodorant preparations, medicated vaginal douches, and medicated hair shampoos.

It would appear that the after-application water insolubility of the compositions and high substantivity to skin has a significant role in the demonstrated long term odor control. The insolubility/substantivity factor is much greater than might be expected in view of the extreme severity of the service conditions.

General bathing with formulated compositions of the invention also provides control of the ubiquitous conditions known at athlete's foot, jock itch, vaginitis and other assorted skin and mucuous membrane conditions.

Our discoveries are illustrated by the following compositions:

EXAMPLE 1

The following composition was prepared and tested for skin substantivity:

| Oxine | 4.1 | parts by weight |
|---|---|---|
| Copper hydrate | 1.4 | " |
| DDBSA | 65.0 | " |
| Propylene glycol | 29.5 | " |

Ten parts by weight of this composition was blended (heated at 140° F. with constant agitation) with:

| Oleyl alcohol ethoxylate (20 EO) | 15 | parts by weight |
|---|---|---|
| Lauryl alcohol ethoxylate (25 EO) | 25 | " |
| Octyl phenol ethoxylate (9 EO) | 5 | " |
| Acetylated lanolin | 2 | " |
| Distilled water | 43 | " |

The resulting formulation was a transparent pale yellow-green, medium viscosity liquid. One gram was used to wash the hands. After water rinsing and drying the hands, a drop of 1% dithio oxamide copper indicator was applied to various parts of the hands. Immediate development of a black color indicated presence of copper (in Cu-8-Q) on the skin. Using Ivory soap, the hands were washed, rinsed and dried twice more. The black color remained, requiring several days to disappear.

This formulation was an effective hand cleaner, exhibited no skin irritation and left the skin with a residual soft, smooth feel. Used for bathing and as a hair shampoo, the formulation exhibited the same results.

EXAMPLE 2

The final formulation of the preceding Example was used to wash the entire body, including the scalp and hair. No skin odor developed until the middle of the fourth day. Commercially available underarm deodorants (two brands) previously tested by three subjects, following a bath with a commonly used medicated bar soap, failed to stop odor development for even 24 hours.

EXAMPLE 3

The following composition was prepared and evaluated for underarm odor control:

| Oxine | 2.05 | parts by weight |
|---|---|---|
| Copper hydrate | 0.70 | " |
| DDBSA | 40.00 | " |
| Propylene glycol | 57.25 | " |

Three parts of this composition was blended as before with:

| Propylene glycol | 5 | parts by weight |
|---|---|---|
| Glycerin | 5 | " |
| Ethanol | 5 | " |
| Water | 82 | " |

Four test subjects applied this final formulation under one arm and a brand name underarm deodorant under the other arm. Total odor control ranged from a minimum of 3½ days to almost 6 days for the test subjects whereas none of the three brand name comparative control deodorants provided complete odor control for a full 24 hours.

Essentially the same odor control results were obtained using the following formulation in ointment form:

Two parts of the foregoing composition were blended with:

| | |
|---|---|
| Oleyl alcohol ethoxylate (20 EO) | 18 |
| Lauryl alcohol ethoxylate (25 mol) | 9 |
| Acetylated lanolin | 1 |
| Glycerin | 9 |
| Propylene glycol | 4 |
| Polyvinyl pyrrolidone, 60% in water | 1 |
| Distilled water | 56 |

No underarm irritation was noted by any test subject, although one test subject had a history of irritation problems with a number of brand name products.

EXAMPLE 4

The second formulation in the preceding Example was applied once daily by eight test subjects to the skin between the toes for control of "Athlete's Foot". The condition was brought largely under control and definite signs of skin healing were exhibited in all cases by the end of 24 hours. Two of the cases had previously resisted control with several over-the-counter brand name antifungals. One of the two, a virulent infection, had reached the bleeding stage from deeply cracked skin and a bacterial infection started, despite twice daily application for eight days of a 1% solution of Toluaftate which has gained broad recognition for effective control of "Athlete's Foot". The Toluaftate product not only failed to control the case of "Athlete's Foot" but also the ensuing bacterial infection. The test formulation brought both the fungal and bacterial infections under control in 24 hours.

The casual organisms of this last fungal infection almost certainly were not those defined medically as causing "Athlete's Foot", but rather one or more other fungi which to the layman (but not a dermatologist) produces similar or identical symptoms and hence is called "Athlete's Foot". The Tolunaftate failed in that its narrow-spectrum antifungal activity had no effect upon the causal organisms in the test case and because it has no significant antibacterial efficacy. Very few "Athlete's Foot" preparations provide even a low order of antibacterial activity.

The compositions of the invention, therefore, offer not only potent control of true "Athlete's Foot" but also of a wide range of fungal and sometimes resulting bacterial conditions which to the public is "Athlete's Foot". The importance of the major improvement over existing technology is the fact that in the vast majority of cases the public, not a dermatologist, makes the diagnosis and determines the treatment.

EXAMPLE 5

Hemorrhoids, varicose veins of the rectum, are suffered by an estimated 40% to 50% of the adult population. Prescriptions and over-the-counter preparations, ointments and suppositories, are in wide, almost universal use for alleviation of these widespread symptoms of hemorrhoids: (1) bleeding from the rectum, (2) bacterial infection which can cause inflammation of tissues and pain and (3) fungal infection (caused by organisms related to "Athlete's Foot" and ringworm causal agents) which brings about itching at times can be near-intolerable.

Present state-of-the-art hemorrhoidal preparations contain an antimicrobial in a soothing, emollient ointment base; some also contain a topical anesthetic for pain control. The antimicrobial is designed to serve a dual purpose: (a) to allow healing, thereby controlling rectal bleeding, bacterial infection and pain and (b) to control itching. These objectives are difficult ones to achieve because of present unavailability of sufficiently potent yet safe antimicrobials, and because of the great difficulty of obtaining effective antimicrobial action in the inevitable presence of large amounts of organic matter.

The first formulation of the preceding Example was applied for hemorrhoid symptom control. Rapid and more effective relief of symptoms resulted, as compared to commercially available products. In one instance involving almost daily rectal bleeding for over six years despite daily use of a brand name product, the test formulation brought about complete cessation of bleeding within 24 hours for almost three months with no further application of the test formulation. At first resumption of bleeding, application of the test formulation again controlled all bleeding and weekly to bi-weekly application thereafter for the next six months prevented all further bleeding.

The broad-spectrum efficacy of the compositions of the invention as demonstrated by the in-vivo and in-vitro data herein, and in my copending application referred to above, provide results of a magnitude not heretofore available for treatment of pathogenic conditions of man and animals, and for health related applications. The ideal antimicrobial is highly and rapidly toxic to the target organisms and non-toxic to the host organisms and possesses to a high degree the desirable prerequisites of low taste, odor, high stability and the like. The compositions of the invention come closer to the theoretical ideal than anything heretofore known by a margin ranging from significantly better to almost infinitely superior.

EXAMPLE 6

The following composition was tested for minimum fungicidal concentration and compared to two well known antifungal chemicals—pentachlorophenol and 2,3,5 trichloro-4-propyl-sulfonyl pyridine—and DDBSA.

| | |
|---|---|
| Oxine | 8.2 parts by weight |
| Copper hydrate | 2.8 parts by weight |
| DDBSA | 59.0 parts by weight |
| Propylene glycol methyl ether | 30.0 parts by weight |

All of the test composition concentrations to be tested were incorporated in the fungal growth media (agar) in accordance with standard microbiological practices. Agar plugs containing the test fungicides then were inoculated with a sporulating culture and inoculated at the temperatures and times specified by The American Type Culture Collection (ATCC) recommendations. The plugs were then scored for absence or presence of organism growth. The results are shown in the following table. Minimum fungicidal concentrations were determined against a broad spectrum of fungi that are detrimental to man, foodstuffs and materials and which can result in metabolite formations (mycotoxins) of extreme toxicity to man and animals.

In the table below, Composition A is that of this Example 25 and the active ingredient is Cu-8-Q; Composition B is DDBSA; Composition C is pentachlorophenol; and Composition D is 2,3,5-trichloro-4-propylsulfonyl pyridine. Where no concentration is listed, no details available. The stated value of "1" means 1 or fewer ppm.

| | Minimum Fungicidal Concentration (ppm of active ingredient) | | | |
|---|---|---|---|---|
| | A | B | C | D |
| *Aspergillis niger* (ATCC 9642) | 1 | 10,000 | 1–3 | — |
| *Aspergillis terreus* (ATCC 10609) | 1 | 100 | — | 36 |
| *Aspergillis flavus* (ATCC 11655) | 1 | 1,000 | 22–54 | — |
| *Alternaria alternata* (ATCC 13963) | 1 | — | — | — |
| *Aureobasidium pullulans* (ATCC 16624) | 1 | 100 | — | — |
| *Lenzites trabea* (ATCC 11539) | 1 | 100 | 1–3 | — |
| *Polyporus tulipiferae* (ATCC 11245) | 1 | 100 | 1–3 | — |
| *Penicillium brevi compactum* (ATCC 16024) | 1 | 100 | — | — |
| *Rhizopus stolonifer* (ATCC 24794) | 1 | 100 | 1–3 | — |
| *Trichoderma viride* (ATCC 8678) | 10 | 100 | — | — |
| *Trichoderma sp.* (ATCC 12668) | 1 | 100 | — | — |
| *Candida albicans* (ATCC 10259) | 1 | 1,000 | — | 3 |

These results illustrate the high efficacy of the composition of this invention and confirm the fact that an antifungal composition prepared from a Cu-8-Q/DDBSA solution is much superior to DDBSA alone. The results also indicate the favorable relative efficacy of the test composition compared to the two commercially available fungicides of recognized high performance.

EXAMPLE 7

Using the standard AOAC fungicidal test method (12th Edition, 1975), the composition below was evaluated against two widespread fungi.

| Oxine | 2.08 parts by weight |
|---|---|
| Copper hydrate | 0.70 parts by weight |
| DDBSA | 40.00 parts by weight |
| Isopropanol | 32.00 parts by weight |
| Demineralized water | 25.22 parts by weight |

The two fungi were *Aspergillis niger*, a ubiquitous black fungus which flourishes on a broad range of substrates, and *Trichophyton mentagrophytes*, a cause of "athlete's foot."

*A. niger*—at 1:200 use dilution in a water carrier, no growth after 10 minutes' exposure.

*T. mentagrophytes*—at 1:750 use dilution in a water carrier, no growth after 10 minutes' exposure.

Simular but somewhat lower efficacy results were obtained by substituting zinc-8-Q or aluminum-8-Q in the composition of this example, produced by reacting zinc oxide and aluminum hydroxide respectively with oxine.

EXAMPLE 8

The DDBSA/Cu-8-Q solution of Example 7 diluted 1:400 in a water carrier, was applied by spray nine times, at two-week intervals, to peach and nectarine cultivars during the growing season. The results against brown rot (*Monolinia fructocola*), compared to nontreated trees, is presented below.

| | % Fruit Affected | |
|---|---|---|
| | Peach | Nectarine |
| At harvest (treated) | 1 | 3 |
| At harvest (untreated) | 15 | 43 |
| Five days later (treated) | 3 | 6 |
| Five days later (untreated) | 60 | 67 |

EXAMPLE 9

The DDBSA/Cu-8-Q solution of Example 7 was tested in vitro against a major turf pathogen, *Helminthosporium vagans*, via a standard agar plate culture technique, with these results:

| | Fungus Colony Diameter |
|---|---|
| 1:6700 use dilution in water carrier | 1 mm |
| 1:3350 use dilution in water carrier | 0 |
| Control | 21 mm |

The results demonstrate very high efficacy in controlling this important pathogen. Complete control of *H. vagans* was achieved in this assay between 3.7 and 7.5 ppm of Cu-8-Q.

As illustrated in the examples to follow, the compositions of this invention have high efficacy against a broad spectrum of bacteria that are pathogenic to mammals and plant life, that contribute to reduced water quality, that cause deterioration of foodstuffs, that degrade a broad range of manufactured and natural materials and products, and which generate toxic metabolites (bacteria-toxins) that are among the most poisonous substances known to man.

Of particular interest is high efficacy against Gramnegative as well as Gram-positive microorganisms. Few antibacterial materials now available are effective against the Gram-negatives and still fewer provide economical control of them. A number of available antibacterials toxic to Gram-negative organisms have practical limitations which severely restrict use, including high mammalian toxicity, phytotoxicity, corrosiveness to skin and a variety of materials, strong odor, strong color, high volatility, low or erratic shelf stability, low or nonexistent residual activity, and prohibition of use at elevated temperatures.

The basic significance in the need for Gram-negative control lies in the fact that this bacterial category includes a number of widespread, virulent pathogens which are difficult to impossible to control with presently available antibiotics, notably Pseudomonas sp. typified by *Pseudomonas aeruginosa* PRD-10, the standard strain in the United States for evaluation of antibacterials for mandatory Gram-negative control applications.

The compositions herein disclosed eliminate or substantially reduce these use limitations inherent in many other germicides. The compositions are quite unique in having strong Gram-positive and Gram-negative activity combined with broad versatility of formulation and use plus a high degree of safety (low toxicity and zero to low skin and eye irritation). Add to this the high efficacy, broad spectrum antifungal activity of the compositions of this invention and the resulting range of toxicity to target organisms and safety to man, the most sensitive of hosts, is unique indeed.

The balance of toxicity provided by this invention to Gram-positive, Gram-negative and fungal microorganisms has special value in the broad consumer field of skin deodorancy. Present antibacterials suffer from the fact that they are effective primarily against gram-positives, allowing Gram-negative and fungi overgrowth, a condition considered dangerous by many authorities.

EXAMPLE 10

The DDBSA/Cu-8-Q solution of Example 6 was tested, along with a number of well known antimicrobial agents, against a broad spectrum screen of economically important Gram-positive and Gram-negative bacteria. All antimicrobial agents were incorporated in the agar bacterial growth media according to standard microbiological practices. The bacterial species were grown in nutrient broth; 24-hour cultures, the inoculum, then were streaked onto the nutrient agar plates containing the test antimicrobials. After a 24-hour incubation at the appropriate temperature, the plates were rated for presence or absence of bacterial growth.

Minimum bactericidal concentrations for each of the tested agents are stated in the following tabulation of results in parts per million (ppm) of active ingredient as defined in the description of each agent.

| Bacteria (ATCC No.) | Antimicrobial Agent (ppm* of active ingredient) | | | | | | |
|---|---|---|---|---|---|---|---|
| | A | B | C | D | E | F | G |
| Gram-positive: | | | | | | | |
| Bacillus cereus | 1 | 100 | — | 7 | 8 | 5–10 | — |
| Bacillus lichenforms (27326) | 1 | 100 | — | 7 | 8 | 2–5 | — |
| Bacillus megaterium (27327) | 1 | 100 | — | 7 | 8 | — | — |
| Bacillus subtilis (37328) | 1 | 100 | — | 750 | 8 | — | 3 |
| Micrococcus flavus (10240) | 1 | 100 | — | 7 | 8 | — | — |
| Mycobacterium phlei (15610) | 1 | 10 | — | 7 | 8 | — | 3 |
| Staphylococcus aureus (6538) | 1 | 100 | 2083 | 7 | 8 | 1–3 | 3 |
| Gram-negative: | | | | | | | |
| Alcaligenes faecalis (337) | 10 | 1000 | — | 750 | 80 | — | — |
| Alcaligenes marshalii (21030) | 104 | 100 | — | 7 | 8 | — | — |
| Escherichia coli (11229) | 104 | 10,000 | — | 750 | 80 | 250–500 | 165 |
| Flavobacterium arboresceus (4358) | 10 | 10 | 4166 | 7 | 8 | — | — |
| Klebsiella pneumoniae (4356) | 10 | 10,000 | — | 750 | 8 | — | — |
| Proteus vulgaris | 10 | 1000 | — | 750 | 800 | — | — |
| Pseudomonas aeruginosa (15442) | 104 | 1000 | 4166 | 750 | 800 | 1000–2500 | 165 |
| Salmonella cholerasuis (10708) | 104 | 1000 | — | 750 | 80 | 250–500 | 165 |
| Salmonella typhi (6539) | 104 | 1000 | 2083 | 750 | 80 | — | 165 |

*stated value of "1" means 1 or less
A = the DDBSA/Cu—8-Q solution of Example 6 with the active ingredient expressed in terms of Cu—8-Q.
B = DDBSA.
C = phenol
D = Betadine, an iodine/polyvinylpyrrolidone complex containing 0.75% iodine. The active ingredient is iodine.
E = Alkyl dimethyl ammonium chlorides (61% $C_{12}$, 23% $C_{14}$, 11% $C_{16}$ and 3% $C_{10}$).
F = sodium pentachlorophenate
G = 2,3,5-trichloro-4-propylsulfonyl pyridine.
See previous list of antimicrobial agensts These data demonstrate the high efficacy of the composition of Example 6. On the basis of the average of the efficacies against all the test organisms, Composition A is 45 times superior to Composition B; 88 times better than Composition C; 10.7 times better than Composition D; and 3.5 times superior to Composition E.

On the basis of the average of the efficacies against the three test bacteria (*Staphylococcus aureus, Salmonella cholerasuis* and *Pseudomonas aeruginosa* PRD-10) required by the Environmental Protection Agency of a "hospital grade" Composition A is 10 times better than Composition B; 7.2 times better than Composition D; and 1.6 times better than Composition E.

EXAMPLE 10A

The composition set forth below was prepared by previously described procedures:

| | |
|---|---|
| Oxine | 2.08 parts by weight |
| Copper hydrate | 0.70 parts by weight |
| Isopropanol | 32.00 parts by weight |
| DDBSA | 40.00 parts by weight |
| Water (demineralized) | 25.22 parts by weight |

When evaluated as a bactericide by the AOAC Use Dilution Method (12th Edition, 1975), 10 ring carriers per organism, the following results were obtained (A=-subculture and B=resubculture):

| | Use Dilution | Negative | Positive |
|---|---|---|---|

| in Water Carrier | | A | B | A | B |
|---|---|---|---|---|---|
| Staphylococcus aureus | 1:1000 | 10 | 10 | 0 | 0 |
| Salmonella cholerasuis (PRD-10) | 1:1000 | 10 | 10 | 0 | 0 |
| Pseudomonas aeruginosa | 1:400 | 10 | 10 | 0 | 0 |

-continued

| | Use Dilution in Water Carrier | Negative | | Positive | |
|---|---|---|---|---|---|
| | | A | B | A | B |
| *Aerobacter aerogenes* | 1:400 | 10 | 10 | 0 | 0 |

A ten-minute kill is required against the first three pathogens for sale as a hospital grade disinfectant. Efficacy against the fourth organism, a major cause of slime in recirculated cooling water systems and pulp and paper mills, demonstrates utility of the composition as a slimicide.

EXAMPLE 11

This composition was prepared and tested at one use dilution, 1:50 in water carrier, against the causal agent of potato ring rot bacteria (*Corynebacterium sepedonicum*):

| Oxine | 2.08 parts by weight |
|---|---|
| Copper hydrate | 0.70 parts by weight |
| DDBSA | 40.00 parts by weight |
| Triton X-100 | 20.00 parts by weight |
| Isopropanol | 22.00 parts by weight |
| Water (demineralized) | 15.22 parts by weight |

Infected potato seed readily contaminate potato seed cutters, sacks, bins, cellars, trucks and planting equipment with the highly infectious ring rot bacteria. The result may be infected potato plants, tubers and reduced yields.

The test procedure consisted of dipping unpainted, planed wood laths (6") into a slurry of infected ring rot tuber tissue, allowing excess slurry to drain off (3-5 minutes) and then spraying the contaminated lath with the test antibacterials. Three to five minutes later, healthy Norgold Russet potato seed pieces were rubbed vigorously against both sides of the contaminated and antibacterial-treated laths. The process was repeated using laths not contaminated with *C. sepedonicum* but treated with the test antibacterial agent. The rubbed seed pieces were stored in bags and later planted at the appropriate time.

In addition to the composition of the invention, untreated controls, 20% Clorox (1.05% sodium hypochlorite in water), formaldehyde (37% formalin diluted 1:120 in water) and Roccal (benzalkonium chloride or zephiran chloride) diluted with water to 800 ppm concentration were tested. The results of the test are tabulated below and refer to plants and tubers produced from the tubbed test seed pieces.

| Antimicrobial | Ring Rot Contaminated | % Plant Stored | % Ring Rot Plants | % Ring Rot Tubers | Yield cwt/acre |
|---|---|---|---|---|---|
| None (control) | Yes | 98 | 23 | 8 | 493 |
| None (control) | No | 95 | 0 | 0 | 609 |
| DDBSA/Cu—8-Q | Yes | 98 | 0 | 2 | 631 |
| DDBSA/Cu—8-Q | No | 100 | 0 | 0 | 602 |
| 20% Clorox | Yes | 98 | 20 | 9 | 500 |
| 20% Clorox | No | 98 | 0 | 0 | 602 |
| Roccal | Yes | 98 | 20 | 9 | 515 |
| Roccal | No | 98 | 0 | 0 | 638 |

The composition of this example demonstrates superior control of the ring rot bacterium. Other species of the genus Corynebacterium are causal agents of disease in man and a variety of plant life.

EXAMPLE 12

The composition below was prepared and tested for speed and range of antibacterial activity, in the absence and presence of organic matter (blood) for use in hospital disinfection, cold sterilization and antisepsis.

| Oxine | 4.1 parts by weight |
|---|---|
| Copper hydrate | 1.4 parts by weight |
| DDBSA | 65.0 parts by weight |
| Propylene glycol methyl ether | 29.5 parts by weight |

Many antimicrobial agents are partially or totally deactivated in the presence of organic matter, constituting a severe limitation to effectiveness of such agents for a number of uses such as wound antisepsis and medical instrumentation and surface disinfection where large amounts of organic matter often are encountered and sometimes are unavoidable.

The AOAC Use Dilution Confirmation Test (12th Edition, 1970) was modified as follows:

(a) The test temperature was 37° C.

(b) The ring carriers were soaked in sheep blood for two hours, air-dried for one hour, then contaminated with the test pathogen.

(c) The contaminated rings were contacted with the test antibacterial agent for 30-second, one-minute and three-minute periods.

The results are set forth in the following table, in which:

| Test Pathogen | Use Dilution in Water Carrier | In Absence of Blood | | | In Presence of Blood | | |
|---|---|---|---|---|---|---|---|
| | | 30 sec. | 1 min. | 3 min. | 30 sec. | 1 min. | 3 min. |
| *Staphylococcus aureus* | Undiluted | 0 | 0 | 0 | 0 | 0 | 0 |
| (ATCC 6538) | 1:10 | 0 | 0 | 0 | 0 | 0 | 0 |
| | 1:100 | 0 | 0 | 0 | 3 | 6 | 3 |
| *Salmonella typhi* | Undiluted | 0 | 0 | 0 | 0 | 0 | 0 |
| (ATCC 6539) | 1:10 | 0 | 0 | 0 | 0 | 0 | 0 |
| | 1:00 | 0 | 0 | 0 | 0 | 0 | 0 |
| *Pseudomonas aeruginosa* | Undiluted | 0 | 0 | 0 | 0 | 0 | 0 |
| (ATCC 15442) | 1:10 | 0 | 0 | 0 | 10 | 10 | 0 |

| Test Pathogen | Use Dilution in Water Carrier | In Absence of Blood | | | In Presence of Blood | | |
|---|---|---|---|---|---|---|---|
| | | 30 sec. | 1 min. | 3 min. | 30 sec. | 1 min. | 3 min. |
| | 1:100 | 0 | 0 | 0 | 10 | 3 | 3 |

0 = no growth in 10 of 10 tubes tested
1 = growth in 1 of 10 tubes tested
2 = growth in 2 of 10 tubes tested
3 = growth in 3 of 10 tubes tested
etc.

These results indicate that the test composition is capable of rapid antibacterial action in the presence of substantial amounts of organic matter against the three human pathogens generally considered as definitive for antibacterial efficacy evaluation.

EXAMPLE 13

The composition of Example 7 was prepared for evaluation as a skin degerming agent against resident and transient flora. Six subjects were tested using the Modified Prices Multiple Basin Technique which measures reduction of skin flora as a percentage of that achieved by washing the hands with unmedicated soap. Bacterial counts were taken from the first, fourth and fifth basins. The counts from the first basin represent the transient bacterial flora and that of the fourth and fifth basins the resident flora. Prior to the test, none of the subjects used a medicated soap for one week.

The results set forth in the following table demonstrate a very high order of efficacy for the test composition for critical degerming uses such as a surgical scrub for operating room personnel and skin preparation at the surgical site.

| Subject | Basin | Unmedicated Soap Average No. of Organisms/Basin | Test Composition Average No. of Organisms/Basin | % Reduction |
|---|---|---|---|---|
| 1 | 1 | 2,500,000 | 60,000 | 97.6 |
| | 4 | 1,900,000 | 25,000 | 98.7 |
| | 5 | 1,300,000 | 15,000 | 98.8 |
| 2 | 1 | 1,700,000 | 30,000 | 98.2 |
| | 4 | 1,100,000 | 20,000 | 98.2 |
| | 5 | 800,000 | 1,000 | 99.9 |
| 3 | 1 | 800,000 | 40,000 | 95.0 |
| | 4 | 600,000 | 20,000 | 96.7 |
| | 5 | 500,000 | 1,000 | 99.8 |
| 4 | 1 | 2,000,000 | 50,000 | 97.5 |
| | 4 | 1,000,000 | 1,000 | 99.9 |
| | 5 | 800,000 | 1,000 | 99.9 |
| 5 | 1 | 1,500,000 | 40,000 | 97.3 |
| | 4 | 800,000 | 1,000 | 99.9 |
| | 5 | 500,000 | 1,000 | 99.8 |
| 6 | 1 | 1,900,000 | 50,000 | 97.4 |
| | 4 | 800,000 | 15,000 | 98.1 |
| | 5 | 520,000 | 1,000 | 99.8 |

EXAMPLE 14

| | |
|---|---|
| Oxine | 2.08 |
| Copper hydrate | 0.70 |
| Nonyl phenol/EO surfactant* | 20.00 |
| DDBSA | 45.00 |
| Isopropanol | 15.00 |
| Water (distilled) | 17.22 |

(*1 mol nonyl phenol to 6 mols ethylene oxide)

The above composition was prepared by the procedure already described and evaluated for efficacy against ciliated protozoan and two types of viruses.

Hemaglutination Assays

| Virus | HA Titre | | |
|---|---|---|---|
| | Untreated | Treated (1:50)* | Treated (1:200) |
| Adenovirus | 128 | 0 | 0 |
| Newcastle Disease virus | 512 | 0 | 0 |

(*1:50 and 1:200 use dilutions of composition in a water carrier in contact with virus suspensions for 15 minutes)

The HA titre is a measure of the number of infectious virus particles present in the test suspension.

Plaque Assays

Via the same procedure as above, the untreated virus suspensions contained $6.4 \times 10^4$ pfu/ml of Adenovirus virus particles and $21 \times 10^5$ pfu/ml Newcastle Disease virus particles respectively. After treatment with the 1:50 and 1:200 use dilutions, readings of 0 pfu/ml were obtained. Each pfu represents one infectious virus particle. A zero pfu reading represents total inactivation of the infectious virus.

Protozoan Inhibition

Inhibition of growth of ciliated protozoan (Tetrahymena) in pond water was obtained at a 6 ppm concentration (based on Cu-8-Q) of the above test composition of DDBSA and Cu-8-Q after 6-hour and 72-hour contacttimes. The 6 ppm reading represents the MIC (Minimum Inhibitory Concentration). These results demonstrate high efficacy of the test composition against the test microorganisms.

SECTION 7

We have also discovered that the compositions of section 1 are useful for controlling plant disease by contacting plants with such compositions. More particularly, this embodiment of our invention relates to the control of plant disease and more particularly to the use of certain antimicrobial agents that are comparatively non-toxic to animal and plant life but are highly efficacious against fungal, bacterial and other classes of pathogens, including viruses and nematodes, which microorganisms are important casual agents of disease in a broad spectrum of plant life.

We have found that the compositions of section 1 exhibit a wide range of utility against fungal, bacterial and other classes of pathogens, including viruses and nematodes, which are important casual agents of diseases in a broad spectrum of plant life. Such plant life includes field and horticultural crops, ornamentals and grasses. The mode of use includes foliar, seed, dormant season and, in some instances soil treatment. It also includes treatments designed to preserve the plant product in the post-harvest period, which treatment may be carried out both pre- and post-harvest.

The disclosed compositions present an unusual combination of properties that are unexpectedly unique for control of a broad range of diseases of a large number of plant species, including:

Anti fungal control. The spectrum of activity in the use of compositions of this invention covers the four classes of fungi—Ascomycetes, Basidiomycetes, Phycomycetes and Fungi Imperfecti.

Antibacterial control. The use of compositions of this invention covers a broad spectrum of Gram-positive and Gram-negative plant pathogens.

Antiviral and Antinematodal control. The use of compositions of this invention is effective against viruses and a substantial selection of nematode species.

High antimicrobial efficacy. Minimum inhibition and minimum kill concentrations of the compositions of this invention are very low.

Low phytotoxicity. Generally, but not always, the use of the compounds of this invention have low phytotoxicity at adequate use.

Water solubility. Concentrates prepared for use in this invention may be use-diluted in a variety of polar and non-polar carriers, including water which is the most versatile. Diluted with water, the concentrates generally form true solutions that in most cases provide substantial handling, mixing-for-use, application and uniformity-of-coverage advantages over the typical water-insoluble products. In some cases of use-dilution, stable and often colloidal emulsions are formed. These generally provide the same advantages as true solutions.

Water insolubility. On application to the host organism (or the soil), the compositions of this invention turn insoluble in water in most instances, which increases antimicrobial persistence of activity and results in increased rain wash off resistance.

Substantivity. When applied to a number of substrates, the compositions of this invention become tightly affixed (substantive) and consequently exhibit substantial resistance to removal by rain or other factors.

Heat and sunlight stability. The compositions of this invention exhibit high stability to heat (to cover 200° F.) and light, particularly ultraviolet.

Safety. Acute oral mammalin toxicity of the highest practical concentrations of the compositions of this invention is moderately low, about halfway between aspirin and common table salt. Typical use dilutions thereof, 1:100 to 1:1000 in water, are non-toxic.

Skin and eye irritation properties of typical use-dilutions range from very low to zero. Highest practical concentrates of the compositions exhibit moderately high skin and eye irritation. At one-tenth of maximum concentration, use-dilutable in the 1:10 to 1:100 range, the compositions are inocuous to the skin and show low eye irritation.

The toxicity characteristics of the compositions exhibit two unusual and unique features of considerable practical value. First, biodegradation in most instances reduces the initially low mammalian toxicity, as applied to the host plant or soil, up to about 95% in a few weeks after application without a corresponding reduction in residual antimicrobial efficacy. Second, death in the event of accidental ingestion of a lethal dose of the compositions is a secondary and reversible mechanism wherein the time period for initiation of medical treatment is non-critical. Medical treatments for this condition are well-known and are generally successful with no adverse after effects.

High uniformity of coverage. Appropriate use-dilutions of the compositions of this invention exhibit pronounced substrate wetting and spreading properties which provides a high degree of uniformity of coverage of the host plant.

Ease and economy of handling and application. The compositions of this invention generally are concentrated, readily pourable liquids which are easily and rapidly misible with water for use to form either true solutions or colloidal emulsions, as diluted for use, they are easy to apply with no settling out of active ingredients. Due to the high product concentration, a minimum of product need be transported, handled and stored and disposal of containers is minimized.

In the plant world, bacterial diseases are in the minority relative to fungal diseases. Surprisingly, very few products are available for bacterial disease control. This is in sharp contrast with the very large availability of products for fungal diseases. The antibacterials now available have quite limited utility because of either low efficacy or high cost. Compositions of the invention exhibit considerable antibacterial promise for plant use by reason of high unit efficacy and low cost.

The method of use and efficacy of the compositions of this invention are illustrated in the following examples.

EXAMPLES

Example 1

The following composition was prepared and tested as a rice seed treatment:

| | | |
|---|---|---|
| Oxine | 2.05 | parts by weight |
| Copper hydrate | 0.70 | " |
| DDBSA | 40.00 | " |
| Octyl phenol ethoxylate (9EO) | 20.00 | " |
| Isoporpanol | 20.00 | " |
| Water | 17.25 | " |

This composition was placed in water (800 cc per cwt. of seed) and used to coat the inside walls of a container. Weighed seed samples were placed in the container which was rotated for 15 minutes to transfer the test composition to the seed. The treated seed was stored until planted. This application procedure was repeated for application of several commercially available antifungal products.

Treated and untreated control seed was planted in thirteen locations in four states using both water-planting and drill-planting methods. The effectiveness of all tested products in increasing the seedling emergence rate is shown below as a consolidation of results from all test plots.

| | (1) Application Rate | (2) Improvement over Control (%) | (3) Performance Consistency | (4) Range of Improvement % | |
|---|---|---|---|---|---|
| | | | | High | Low |
| EXAMPLE 2 | 4* | 18.3 | 36.2 | plus 38 | plus 2 |
| PRODUCT A | 4 | 27.4 | 80.4 | plus 56 | minus 2 |
| PRODUCT B | 4 | 16.6 | 63.1 | plus 61 | minus 2 |
| PRODUCT C | 4 | 12.6 | 47.8 | plus 32 | minus 16 |
| PRODUCT | 4 | 12.3 | 71.3 | plus 37 | minus 35 |

-continued

| (1) Application Rate | (2) Improvement over Control (%) | (3) Performance Consistency | (4) Range of Improvement % High Low |
|---|---|---|---|
| D | | | |

(1) Ounces per 100 lbs. (cwt.) of rice aged of the chemical active ingredient in all instances except Example 2 which is given in terms of the total composition.
*contains 0.1 ounce of Cu—8-Q.
(2) Percentage increase in seedling emergence rate as compared to that of the untreated control seed in the thirteen test plots.
(3) These numbers express the difference between the highest and lowest percent change in seedling emergence rate for each test product compared to the untreated seed results in the thirteen test plots. Thus, the lower the number, the greater is the test-to-test consistancy of emergence rate improvement provided by the test product.
(4) This column lists the best (high) of the thirteen test results and the poorest (low). "Plus" represents imporvement over untreated control seed emergence rate whereas "minus" represents a reduction therein.
Product A - a coordination product of zinc ion and manganese ethylene bisdithiocarbamate.
Product B - copper hydroxide formulated as a finely divided flowable composition.
Product C - cis-N—(1, 1, 2, 2-tetrachloroethylthio)-4-cyclohexene-1,2-dicarboximide.
Product D - 5,6-dihydro-2-methyl-1,4-oxathiim-3-carboxanilide.

The estimated costs of Products A through D range from 3 to 5 times higher than that of the composition of Example 2.

Example 2

The following composition was tested for minimum fungicidal concentration and compared to two well known antifungal chemicals—pentachlorophenol and 2,3,5trichloro-4-propyl-sulfonyl pyridine—and DDBSA.

| | |
|---|---|
| Oxine | 8.2 parts by weight |
| Copper hydrate | 2.8 parts by weight |
| DDBSA | 59.0 parts by weight |
| Propylene glycol methyl ether | 30.0 parts by weight |

All of the test composition concentrations to be tested were incorporated in the fungal growth media (agar) in accordance with standard microbiological practices. Agar plugs containing the test fungicides then were inoculated with a sporulating culture and inoculated at the temperatures and times specified by The American Type Culture Collection (ATCC) recommendations. The plugs were then scored for absence or presence of organism growth. The results are shown in the following table. Minimum fungicidal concentrations were determined against a broad spectrum of fungi that are detrimental to man, foodstuffs and materials and which can result in metabolite formations (mycotoxins) of extreme toxicity to man and animals.

In the table below, Composition A is that of this Example 2 and the active ingredient is Cu-8-Q; Composition B is DDSBA; Composition C is pentachlorophenol; and Composition D is 2,3,5-trichloro-4-propylsulfonyl pyridine. Where no concentration is listed, no details available. The stated value of "1" means 1 or fewer ppm.

| | Minimum Fungicidal Concentration (ppm of active ingredient) | | | |
|---|---|---|---|---|
| | A | B | C | D |
| Aspergillis niger (ATCC 9642) | 1 | 10,000 | 1-3 | — |
| Aspergillis terreus (ATCC 10609) | 1 | 100 | — | 36 |
| Aspergillis flavus (ATCC 11655) | 1 | 1,000 | 22-54 | — |
| Alternaria alternata (ATCC 13963) | 1 | — | — | — |
| Aureobasidium pullulans (ATCC 16624) | 1 | 100 | — | — |
| Lenzites trabea (ATCC 11539) | 1 | 100 | 1-3 | — |
| Polyporus tulipiferae (ATCC 11245) | 1 | 100 | 1-3 | — |
| Penicillium brevi compactum (ATCC 16024) | 1 | 100 | — | — |
| Rhizopus stolonifer (ATCC 24794) | 1 | 100 | 1-3 | — |
| Trichoderma viride (ATCC 8678) | 10 | 100 | — | — |
| Trichoderma sp. (ATCC 12668) | 1 | 100 | — | — |
| Candida albicans (ATCC 10259) | 1 | 1,000 | — | 3 |

These results illustrate the high efficacy of the composition of this invention and confirm the fact that an antifungal composition prepared from a Cu-8-Q/DDBSA solution is much superior to DDBSA alone. The results also indicate the favorable relative efficacy of the test composition compared to the two commercially available fungicides of recognized high performance.

Example 3

The compositions of this invention exhibit efficacy against a broad spectrum fungal plant pathogens, as illustrated by various use dilutions in a water carrier of the following composition:

| | |
|---|---|
| Copper hydrate | 1.70 parts by weight |
| 8-hydroxy quinoline | 4.44 parts by weight |
| Isopropanol | 35.00 parts by weight |
| DDBSA | 58.86 parts by weight |

A. Valencia Oranges

Tested on harvested fruit against Phomopsis stem-end rot and Diplodis rot, at a 1:100 use dilution, 2-minute dip application. After 3 weeks at 70° F., the following percentages of decay were noted:
Control (untreated)oranges—9.5% decay
Treated oranges—5.3% decay B. Sugar Cane An agar seeding test against Ceratocystis paradoxa (pineapple disease) at a 1:10,000 (100 ppm) use dilution yielded a 3.0 mm. inhibition zone.

C. Peach Trees

Tested against Taphrina deformans (causes leaf curl disease). Four test trees were sprayed twice, two weeks apart, with a 1:400 use dilution. Three months later, 100 leaves on each test tree were rated for leaf curl:
Control (untreated) leaves—100% leaf curl
Treated leaves—13.5% leaf curl D. Cotton Effectiveness against 11 fungi and 1 bacterium (Xanthomonas malvacearum) that are associated with disease of cottonseed, seedlings and other plants was evaluated in vitro, using the following compositions:

| Composition #1 | Copper hydrate | 1.70 parts by weight |
| | 8-hydroxy quinoline | 4.44 parts by weight |
| | Methanol | 4.00 parts by weight |
| | Isopropanol | 30.86 parts by weight |
| | DDBSA | 59.00 parts by weight |
| Composition #2 | Copper hydrate | 2.80 parts by weight |
| | 8-hydroxy quinoline | 8.20 parts by weight |
| | Methanol | 4.00 parts by weight |
| | Isopropanol | 26.00 parts by weight |
| | DDBSA | 59.00 parts by weight |

Both compositions were prepared in accordance with procedures stated in previous examples.

The following results were obtained, expressed in parts per million (ppm) of total test composition in water carrier and the relative growth inhibition provided at each test strength on each tested organism. In the tables below:

| | contractions (ppm) | | | | | |
|---|---|---|---|---|---|---|
| Test Organisms | 0 | 1 | 5 | 25 | 100 | 500 | 1000 |
| | Composition #1 | | | | | | |
| *Pythium ultimum* (41B) | 0 | 0 | 0 | 1 | 2 | 3 | 3 |
| *Rizoctonia solani* (1D) | 0 | 0 | 0 | 1 | 2 | 3 | 3 |
| *Fusarium* (4A) | 0 | 0 | 0 | 3 | 3 | 3 | 3 |
| *Fusarium* (4D) | 0 | 1 | 1 | 2 | 2 | 2 | 3 |
| *Fusarium roseum* (4C) | 0 | 0 | 0 | 1 | 2 | 2 | 3 |
| *Colletotrichum gossypii* (35A) | 0 | 0 | 0 | 1 | 2 | 2 | 2 |
| *Xanthomonas malvecearum* (2A) | 0 | 0 | 0 | 0 | 2 | 2 | 3 |
| | Composition #2 | | | | | | |
| *Pythium ultimum* (41B) | 0 | 0 | 1 | 2 | 2 | 2 | 2 |
| *Rhizoctonia solani* (1D) | 0 | 0 | 1 | 2 | 2 | 2 | 2 |
| *Fusarium* (4A) | 0 | 0 | 1 | 1 | 1 | 2 | 2 |
| *Fusarium* (4D) | 0 | 0 | 1 | 1 | 2 | 2 | 2 |
| *Fusarium roseum* (4C) | 0 | 0 | 0 | 2 | 2 | 2 | 2 |
| *Colletotrichum gossypii* (35A) | 0 | 0 | 0 | 2 | 2 | 2 | 2 |
| *Xanthomonas malvecearum* (2A) | 0 | 0 | 0 | 1 | 1 | 2 | 2 |
| | Composition #1 | | | | | | |
| Aspergillis sp. | | | | | | 1 | 1 |
| *Helminthosporium oryzae* | | | | | | 2 | 2 |
| Mucor mucedo | | | | | | 1 | 1 |
| Penicillium sp. | | | | | | 1 | 1 |
| Rhizopus sp. | | | | | | 1 | 1 |

0 = no apparent inhibition
1 = some inhibition
2 = considerable inhibition (little growth
3 = total inhibition (no growth)

Example 4

The following composition was screened for fungal pathogen response as a foliar spray on beans and rice.

| Oxine | 2.08 parts by weight |
|---|---|
| Copper hydrate | 0.70 parts by weight |
| DDBSA | 40.00 parts by weight |
| Isopropanol | 32.00 parts by weight |
| Demineralized water | 25.22 parts by weight |

The rating scale is from 0 (no pathogen control) to 10 (complete pathegon control). The concentration of active ingredient (in a water carrier) of all compositions tested is 33 parts per million (ppm). The active ingredient in the composition of Example 4 is expressed in terms of Cu-8-Q and the chemical as listed below for four comparative products. The comparative products tested wre Karathane (2,4-dinitro-6-(2-octyl phenyl crotonate). Vitavax (5,6-dihydro-2-methyl-1,4-oxathiin-3-carboxanilide), Daconil (tetrachloroisophthalonitrile) and Maneb (manganese ethylenebisdithiocarbamate). The plants and diseases tested were bean mildew (*Erysiphe polygoni*), bean rust (*Uromyces phaseoli typica*) and rice spot (*Helminthosporium orazae* and *Cerocospora orazae*).

| | Bean Mildew | Bean Rust | Rice Spot |
|---|---|---|---|
| Example 28 composition | 8 | 10 | 10 |
| Karathane | 10 | — | — |
| Vitavax | — | 9 | — |
| Daconil | — | — | 10 |
| Maneb | — | — | 8 |

Example 5

The following composition was evaluated (diluted with water for use) in vitro for inhibition against two fungal pathogens, Botrytis sp. and Alternaria sp., causal agents of a variety of plant diseases.

| Oxine | 2.08 parts by weight |
|---|---|
| Copper hydrate | 0.70 parts by weight |
| DDBSA | 40.00 parts by weight |
| Triton X-100 | 20.00 parts by weight |
| Isopropanol | 22.00 parts by weight |
| Water (demineralized) | 15.22 parts by weight |

The zone of inhibition agar plate test also was used to test Cunilate 2174 (diluted in mineral spirits for use) for comparison. The composition concentrations in the table of results below are expressed in parts per million (ppm) of Cu-8-Q. The larger the inhibition zone, the greater is the efficacy of the composition.

| | Botrytis | | | Alternaria | | |
|---|---|---|---|---|---|---|
| DDBSA—Cu—8-Q | | | | | | |
| Concentration (ppm) | 21 | 50 | 125 | 21 | 50 | 125 |
| Inhibition zone (mm) | 13 | 15 | 22 | 0 | 16 | 21 |
| Cunilate 2174 | | | | | | |
| Concentration (ppm) | 83 | 200 | 500 | 83 | 200 | 500 |
| Inhibition zone (mm) | 13 | 14 | 16 | 0 | 0 | 14 |

The DDBSA/Cu-8-Q solution of this invention exhibits an improvement in efficacy against the tested organisms by a factor of 4× in the case of Botrytis to 10× in the case of Alternaria.

Example 6

The DDBSA/Cu-8-Q solution of the preceding example (31), diluted 1:400 in a water carrier, was applied by spray nine times, at two-week intervals, to peach and nectarine cultivars during the growing season. The results against brown rot (*Monolinia fructocola*), compared to nontreated trees, is presented below.

| | % Fruit Affected | |
|---|---|---|
| | Peach | Nectarine |
| At harvest (treated) | 1 | 3 |
| At harvest (untreated) | 15 | 43 |
| Five days later (treated) | 3 | 6 |
| Five days later (untreated) | 60 | 67 |

Example 7

The DDBSA/Cu-8-Q solution of Example 6 was tested in vitro against a major turf pathogen, *Helminthosporium vagans,* via a standard agar plate culture technique, with these results:

|  | Fungus Colony Diameter |
| --- | --- |
| 1:6700 use dilution in water carrier | 1 mm |
| 1:3350 use dilution in water carrier | 0 |
| Control | 21 mm |

The results demonstrate very high efficacy in controlling this important pathogen. Complete control of *H. vagans* was achieved in this assay between 3.7 and 7.5 ppm of Cu-8-Q.

As illustrated in the examples to follow, the compositions of this invention have high efficacy against a broad spectrum of bacteria that are pathogenic to mammals and plant life, that contribute to reduced water quality, that cause deterioration of foodstuffs, that degrade a broad range of manufactured and natural materials and products, and which generate toxic metabolites (bacteria-toxins) that are among the most poisonous substances known to man.

Of particular interest is high efficacy against Gram-negative as well as Gram-positive microorganisms. Few antibacterial materials now available are effective against the Gram-negatives and still fewer provide economical control of them. A number of available antibacterials toxic to Gram-negative organisms have practical limitations which severely restrict use, including high mammalian toxicity, phytotoxicity, corrosiveness to skin and a variety of materials, strong odor, strong color, high volatility, low or erratic shelf stability, low or nonexistent residual activity, and prohibition of use at elevated temperatures.

The basic significance in the need for Gram-negative control lies in the fact that this bacterial category includes a number of widespread, virulent pathogens which are difficult to impossible to control with presently available antibiotics, notably Pseudomonas sp. typified by *Pseudomonas aeruginosa* PRD-10, the standard strain in the United States for evaluation of antibacterials for mandatory Gram-negative control applications.

The composition herein disclosed eliminate or substantially reduce these use limitations inherent in many other germicides. The compositions are quite unique in having strong Gram-positive and Gram-negative activity combined with broad versatility of formulation and use plus a high degree of safety (low toxicity and zero to low skin and eye irritation). Add to this the high efficacy, broad spectrum antifungal activity of the compositions of this invention and the resulting range of toxicity to target organisms and safety to man, the most sensitive of hosts, is unique indeed.

The balance of toxicity provided by this invention to Gram-positive, Gram-negative and fungal microorganisms has special value in the broad consumer field of skin deodorancy. Present antibacterials suffer from the fact that they are effective primarily against Gram-positives, allowing Gram-negative and fungi overgrowth, a condition considered dangerous by many authorities.

Example 8

The DDBSA/Cu-8-Q solution of Example 2 was tested, along with a number of well known antimicrobial agents, against a broad spectrum screen of economically important Gram-positive and Gram-negative bacteria. All antimicrobial agents were incorporated in the agar bacterial growth media according to standard microbiological practices. The bacterial species were grown in nutrient broth; 24-hour cultures, the inoculum, then were streaked onto the nutrient agar plates containing the test antimicrobials. After a 24-hour incubation at the appropriate temperature, the plates were rated for presence or absence of bacterial growth.

Minimum bactericidal concentrations for each of the tested agents are stated in the following tabulation of results in parts per million (ppm) of active ingredient as defined in the description of each agent.

| Bacteria (ATCC No.) | Antimicrobial Agent (ppm* of active ingredient) | | | | | | |
| --- | --- | --- | --- | --- | --- | --- | --- |
|  | A | B | C | D | E | F | G |
| Gram-positive: | | | | | | | |
| *Bacillus cereus* | 1 | 100 | — | 7 | 8 | 5–10 | — |
| *Bacillus lichenforms* (27326) | 1 | 100 | — | 7 | 8 | 2–5 | — |
| *Bacillus megaterium* (27327) | 1 | 100 | — | 7 | 8 | — | — |
| *Bacillus subtilis* (37328) | 1 | 100 | — | 750 | 8 | — | 3 |
| *Micrococcus flavus* (10240) | 1 | 100 | — | 7 | 8 | — | — |
| *Mycobacterium phlei* (15610) | 1 | 10 | — | 7 | 8 | — | 3 |
| *Staphylococcus aureus* (6538) | 1 | 100 | 2083 | 7 | 8 | 1–3 | 3 |
| Gram-negative: | | | | | | | |
| *Alcaligenes faecalis* (337) | 10 | 1000 | — | 750 | 80 | — | — |
| *Alcaligenes marshalii* (21030) | 104 | 100 | — | 7 | 8 | — | — |
| *Esherichia coli* (11229) | 104 | 10,000 | — | 750 | 80 | 250–500 | 165 |
| *Flavobacterium arboresceus* (4358) | 10 | 10 | 4166 | 7 | 8 | — | — |
| *Klebsiella pneumonia* (4356) | 10 | 10,000 | — | 750 | 8 | — | — |
| *Proteus vulgaris* | 10 | 1000 | — | 750 | 800 | — | — |
| *Pseudomonas aeruginosa* (15442) | 104 | 1000 | 4166 | 750 | 800 | 1000–2500 | 165 |

-continued

| Bacteria (ATCC No.) | Antimicrobial Agent (ppm* of active ingredient) | | | | | | |
|---|---|---|---|---|---|---|---|
| | A | B | C | D | E | F | G |
| Salmonella cholerasuis (10708) | 104 | 1000 | — | 750 | 80 | 250–500 | 165 |
| Salmonella typhi (6539) | 104 | 1000 | 2083 | 750 | 80 | — | 165 |

*stated value of "1" means 1 or less
A = the DDBSA/Cu—8-Q solution of Example 2 with the active ingredient expressed in terms of Cu—8-Q.
B = DDBSA.
C = phenol
D = Betadine, an iodine/polyvinylpyrrolidone complex containing 0.75% iodine. The active ingredient is iodine.
E = Alkyl dimethyl ammonium chlorides (61% $C_{12}$, 23% $C_{14}$, 11% $C_{16}$ and 3% $C_{10}$).
F = sodium pentachlorophenate
G = 2,3,5-trichloro-4-propylsulfonyl pyridine.
See page 115 for list of antimicrobial agents These data demonstrate the high efficacy of the composition of Example 2. On the basis of the average of the efficacies against all the test organisms. Composition A is 45 times superior to Composition B; 88 times better than Composition C; 10.7 times better than Composition D; and 3.5 times superior to Composition E.

On the basis of the average of the efficacies against the three test bacteria (Staphylococcus aureus, Salmonella cholerasuis and Pseudomonas aeruginosa PRD-10) required by the Environmental Protection Agency of a "hospital grade" disinfectant, Composition A is 0.10 times better than Composition B; 7.2 times better than Composition D; and 1.6 times better than Composition E.

Example 9

The composition set forth below was prepared by previously described procedures:

| | | |
|---|---|---|
| Oxine | 2.08 | parts by weight |
| Copper hydrate | 0.70 | parts by weight |
| Isopropanol | 32.00 | parts by weight |
| DDBSA | 40.00 | parts by weight |
| Water (demineralized) | 25.22 | parts by weight |

When evaluated as a bactericide by the AOAC Use Dilution Method (12th Edition, 1975), 10 ring carriers per organism, the following results were obtained (A=subculture and B=resubculture):

| | Use Dilution in Water Carrier | Negative | | Positive | |
|---|---|---|---|---|---|
| | | A | B | A | B |
| Staphylococcus aureus | 1:1000 | 10 | 10 | 0 | 0 |
| Salmonella cholerasuis (PRD-10) | 1:1000 | 10 | 10 | 0 | 0 |
| Pseudomonas aeruginosa | 1:400 | 10 | 10 | 0 | 0 |
| Aerobacter aerogenes | 1:400 | 10 | 10 | 0 | 0 |

A ten-minute kill is required against the first three pathogens for sale as a hospital grade disinfectant. Efficacy against the fourth organism, a major cause of slime in recirculated cooling water systems and pulp and paper mills, demonstrates utility of the composition as a slimicide.

Example 10

This composition was prepared and tested at one use dilution, 1:50 in water carrier, against the causal agent of potato ring rot bacteria (Corynebacterium sepedonicum):

| | | |
|---|---|---|
| Oxine | 2.08 | parts by weight |
| Copper hydrate | 0.70 | parts by weight |
| DDBSA | 40.00 | parts by weight |
| Triton X-100 | 20.00 | parts by weight |
| Isopropanol | 22.00 | parts by weight |
| Water (demineralized) | 15.22 | parts by weight |

Infected potato seed readily contaminate potato seed cutters, sacks, bins, cellars, trucks and planting equipment with the highly infectious ring rot bacteria. The result may be infected potato plants, tubers and reduced yields.

The test procedure consisted of dipping unpainted, planed wood laths (6") into a slurry of infected ring rot tuber tissue, allowing excess slurry to drain off (3–5 minutes) and then spraying the contaminated lath with the test antibacterials. Three to five minutes later, healthy Norgold Russet potato seed pieces were rubbed vigorously against both sides of the contaminated and antibacterial-treated laths. The process was repeated using laths not contaminated with C. sepedonicum but treated with the test antibacterial agent. The rubbed seed pieces were stored in bags and later planted at the appropriate time.

In addition to the composition of the invention, untreated controls, 20% Clorox (1.05% sodium hypochlorite in water), formaldehyde (37% formalin diluted 1:120 in water) and Toccal (benzalkonium chloride or zephiran chloride) diluted with water to 800 ppm concentration were tested. The results of the test are tabulated below and refer to plants and tubers produced from the tubbed test seed pieces.

| Antimicrobial | Ring Rot Contaminated | % Plant Stored | % Ring Rot Plants | % Ring Rot Tubers | Yield cwt/acre |
|---|---|---|---|---|---|
| None (control) | Yes | 98 | 23 | 8 | 493 |
| None (control) | No | 95 | 0 | 0 | 609 |
| DDBSA/Cu—8-Q | Yes | 98 | 0 | 2 | 631 |
| DDBSA/Cu—8-Q | No | 100 | 0 | 0 | 602 |
| 20% Clorox | Yes | 98 | 20 | 9 | 500 |
| 20% Clorox | No | 98 | 0 | 0 | 602 |
| Roccal | Yes | 98 | 20 | 9 | 515 |

-continued

| Antimicrobial | Ring Rot Contaminated | % Plant Stored | % Ring Rot Plants | % Ring Rot Tubers | Yield cwt/acre |
|---|---|---|---|---|---|
| Roccal | No | 98 | 0 | 0 | 638 |

The composition of this example demonstrates superior control of the ring rot bacterium. Other species of the genus Corynebacterium are casual agents of disease in man and a variety of plant life.

SECTION 8

According to another embodiment of our invention we have found that wood can be preserved by treating the wood, using standard technques such as dipping or pressure impregnation, with a composition as set forth in section 2 (hereinafter referred to as "the compositions of this invention").

DESCRIPTION OF THE PRIOR ART

Essentially, three different classes of compounds are currently being used for the preservation of wood. These include chlorinated phenols, such as pentachlorophenol(PCP), mixed metal salts such as those containing copper, chromium and arsenic (CCA salts), and petroleum distillation by products such as creosote. These preservatives may be applied to the surface of the wood such as by dipping or brushing or, in more severe applications where long service life is required such as with telephone poles, railroad ties, marine pilings, mine timbers and the like, pressure impregnation processes are frequently used.

Basically, pressure impregnation processes are classified as either "full-cell" or "empty-cell" processes. The essential difference between the two processes lies in the fact that in the full-cell process, the liquid forced into the wood is retained by the wood after impregnation. In contrast to this, in the empty-cell process, most of the treatment fluid is expelled from the wood after impregnation. The terms "full" and "empty" derive from the fact that the cells of the wood are substantially filled with impregnants in the full-cell process, but tend only to be coated with the impregnant in the empty-cell process.

The full-cell process makes use of a vacuum/pressure impregnant cycle in which the wood is first placed under vacuum and then, without admitting air, the treatment vessel is filled with the treatment liquid. After the wood is fully immersed in the liquid, the pressure is increased to perhaps ten atmospheres or so and the liquid is forced into the wood. After the wood has been treated to refusal, or until a predetermined gross absorption of the treatment liquid has been achieved, the pressure is relieved and the treatment fluid is drained from the vessel. Usually a short vacuum cycle follows to remove excess fluid from the surface of the wood.

The distinctive feature of the empty-cell process is that it does not make use of an initial vacuum, but rather, as most commonly and preferably practiced, the wood is placed under pressure prior to the time that it is contacted with the treatment liquid. The initial pressure is maintained during the time the treatment vessel is filled with the treatment liquid, and then the pressure is increased to a second higher pressure, forcing the treatment liquid into the wood against the air pressure initially established within the wood. As a result, when the pressure is relieved, the air compressed within the wood expels much of the liquid that was forced into the wood. This expelled liquid is referred to as the "kickback". Commonly, as is the case with the full-cell treatment, a vacuum is pulled in the treatment vessel after the impregnation pressure has been relieved to increase the recovery of the treatment liquid and shorten the period of time in which liquid will drip from the surface of the wood.

The empty-cell process is especially advantageous as compared with the full-cell process when treating wood with water-borne materials since the wood, after treatment, is ready for economic shipment, further treatment, or immediate use since there is no large quantity of water which must be removed as by kiln or air drying.

Numerous disadvantages attach to the use of the most commonly used wood preservation materials, not the least among them being the more recently recognized dangers to the environment and to persons and animal life that come in contact with the treated wood. Governmental tolerance for the PCP, CCA salts and creosote treatment materials only exists due to the complete absence of any alternative preservation material of proven effectiveness to take their place. The standard treatment materials also suffer, to varying degrees and depending upon the particular one used, in that they sometimes are leached from the wood in service, they are not as highly absorbed by the wood as may be desired, uniformity of retention within the wood is variable, elevated impregnation temperatures for purposes of efficiency can sometimes not be used, deposition of some of the materials causes embrittlement of the wood, and green lumber cannot be impregnated unless it is first dried.

SUMMARY OF THE INVENTION

Accordingly, it is a principal object of this invention to provide a method for the preservation of wood in which the wood is treated with an antimicrobial material that is effective in preserving the wood and is comparatively nontoxic toward animal and plant life.

Another object of this invention is to provide a method for the preservation of wood with a comparatively nontoxic but effective antimicrobial that will become affixed or substantive to the wood. Another object of this invention is to provide a method whereby wood can be treated with a preservative that is comparatively nontoxic and can be applied utilizing standard treatment techniques including dipping, brushing, and full-cell and empty-cell pressure processes.

Another object of this invention is to provide a method for treating wood with a preservative in which the preservative becomes affixed to the wood, the uniformity of retention is improved, embrittlement of the wood is avoided, elevated temperatures can be used during treatment, diffusion of the preservative into green lumber can be achieved, the danger of working with toxic chemicals can be avoided, and higher gross obsorptions and uniformity of retention can be improved.

Briefly, these and other objects of this invention are achieved by contacting wood with a solution comprised of an antimicrobial agent that is dissolved in a disubstituted aryl compound having an oleophilic and a hydrophilic substituent. In a preferred embodiment of this invention, for example, the antimicrobial agent can be an organometallic complex such as a metal chelate of 8-hydroxy-quinoline and the disubstituted aryl compound can be an alkyl benzene acid such as a commercial grade of DDBSA.

Use of the herein disclosed wood preservative solutions find considerable utility in the method of this invention by improving significantly on some of the defects and encountered with the commonly available wood treatment materials now in general use, such as PCP, CCA salts and creosote. In somewhat more detail than as briefly mentioned above, these improvements over the prior art include the following:

The compositions of this invention, when applied to wood, have a high degree of fixation to the wood. Although the preservative compositions as applied to or impregnated into the wood are solutions, many of the compositions, including those based on a metal chelate of oxine, become water-insoluble after application and drying and become highly fixed or substantive to the wood the result is that they are resistant to removal even under severe water leaching procedures.

It is known in the wood technology that when nonpolar solvent carriers, such as petroleum oils are used, these carriers penetrate the wood more quickly and provide higher retention and deeper penetration into wood than preservatives utilizing polar carriers or solvents, such as water. The reason for the considerably greater flow rate of nonpolar liquids is not understood, but one proposed explanation is that polar liquids, like water, form strong hydrogen bonds which create frictional drag between the wood and the liquid during flow through the pores of the wood. At wood moisture contents below the fiber saturation point (about 30% water on a dry wood base), flow rates of preservatives in water carriers are reduced up to 50% as compared to petroleum oils as reported in typical studies that have been published. Additional published studies of water-borne preservatives indicate that a number of these in 0.5% concentrations in water exhibit average retention reductions of up to 57% compared to the retention of water alone when wood is treated via full-cell pressure procedures. It has also been indicated that the addition of a surface active wetting agent to water or water-borne preservatives does not provide a to be expected increase in flow rate through the wood. In point of fact, the flow rate is reduced when surfactants are used. It has been proposed that by reducing the surface tention of the water, the rate at which the wood is swelled by the water becomes more rapid, with an attendant reduction in the size of the pores or passage through which the water must flow. Unlike some of the compositions of the prior art, those of this invention do not behave in accordance with the above observations or theory of flow. The subject water-borne compositions penetrate wood more rapidly, not less rapidly, than do oil-borne preservatives, and yield higher retention in the wood using any given method of application to the wood involving significant contacttimes between the wood and the preservation solution.

The preservatives of this invention provide for greater uniformity of retention. Wood is a natural material which is subject to wide variations in physical properties, not only from species to species, but within different portions of a single piece of wood. For this reason, piece-to-piece and within-a-piece retention of preservatives is erratic and not always satisfactory. Published information indicates that in the case of creosote and PCP, the retentions in a given pressure treating charge of wood may vary as much as from 1 to 4 and sometimes even higher. Thus, to obtain a typical average retention, it is necessary to accept the fact that many pieces of the wood will be grossly undertreated. Treating to a minimum retention specification is not economically feasible since the cost of greatly overtreating the bulk of the wood will be required. Thus, it is the industry practice to treat only to an average which undoubtedly is an important cause of pressure failures in service of, for example, utility poles, railroad ties and the like. The compositions of this invention exhibit a much narrower range of retention than creosote and chlorophenol solutions. The improvement is substantial and provides obvious performance and economic advantages. Premature failure in service from undertreatment is reduced and the improvement allows significant reduction in average retentions at a considerable cost savings.

Certain of the prior art wood preservatives, such as CCA salts, are temperature sensitive in that they will precipitate rapidly from solution when heated and in contact with wood. For this reason, it is known to the industry that CCA salts should not be used in wood preservation processes at temperatures above about 120° C. This temperature limitation carries two drawbacks: (1) higher operating temperatures which generally allow a shorter treating cycle cannot be used, and (2) since the center of a reasonable sized piece of wood is seldom penetrated by the preservatives, especially in the case of the hard woods, the upper temperature limitation imposed through the use of CCA salts does not permit good sterilization of the unpenetrated core. Should decay fungi be present in the wood prior to treatment, these can continue to grow unchecked in the untreated portion of the wood. This may be of little consequence if the untreated center is small cross section, since the major contributor to wood strength is in the outer treated portion of the cross section, but in the case of species of wood that contain comparatively large, generally impenetrable section of heart wood, the loss of the untreated center to decay can bring about rapid wood failure in service. The compositions of this invention, on the other hand, have no practical limitations as to temperatures to which they can heated in the treatment of wood, being limited only by the upper limit to which the wood itself can be heated without damage which is generally considered to be about 245° F.

As noted above, the empty-cell process has many advantages since the wood, after treament, is not left saturated with the treatment liquid. Empty-cell processes cannot economically be practiced with any degree of efficiency with water-borne preservatives as typified by the CCA salts. These salts are incompatible with the water-leachable materials in the wood and, as a result, the contamination contained in the kickback (particularly solid soluble sugars) causes precipitation within working solution of sludge-like deposits that render the working solution useless for further treatment. Not only does this represent a significant economic loss, but further, due to the toxic nature of the CCA salts, a difficult disposal problem is presented. For this reason, water-borne preservatives, such as CCA salts, are generally impregnated into the wood using full-cell processes, despite their disadvantages, rather than accept the problem of dealing with the kickback that results from empty-cell processes. However, in the method of this invention, there is no incompatibility with the compositions of this invention and the materials leached from the water so that no unmanageable precipitates are collected in the kickback. Thus, in the practice of this invention, empty-cell processes may conveniently be used, gaining the inherent advantages of an empty-cell treatment with a water-borne high-performance preservative not readily attainable in the prior art.

Certain wood preservatives, and particularly watarborne salts, tend to embrittle the wood to a degree that depends on several factors including the level of salt retention in the wood. No such embrittlement is imparted to the wood in the practice of the instant invention, and this may be of considerable significance, such as in the preservation of railroad ties, where continued impact of high-speed rolling stock may cause rail tie failure due to the brittle nature of the wood prior to the time that the ties would fail from microbial decay.

It is conventional to dry lumber prior to any pressure impregnation treatment since green wood, having its cells filled with water, is essentially saturated and cannot accept impregnating fluids. Water-soluble preservatives can enter the wood by diffusion, but this is, at best, unreliable, and at worst, of little value except at the surface of the wood. The requirements for a water-soluble preservative that retains its solubility during a lengthy diffusion process as is required with diffusion impregnation, limits the choice of preservatives to only a few permanently water-soluble toxicants such as borax and zinc chloride which really cannot be considered high performance preservatives. On the other hand, the compositions of this invention combine the water-solubility and sap compatibility prerequisites of successful diffusion preservative with high performance and resistance to leaching since, after drying, the preservative of this invention becomes water-insoluble and affixed to the wood.

There are some applications of wood preservatives in which a preservative is applied or reapplied after a structure, such as building, has been erected. Since it is physically impossible to use pressure impregnation methods in these instances, either brush or spray application must be relied upon. However, since the brush or spray application generally will penetrate only the surface regions of the wood, it is generally desired to increase the concentration of the active ingredients in these treatment solutions to as high a level as possible so that their lack of penetration will, in part, be compensated for by their strength. With present preservatives, there are severe limitations on the strength of the preservative treatment solution that can be used including, low preservative activity per unit of weight, high mammalian oral or skin toxicity, high skin and eye irritation, strong odor and color, subsequent unpaintability, flammability, and high viscosities. In contrast, in the practice of this invention, these limitations to the use of the preservative in highly concentrated solutions are generally eliminated, which allows the application of solutions with preservation efficacy or perhaps about ten times that of the present products per unit of weight. Due to the low toxicity, the use of such highly concentrated solutions does not present a danger to the health of the operator.

EXAMPLE 1

The composition below was prepared.

| Oxine | 8.2 parts by weight |
|---|---|
| Copper hydrate | 2.8 parts by weight |
| DDBSA | 59.0 parts by weight |
| Propylene glycol methyl ether | 30.0 parts by weight |

Southern pine sapwood stakes were impregnated with the composition diluted 1:49 in water to a total solution retention of 42 pcf (lbs per cubic foot of wood). After air-drying for 30 days, the treated ¾"×¾"×18" long stakes were cut into 1" lengths and boiled in water for 4 hours. In this extremely severe leaching test, loss of preservative from the wood averaged 12% of that originally in the wood as measured by retained Cu-8-Q content.

EXAMPLE 2

The composition of the preceding Example was diluted in water 1:19 (5% concetration). Smooth-surfaced southern pine stakes (¾"×¾"×18" long) were immersed in the solution for 3 minutes, as were stakes in a 5% PCP solution in mineral spirits. Cross solution retentions in the wood averaged 1.7 pcf for the Example 1 composition (1.0 specific gravity) and 1.2 pcf for the PCP solution (0.82 specific gravity). Giving effect for the difference in specific gravities of the two solutions, the weight retention of Example 1 solution was 16% higher than the PCP solution.

Under identical conditions of vacuum-pressure impregnation, a 5% solution of PCP in a petroleum solvent (specific gravity of 0.9) and a 4% solution (1.0 specific gravity) of Example 1 composition were employed to treat dry southern pine stakes (¾"×¾"×18"). The average retention of the former preservative was 31 pcf as compared to 42 pcf for the latter. Taking into account the specific gravity differences, the composition of Example 1 exhibited an average retention 22% higher than the PCP solution.

EXAMPLE 3

The following composition was prepared and water-diluted for use:

| Oxine | 4.1 parts by weight |
|---|---|
| Copper hydrate | 1.4 " |
| DDBSA | 64.0 " |
| Methanol | 30.5 " |

Also prepared were solutions of PCP in a petroleum oil. Both the foregoing composition and the PCP solution were used to pressure impregnate ¾"×¾"×18" dry, smooth-surfaced southern pine stakes to seven retentions in the case of the composition of the invention and to four retentions for the PCP ingredient concentration in solution was adjusted to yield the desired retention on the basis of an average of 42 pcf total solution pickup in the case of the above composition and 31 pcf in the case of the PCP solutions. The retentions hereafter are reported in terms of total weight of the above composition and PCP.

A full cell vacuum-pressure treatment procedure was used. The retort charge per retention was 100 stakes. Treatment operatiqng schedule was the same for both types of preservatives solutions in all retentions.

Weighing each stake before and after pressure treatment yielded these results:

|     |          | Retention Range (pcf) | Low to High Difference (%) |
|-----|----------|-----------------------|----------------------------|
| (A) | Example 3 |                      |                            |
|     | Charge #1 | 0.29 to 0.37         | 28                         |
|     | Charge #2 | 0.32 to 0.42         | 31                         |
|     | Charge #3 | 0.52 to 0.72         | 38                         |
|     | Charge #4 | 0.68 to 0.97         | 43                         |
|     | Charge #5 | 1.00 to 1.28         | 28                         |
|     | Charge #6 | 1.05 to 1.43         | 36                         |
|     | Charge #7 | 1.44 to 1.78         | 24                         |
|     |           |                      | 33 Average                 |
| (B) | PCP      |                      |                            |
|     | Charge #1 | 0.16 to 0.25         | 56                         |
|     | Charge #2 | 0.27 to 0.49         | 81                         |
|     | Charge #3 | 0.32 to 0.67         | 109                        |
|     | Charge #4 | 0.43 to 0.92         | 114                        |
|     |           |                      | 90 Average                 |

The foregoing retention ranges represent the spread from the lowest to the highest retention obtained in the treatment of each 100 stake charge.

The improvement in retention uniformity of the compositions of this Example compared to PCP is large, both as to individual charges and overall averages. Of further note to the relatively uniform spread in the high-low differences from charge-to-charge in the case of this Example whereas in the case of PCP, the retention range is progressively larger as the average retention increases. This is of significance since the composition of this Example is normally used in the 0.2 to 0.6 pcf range whereas the normal use retention of PCP is 0.4 to 0.6 pcf. The average high-low spread, therefore, in the most-used retention range is 32% versus over 100% for PCP.

EXAMPLE 4

The composition of Example 1 was diluted 1:9 and 1:99 in water and heated to 210° F. for 24 hours in a closed reflux system. No appearance difference was noted before and after the heating period, either at 210° F. and after cooling the solutions to room temperature.

Freshly prepared 1:9 and 1:99 use dilutions were then maintained at 210° F. 24-hours with the solutions separately containing green and dry southern pine wood (10 gms of wood per 100 gms of test solution). No solution appearance changes were noted.

Southern pine sap was obtained by compressing fresh-sawn green pine at 2000 psi and collecting the discharged sap. A 1:49 use dilution of Example 1 composition was prepared and admixed with pine sap in three weight ratios: 1 to 2, 1 to 1, and 2 to 1. After 4-hours heating at 210° F., no appearance charge was noted. After 3-month storage at room temperature, no appearance charge was noted.

All solutions, before and after the test procedures were transparent, true solutions. All solutions after the test procedures exhibited no significant change in active ingredient content.

EXAMPLE 5

Fresh cut green southern pine sapwood stakes (1"×1"×72" long) were dip immersed into an 8% water solution of the Composition Example 1, in a vertical position, allowing the top 24" of the stake to remain above the level of the solution. After one-week, the stakes were removed and cut into 6" lengths and the cross-section of each piece qualitatively checked for depth and uniformity of preservative penetration. All pieces originally immersed in the solution exhibited complete and essentially uniform penetration as measured by color change from natural wood to black, from the placement on the wood of a 1% dithio oxamide (a copper indicator) in isopropanol.

In addition, preservative penetration completely through the cross-section of the stakes occurred up to about 10" above the point of immersion.

SECTION 9

According to another embodiment of our invention we have discovered a method for the preservation of foodstuffs and the prevention of mammalian diseases caused by contaminated food which involves using the compositions of section 1 (hereinafter referred to as "the compositions of this invention").

More particularly, this invention relates to the preservation of foodstuffs and to methods for the treatment of raw and prepared foodstuffs as well as food handling equipment and packaging materials to prevent spoilage and mammalian diseases caused by pathogens.

DESCRIPTION OF THE PRIOR ART

For many years antimicrobial compositions have been used in the treatment of foodstuffs to prevent their deterioration and to prevent diseases in humans and animals that may be caused by food contamination. These antimicrobials have been used not only in treating raw and finished food products, but also to prevent contamination that may be occasioned by the use of unclean handling and transportation facilities and packaging materials.

The problem of the preservation of food and the danger to mammals caused by contaminated food has been an age-old problem. Some authorities have stated that more people in the Middle Ages died of ergot poisoning, a toxic fungal metabolite of rye cereal grain, than of the plague. Even today it has been suggested by some authorities that food poisoning may cause some 90% of all human illness.

Since foodstuffs are intended to be ingested by humans and animals, it goes without saying that the safety of their use and low toxicity are essential considerations. This fact has severely limited the availability of known antimicrobials for food use. The antimicrobials that currently find favor and are sanctioned for use generally are of a low order of efficacy which frequently results in a high cost-to-performance ratio, particularly when used on raw foodstuffs for preservation.

Mycotoxin formation in raw plant foods is a cause of growing concern. Those produced by certain Aspergillis, Penicillium, Alternaria, Trichoderma, Helminthosporium and other fungi are among the most toxic substances known to man and are potent carcinogens, teratogens and tremorgens. Proper handling and storage conditions drastically reduce, if not eliminate, these fungi, and hence the production of dangerous toxins. But even in the industrial nations, it is virtually impossible to effect adequate control over hundreds of millions of tons of agricultural products which are grown, handled and stored by millions of persons. The result is varying degrees of fungal growth on a significant portion of the total. Subsequent processing generally destroys the fungi but not the mycotoxins.

Incidence of adverse effects on humans of mycotoxins in food is difficult to assess in the high technology nations, but is readily apparent in a number of the undeveloped tropical areas where very favorable mold growth conditions are coupled with few safeguards.

Incidence of animal, particularly livestock, disease from both fungi and mycotoxins usually is higher than for humans. Some livestock and poultry diseases, caused by consumption of moldy feed, cause serious economic losses. Aflatoxin M, an extremely toxic mycotoxin, has been found in the milk of cows that have eaten moldy grain.

OBJECTS OF THE INVENTION

Accordingly, it is an object of this invention to provide methods for the treatment of raw and prepared foodstuffs that are effective to prevent food deterioration and diseases in mammals through the use of antimicrobial compositions that are generally nontoxic to animal and plant life.

Another object of this invention is to provide for the use of antimicrobial compositions that are comparatively nontoxic to animal and plant life, but which are highly efficacious in destroying microorganisms that cause food spoilage and disease-causing organisms.

Briefly, these and other objects of this invention are achieved by treating foodstuffs and handling equipment and packaging materials that come in contact with foodstuffs with a composition according to section 1.

DESCRIPTION OF THE INVENTION

The compositions of this invention have unique utility for foodstuff preservation by reason of safety, antifungal and antibacterial efficacy that may be orders of magnitude superior to current materials, and has virtually no color, odor or taste in use concentrations. Additional features include residual persistence, low volatility, high heat and sunlight stability and water insolubility after application, and excellent economy of use.

Among the suitable preservative applications for compositions of the invention, the following may be mentioned:
(1) Fresh fruit, vegetables and nuts;
(2) Dried fruits and vegetables during the dehydration process;
(3) Cereal grains for human, animal and poultry consumption;
(4) Animal silage;
(5) Prepared foodstuffs;
(6) Meat, fish and dairy products;
(7) Fruit and vegetable juices and fruit condiments; and
(8) Handling and processing equipment, storage and transportation facilities, and packaging materials for foodstuffs.

The most used preservatives typically are sanctioned in the 100 to 1,000 ppm concentration range in foodstuffs. These preservatives have acute oral $LD_{50}$ toxicities in the 100 to 5,000 mg/kg range. By contrast, the concentrates of this invention, exhibiting an $LD_{50}$ of 1,500, are effective generally for preservation in the range of 1 to 25 ppm against both fungal and bacterial attack. When the concentrates are diluted for efficacious use, they may display $LD_{50}$ toxicities above about 20,000 mg/kg. Therefore, the compositions of the invention have considerably lower toxicity in adequate use concentrations than present food preservatives.

The following examples demonstrate the utility of this invention for a variety of food preservation applications:

EXAMPLES

Example 1

The following composition was prepared and tested for control of fungal growth on an outside, exposed-to-the-weather concrete slab which was covered completely at the start of the test with black fungal growth of unknown species (amounts are parts by weight):

| | |
|---|---|
| Oxine | 4.4 |
| Copper hydrate | 1.5 |
| DDBSA | 64.0 |
| Methanol | 30.1 |

After 1:150 use dilution in water, the composition was applied to the concrete slab by spraying to run-off. Within six months the black fungal growth had completely disappeared and no regrowth was noted during a two-year observation period thereafter. The six-month period to initially remove the fungi is believed to be that required for the dead organisms to dry, break up and become unadhered to the concrete, and finally, to be washed away by rain.

In summary, the compositions of this invention provide both a spectrum and a magnitude of performance against plant and mammalian pathogens seldom seen in any antimicrobial and heretofore unknown in one safe enough for foodstuff use.

EXAMPLES 2-9

Examples 2 through 9 that follow illustrate the broad spectrum of the compositions of this invention for controlling fungi that cause foodstuff spoilage, that are pathogenic to mammals, and that produce dangerous mycotoxins.

Example 2

The following composition was tested for minimum fungicidal concentration and compared to two well known anti fungal chemicals—pentachlorophenol and 2,3,5 trichloro-4-propyl-sulfonyl pyridine—and DDBSA.

| | |
|---|---|
| Oxine | 8.2 parts by weight |
| Copper hydrate | 2.8 parts by weight |
| DDBSA | 59.0 parts by weight |
| Propylene glycol methyl ether | 30.0 parts by weight |

All of the test composition concentrations to be tested were incorporated in the fungal growth media (agar) in accordance with standard microbiological practices. Agar plugs containing the test fungicides then were inoculated with a sporulating culture and inoculated at the temperatures and times specified by The American Type Culture Collection (ATCC) recommendations. The plugs were then scored for absence or presence of organism growth. The results are shown in the following table. Minimum fungicidal concentrations were determined against a broad spectrum of fungi that are detrimental to man, foodstuffs and materials and which can result in metabolite formations (mycotoxins) of extreme toxicity to man and animals.

In the table below, Composition A is that of this Example 2 and the active ingredient is Cu-8-Q; Composition B is DDBSA; Composition C is pentachlorophenol; and Composition D is 2,3,5-trichloro-4-propylsulfonyl pyridine. Where no concentration is listed, no data is available. The stated value of "1" means 1 or fewer ppm.

|  | Minimum Fungicidal Concentration (ppm of active ingredient) | | | |
|---|---|---|---|---|
|  | A | B | C | D |
| Aspergillis niger (ATCC 9642) | 1 | 10,000 | 1–3 | — |
| Aspergillis terreus (ATCC 10609) | 1 | 100 | — | 36 |
| Aspergillis flavus (ATCC 11655) | 1 | 1,000 | 22–54 | — |
| Alternaria alternata (ATCC 13963) | 1 | — | — | — |
| Aureobasidium pullulans (ATCC 16624) | 1 | 100 | — | — |
| Lenzites trabea (ATCC 11539) | 1 | 100 | 1–3 | — |
| Polyporus tulipiferae (ATCC 11245) | 1 | 100 | 1–3 | — |
| Penicillium brevi compactum (ATCC 16024) | 1 | 100 | — | — |
| Rhizopus stolonifer (ATCC 24794) | 1 | 100 | 1–3 | — |
| Trichoderma viride (ATCC 8678) | 10 | 100 | — | — |
| Trichoderma sp. (ATCC 12668) | 1 | 100 | — | — |
| Candida albicans (ATCC 10259) | 1 | 1,000 | — | 3 |

These results illustrate the high efficacy of the composition of this invention and confirm the fact that an antifungal composition prepared from a Cu-8-Q/DDBSA solution is much superior to DDBSA alone. The results also indicate the favorable relative efficacy of the test composition compared to the two commercially available fungicides of recognized high performance.

Example 3

The purpose of this test was to determine antifungal efficacy of DDBSA/Cu-8-Q solutions and to compare their efficacy to that of a world standard, sodium pentachlorophenate, and a mixture of two well-known agricultural fungicides, Topsin M (a thiophenate) and Nabam (a thiocarbomate). The test method is designated as a proposal for the Finnish NWPC Standard No. 1.4.1.3/1974. The test substrate was fresh cut, green pine wood. The test fungi were:

Blue stain fungi—mixture of
  Ceratocystis pilifera Z11
  Sclerophoma entoxylina Z17
  Puliularia pullulans U2
Mold fungi—mixture of
  Paecilomyces varioti X15
  Cladosporium sphaerospermum R7
  Aspergillis amstelodami X19

In the table below, Composition A is formuation comprised of 64 wt. % DDBSA, 5 wt. % Cu-8-Q and 31 wt. % methanol diluted 1:200 with a water carrier.

Composition B is the same formulation diluted 1:100 with a water carrier.

Composition C is a 1.5% concentration of sodium pentachlorophenate in water.

Composition D is a 0.4% concentration in water of a 47:53 weight ratio of Topsin M:Nabam.

E refers to untreated control pine boards.

The rating index is:

|  | Test Composition | | | | |
|---|---|---|---|---|---|
|  | A | B | C | D | E |
| Blue stain fungi growth | 0.8 | 0.3 | 0.5 | 2.5 | 3.9 |
| Mold fungi growth | 0.5 | 0 | 0.3 | 1.3 | 3.6 |

0 = no visible growth
1 = traces of growth
2 = slight growth
3 = moderate growth
4 = covered with fungi The demonstrated efficacy of Compositions A and B against the six listed fungal organisms has utility not only on the tested substrate—wood—but also for protection of a variety of other materials that are attacked by one or more of the fungi, including paint, concrete, brick, textiles and leather.

Example 4

Using the standard AOAC fungicidal test method (12th Edition, 1975), the composition below was evaluated against two widespread fungi.

| Oxine | 2.08 parts by weight |
|---|---|
| Copper hydrate | 0.70 parts by weight |
| DDBSA | 40.00 parts by weight |
| Isopropanol | 32.00 parts by weight |
| Demineralized water | 25.22 parts by weight |

The two fungi were Aspergillis niger, a ubiquitous black fungus which flourishes on a broad range of substrates, and Trichophyton mentagrophytes, a cause of "athlete's foot."

A. niger—at 1:200 use dilution in a water carrier, no growth after 10 minutes' exposure.

T. mentagrophytes—at 1:750 use dilution in a water carrier, no growth after 10 minutes' exposure.

Similar but somewhat lower efficacy results were obtained by substituting zinc-8-Q or aluminum-8-Q in the composition of this example, produced by reacting zinc oxide and aluminum hydroxide respectively with oxine.

Example 5

The compositions of this invention exhibit efficacy against a broad spectrum fungal plant pathogens, as illustrated by various use dilutions in a water carrier of the following composition:

| Copper hydrate | 1.70 parts by weight |
|---|---|
| 8-hydroxy quinoline | 4.44 parts by weight |
| Isopropanol | 35.00 parts by weight |
| DDBSA | 58.86 parts by weight |

A. Valencia Oranges

Tested on harvested fruit against Phomopsis stemend rot and Diplodis rot, at a 1:100 use dilution, 2-minute dip application. After 3 weeks at 70° F., the following percentages of decay were noted:
Control (untreated)oranges—9.5% decay
Treated oranges—5.3% decay B. Sugar Cane An agar seeding test against Ceratocystis paradoxa (pineapple disease) at a 1:10,000 (100 ppm) use dilution yielded a 3.0 mm. inhibition zone.

C. Peach Trees

Tested against *Taphrina deformans* (causes leaf curl disease). Four test trees were sprayed twice, two weeks apart, with a 1:400 use dilution. Three months later, 100 leaves on each test tree were rated for leaf curl:
Control (untreated) leaves—100% leaf curl
Treated leaves—13.5% leaf curl D. Cotton Effectiveness against 11 fungi and 1 bacterium (*Xanthomonas malvacearum*) that are associated with disease of cottonseed, seedlings and other plants was evaluated in vitro, usng the following compositions:

| Composition #1 | Copper hydrate | 1.70 parts by weight |
| | 8-hydroxy quinoline | 4.44 parts by weight |
| | Methanol | 4.00 parts by weight |
| | Isopropanol | 30.86 parts by weight |
| | DDBSA | 59.00 parts by weight |
| Composition #2 | Copper hydrate | 2.80 parts by weight |
| | 8-hydroxy quinoline | 8.20 parts by weight |
| | Methanol | 4.00 parts by weight |
| | Isopropanol | 26.00 parts by weight |
| | DDBSA | 59.00 parts by weight |

Both compositions were prepared in accordance with procedures stated in previous examples.

The following results were obtained, expressed in parts per million (ppm) of total test composition in water carrier and the relative growth inhibition provided at each test strength on each tested organism. In the tables below:

| Test Organisms | contractions (ppm) | | | | | | |
|---|---|---|---|---|---|---|---|
| | 0 | 1 | 5 | 25 | 100 | 500 | 1000 |
| Composition #1 | | | | | | | |
| *Pythium ultimum* (41B) | 0 | 0 | 0 | 1 | 2 | 3 | 3 |
| *Rizoctonia solani* (1D) | 0 | 0 | 0 | 1 | 2 | 3 | 3 |
| *Fusarium* (4A) | 0 | 0 | 0 | 3 | 3 | 3 | 3 |
| *Fusarium* (4D) | 0 | 1 | 1 | 2 | 2 | 2 | 3 |
| *Fusarium roseum* (4C) | 0 | 0 | 0 | 1 | 2 | 2 | 3 |
| *Colletotrichum gossypii* (35A) | 0 | 0 | 0 | 1 | 2 | 2 | 2 |
| *Xanthomonas malvecearum* (2A) | 0 | 0 | 0 | 0 | 2 | 2 | 3 |
| Composition #2 | | | | | | | |
| *Pythium ultimum* (41B) | 0 | 0 | 1 | 2 | 2 | 2 | 2 |
| *Rhizoctonia solani* (1D) | 0 | 0 | 1 | 2 | 2 | 2 | 2 |
| *Fusarium* (4A) | 0 | 0 | 1 | 1 | 1 | 2 | 2 |
| *Fusarium* (4D) | 0 | 0 | 1 | 1 | 2 | 2 | 2 |
| *Fusarium roseum* (4C) | 0 | 0 | 0 | 2 | 2 | 2 | 2 |
| *Colletotrichum gossypii* (35A) | 0 | 0 | 0 | 2 | 2 | 2 | 2 |
| *Xanthomonas malvecearum* (2A) | 0 | 0 | 0 | 1 | 1 | 2 | 2 |
| Composition #1 | | | | | | | |
| Aspergillis sp. | | | | | | 1 | 1 |
| *Helminthosporium oryzae* | | | | | | 2 | 2 |
| Mucor mucedo | | | | | | 1 | 1 |
| Penicillium sp. | | | | | | 1 | 1 |
| Rhizopus sp. | | | | | | 1 | 1 |

0 = no apparent inhibition
1 = some inhibition
2 = considerable inhibition (little growth
3 = total inhibition (no growth)

Example 6

The composition of Example 4 was screened for fungal pathogen response as a foliar spray on beans and rice. The rating scale is from 0 (no pathogen control) to 10 (complete pathogen control). The concentration of active ingredient (in a water carrier) of all compositions tested is 33 parts per million (ppm). The active ingredient in the composition of Example 4 is expressed in terms of Cu-8-Q and the chemical as listed below for four comparative products. The comparative products tested were Karathane (2,4-dinitro-6-(2-octyl phenyl crotonate), Vitavax (5,6-dihydro-2-methyl-1,4-oxathiin-3-carboxanilide), Daconil (tetrachloroisophthalonitrile) and Maneb (manganese ethylenebisdithiocarbamate). The plants and diseases tested were bean mildew (*Erysiphe polygoni*), bean rust (*Uromyces phaseoli typica*) and rice spot (*Helminthosporium orazae* and *Cerocospora orazae*).

| | Bean Mildew | Bean Rust | Rice Spot |
|---|---|---|---|
| Example 28 composition | 8 | 10 | 10 |
| Karathane | 10 | — | — |
| Vitavax | — | 9 | — |
| Daconil | — | — | 10 |
| Maneb | — | — | 8 |

Example 7

The following composition was evaluated (diluted with water for use) in vitro for inhibition against two fungal pathogens, Botrytis sp. and Alternaria sp., causal agents of a variety of plant diseases.

| Oxine | 2.08 parts by weight |
| Copper hydrate | 0.70 parts by weight |
| DDBSA | 40.00 parts by weight |
| Triton X-100 | 20.00 parts by weight |
| Isopropanol | 22.00 parts by weight |
| Water (demineralized) | 15.22 parts by weight |

The zone of inhibition agar plate test also was used to test Cunilate 2174 (diluted in mineral spirits for use) for comparison. The composition concentrations in the table of results below are expressed in parts per million (ppm) of Cu-8-Q. The larger the inhibition zone, the greater is the efficacy of the composition.

| | Botrytis | | | Alternaria | | |
|---|---|---|---|---|---|---|
| DDBSA/Cu—8-Q | | | | | | |
| Concentration (ppm) | 21 | 50 | 125 | 21 | 50 | 125 |
| Inhibition zone (mm) | 13 | 15 | 22 | 0 | 16 | 21 |
| Cunilate 2174 | | | | | | |
| Concentration (ppm) | 83 | 200 | 500 | 83 | 200 | 500 |
| Inhibition zone (mm) | 13 | 14 | 16 | 0 | 0 | 14 |

The DDBSA/Cu-8-Q solution of this invention exhibits an improvement in efficacy against the tested organisms by a factor of 4× in the case of Botrytis to 10× in the case of Alternaria.

Example 8

The DDBSA/Cu-8-Q solution of the preceding example (31), diluted 1:400 in a water carrier, was applied by spray nine times, at two-week intervals, to peach and nectarine cultivars during the growing season. The results against brown rot (*Monolinia fructocola*), compared to nontreated trees, is presented below.

| | % Fruit Affected | |
|---|---|---|
| | Peach | Nectarine |
| At harvest (treated) | 1 | 3 |
| At harvest (untreated) | 15 | 43 |
| Five days later (treated) | 3 | 6 |

-continued

|  | % Fruit Affected | |
|---|---|---|
|  | Peach | Nectarine |
| Five days later (untreated) | 60 | 67 |

Example 9

The DDBSA/Cu-8-Q soution of Example 8 was tested in vitro against a major turf pathogen, *Helminthosporium vagans*, via a standard agar plate culture technique, with these results:

|  | Fungus Colony Diameter |
|---|---|
| 1:6700 use dilution in water carrier | 1 mm |
| 1:3350 use dilution in water carrier | 0 |
| Control | 21 mm |

The results demonstrate very high efficacy in controlling this important pathogen. Complete control of *H. vagans* was achieved in this assay between 3.7 and 7.6 ppm of Cu-8-Q.

As illustrated in the examples to follow, the compositions of this invention have high efficacy against a broad spectrum of bacteria that are pathogenic to mammals and plant life, that contribute to reduced water quality, that cause deterioration of foodstuffs, that degrade a broad range of manufactured and natural materials and products, and which generate toxic metabolites (bacteria-toxins) that are among the most poisonous substances known to man.

Of particular interest is high efficacy against Gram-negative as well as Gram-positive microorganisms. Few antibacterial materials now available are effective against the Gram-negatives and still fewer provide economical control of them. A number of available antibacterials toxic to Gram-negative organisms have practical limitations which severely restrict use, including high mammalian toxicity, phytotoxicity, corrosiveness to skin and a variety of materials, strong odor, strong color, high volatility, low or erratic shelf stability, low or nonexistent residual activity, and prohibition of use at elevated temperatures.

The basic significance in the need for Gram-negative control lies in the fact that this bacterial category includes a number of widespread, virulent pathogens which are difficult to impossible to control with presently available antibiotics, notably Pseudomonas sp. typified by *Pseudomonas aeruginosa* PRD-10, the standard strain in the United States for evaluation of antibacterials for mandatory Gram-negative control applications.

The compositions herein disclosed eliminate or substantially reduce these use limitations inherent in many other germicides. The compositions are quite unique in having strong Gram-positive and Gram-negative activity combined with broad versatility of formulation and use plus a high degree of safety (low toxicity and zero to low skin and eye irritation). Add to this the high efficacy, broad spectrum antifungal activity of the compositions of this invention and the resulting range of toxicity to target organisms and safety to man, the most sensitive of hosts, is unique indeed.

The balance of toxicity provided by this invention to Gram-positive, Gram-negative and fungal microorganisms has special value in the broad consumer field of skin deodorancy. Present antibacterials suffer from the fact that they are effective primarily against Gram-positives, allowing Gram-negative and fungi overgrowth, a condition considered dangerous by many authorities.

Example 10

The DDBSA/Cu-8-Q solution of Example 2 was tested, along with a number of well known antimicrobial agents, against a broad spectrum screen of economically important Gram-positive and Gram-negative bacteria. All antimicrobial agents were incorporated in the agar bacterial growth media according to standard microbiological practices. The bacterial species were grown in nutrient broth; 24-hour cultures, the inoculum, then were streaked onto the nutrient agar plates containing the test antimicrobials. After a 24-hour incubation at the appropriate temperature, the plants were rated for presence or absence of bacterial growth.

Minimum bactericidal concentrations for each of the tested agents are stated in the following tabulation of results in parts per million (ppm) of active ingredient as defined in the description of each agent.

|  | Antimicrobial Agent (ppm* of active ingredient) | | | | | | |
|---|---|---|---|---|---|---|---|
| Bacteria (ATCC No.) | A | B | C | D | E | F | G |
| Gram-positive: | | | | | | | |
| *Bacillus cereus* | 1 | 100 | — | 7 | 8 | 5–10 | — |
| *Bacillus lichenforms* (27326) | 1 | 100 | — | 7 | 8 | 2–5 | — |
| *Bacillus megaterium* (27327) | 1 | 100 | — | 7 | 8 | — | — |
| *Bacillus subtillis* (37328) | 1 | 100 | — | 750 | 8 | — | 3 |
| *Micrococcus flavus* (10240) | 1 | 100 | — | 7 | 8 | — | — |
| *Mycobacterium phlei* (15610) | 1 | 10 | — | 7 | 8 | — | 3 |
| *Staphylococcus aureus* (6538) | 1 | 100 | 2083 | 7 | 8 | 1–3 | 3 |
| Gram-negative: | | | | | | | |
| *Alcaligenes faecalis* (337) | 10 | 1000 | — | 750 | 80 | — | — |
| *Alcaligenes marshalii* (21030) | 104 | 100 | — | 7 | 8 | — | — |
| *Esherichia coli* (11229) | 104 | 10,000 | — | 750 | 80 | 250–500 | 165 |
| *Flavobacterium arboresceus* (4358) | 10 | 10 | 4166 | 7 | 8 | — | — |
| *Klebsiella pneumoniae* (4356) | 10 | 10,000 | — | 750 | 8 | — | — |

-continued

| Bacteria (ATCC No.) | Antimicrobial Agent (ppm* of active ingredient) | | | | | | |
|---|---|---|---|---|---|---|---|
| | A | B | C | D | E | F | G |
| *Proteus vulgaris* | 10 | 1000 | — | 750 | 800 | — | — |
| *Pseudomonas aeruginosa* (15442) | 104 | 1000 | 4166 | 750 | 800 | 1000–2500 | 165 |
| *Salmonella cholerasuis* (10708) | 104 | 1000 | — | 750 | 80 | 250–500 | 165 |
| *Salmonella typhi* (6539) | 104 | 1000 | 2083 | 750 | 80 | — | 165 |

*stated value of "1" means 1 or less
A = the DDBSA/Cu—8-Q solution of Example 2 with the active ingredient expressed in terms of Cu—8-Q.
B = DDBSA.
C = phenol
D = Betadine, an iodine/polyvinylpyrrolidone complex containing 0.75% iodine. The active ingredient is iodine.
E = Alkyl dimethyl ammonium chlorides (61% $C_{12}$, 23% $C_{14}$, 11% $C_{16}$ and 3% $C_{10}$).
F = sodium pentachlorophenate
G = 2,3,5-trichloro-4-propylsulfonyl pyridine.
See previous list of antimicrobial agents These data demonstrate the high efficacy of the composition of Example 2. On the basis of the average of the efficacies against all the test organisms, Composition A is 45 times superior to Composition B; 88 times better than Composition C; 10.7 times better than Composition D; and 3.5 times superior to Composition E.

On the basis of the average of the efficacies against the three test bacteria (*Staphylococcus aureus, Salmonella cholerasuis* and *Pseudomonas aeruginosa* PRD-10) required by the Environmental Protection Agency of a "hospital grade" disinfectant, Composition A is 10 times better than Composition B; 7.2 times better than Composition B; and 1.6 times better than Composition E.

Example 11

The composition set forth below was prepared by previously described procedures:

| | |
|---|---|
| Oxine | 2.08 parts by weight |
| Copper hydrate | 0.70 parts by weight |
| Isopropanol | 32.00 parts by weight |
| DDBSA | 40.00 parts by weight |
| Water (demineralized) | 25.22 parts by weight |

When evaluated as a bactericide by the AOAC Use Dilution Method (12th Edition, 1975), 10 ring carriers per organism, the following results were obtained (A=-subculture and B=resubculture):

| | Use Dilution in Water Carrier | Negative | | Positive | |
|---|---|---|---|---|---|
| | | A | B | A | B |
| *Staphylococcus aureus* | 1:1000 | 10 | 10 | 0 | 0 |
| *Salmonella cholerasuis* (PRD-10) | 1:1000 | 10 | 10 | 0 | 0 |
| *Pseudomonas aeruginosa* | 1:400 | 10 | 10 | 0 | 0 |
| *Aerobacter aerogenes* | 1:400 | 10 | 10 | 0 | 0 |

A ten-minute kill is required against the first three pathogens for sale as a hospital grade disinfectant. Efficacy against the fourth organism, a major cause of slime in recirculated cooling water systems and pulp and paper mills, demonstrates utility of the composition as a slimicide.

Example 12

This composition was prepared and tested at one use dilution, 1:50 in water carrier, against the causal agent of potato ring rot bacteria (*Corynebacterium sepedonicm*):

| | |
|---|---|
| Oxine | 2.08 parts by weight |
| Copper hydrate | 0.70 parts by weight |
| DDBSA | 40.00 parts by weight |
| Triton X-100 | 20.00 parts by weight |
| Isopropanol | 22.00 parts by weight |
| Water (demineralized) | 15.22 parts by weight |

Infected potato seed readily contaminate potato seed cutters, sacks, bins cellars, trucks and planting equipment with the highly infectious ring rot bacteria. The result may be infected potato plants, tubers and reduced yields.

The test procedure consisted of dipping unpainted, planed wood laths (6") into a slurry of infected ring rot tuber tissue, allowing excess slurry to drain off (3–5 minutes) and then spraying the contaminated lath with the test antibacterials. Three to five minutes later, healthy Norgold Russet potato seed pieces were rubbed vigorously against both sides of the contaminated and antibacterial-treated laths. The process was repeated using laths not contaminated with *C. sepedonicum* but treated with the test antibacterial agent. The rubbed seed pieces were stored in bags and later planted at the appropriate time.

In addition to the composition of the invention, untreated controls, 20% Clorox (1.05% sodium hypochlorite in water), formaldehyde (37% formalin diluted 1:120 in water) and Roccal (benzalkonium chloride or zephiran chloride) diluted with water to 800 ppm concentration were tested. The results of the test are tabulated below and refer to plants and tubers produced from the tubbed test seed pieces.

| Antimicrobial | Ring Rot Contaminated | % Plant Stored | % Ring Rot Plants | % Ring Rot Tubers | Yield cwt/acre |
|---|---|---|---|---|---|
| None (control) | Yes | 98 | 23 | 8 | 493 |
| None (control) | No | 95 | 0 | 0 | 609 |
| DDBSA/Cu—8-Q | Yes | 98 | 0 | 2 | 631 |
| DDBSA/Cu—8-Q | No | 100 | 0 | 0 | 602 |
| 20% Clorox | Yes | 98 | 20 | 9 | 500 |
| 20% Clorox | No | 98 | 0 | 0 | 602 |

| Antimicrobial | Ring Rot Contaminated | % Plant Stored | % Ring Rot Plants | % Ring Rot Tubers | Yield cwt/acre |
|---|---|---|---|---|---|
| Roccal | Yes | 98 | 20 | 9 | 515 |
| Roccal | No | 98 | 0 | 0 | 638 |

The composition of this example demonstrates superior control of the ring rot bacterium. Other species of the genus Corynebacterium are causal agents of disease in man and a variety of plant life.

Example 13

The composition below was prepared and tested for speed and range of antibacterial activity, in the absence and presence of organic matter (blood) for use in hospital disinfection, cold sterilization and antisepsis.

| | |
|---|---|
| Oxine | 4.1 parts by weight |
| Copper hydrate | 1.4 parts by weight |
| DDBSA | 65.0 parts by weight |
| Propylene glycol methyl ether | 29.5 parts by weight |

Many antimicrobial agents are partially or totally deactivated in the presence of organic matter, constituting a severe limitation to effectiveness of such agents for a number of uses such as wound antisepsis and medical instrumentation and surface disinfection where large amounts of organic matter often are encountered and sometimes are unavoidable.

The AOAC Use Dilution Confirmation Test (12th Edition, 1970) was modified as follows:
(a) The test temperature was 37° C.
(b) The ring carriers were soaked in sheep blood for two hours, air-dried for one hour, then contaminated with the test pathogen.
(c) The contaminated rings were contacted with the test antibacterial agent for 30-second, one-minute and three-minutes periods.

The results are set forth in the following table, in which:

| Test Pathogen | Use Dilution in Water Carrier | In Absence of Blood | | | In Presence of Blood | | |
|---|---|---|---|---|---|---|---|
| | | 30 sec. | 1 min. | 3 min. | 30 sec. | 1 min. | 3 min. |
| Staphylococcus aureus | Undiluted | 0 | 0 | 0 | 0 | 0 | 0 |
| (ATCC 6538) | 1:10 | 0 | 0. | 0 | 0 | 0 | 0 |
| | 1:100 | 0 | 0 | 0 | 3 | 6 | 3 |
| Salmonella typhi | Undiluted | 0 | 0 | 0 | 0 | 0 | 0 |
| (ATCC 6539) | 1:10 | 0 | 0 | 0 | 0 | 0 | 0 |
| | 1:00 | 0 | 0 | 0 | 0 | 0 | 0 |
| Pseudomonas aeruginosa | Undiluted | 0 | 0 | 0 | 0 | 0 | 0 |
| (ATCC 15442) | 1:10 | 0 | 0 | 0 | 10 | 10 | 0 |
| | 1:100 | 0 | 0 | 0 | 10 | 3 | 3 |

0 = no growth in 10 of 10 tubes tested
1 = growth in 1 of 10 tubes tested
2 = growth in 2 of 10 tubes tested
3 = growth in 3 of 10 tubes tested
etc.

These results indicate that the test composition is capable of rapid antibacterial action in the presence of substantial amounts of organic matter against the three human pathogens generally considered as definitive for antibacterial efficacy evaluation.

Example 14

The following DDBSA/Cu-8-Q solution was prepared in accordance with previously stated techniques. (In this instance, Cu-8-Q was formed in situ from copper hydrate and oxine, also known as 8-hydroxy quinoline.)

| | |
|---|---|
| Copper hydrate | 1.70 |
| Oxine | 4.44 |
| DDBSA | 64.81 |
| Methanol | 15.05 |
| Isopropanol | 14.00 |

This composition was diluted with a water carrier, as tabularized below, and tested in comparison with a sodium tetrachlorophenate (23%) liquid concentrate, also diluted in a water carrier, against organisms on three species of green lumber—Douglas fir, Amabilis fir and Ponderosa pine. The organisms were:

| | |
|---|---|
| Cephaloascus fragans | a brown mold that infects certain wood species |
| Trichoderma virgatum | a common cold |
| Mixed spores | a combination of two molds (Penicillium sp. and Aspergillis niger) and a fungus (Ceratocystis pilifera) that causes blue stain in wood. |

The freshly cut wood samples were dip treated (15-second immersion) with the test fungicides and then inoculated with spore suspensions of the above-described fungi. The test boards plus untreated control boards were then placed in a warm, humid chamber for four weeks. The results are set forth in the table below in which:

| | Use Dilu-tion | C. fragans | | | T. virgatum | | | Mixed spores | | |
|---|---|---|---|---|---|---|---|---|---|---|
| | | A | B | C | A | B | C | A | B | C |
| Tetrachlorophenol composition | 1:100 | 4 | 4 | 4 | 0 | 0 | 3 | 3 | 4 | 4 |
| DDBSA/Cu—8-Q solution | 1:240 | 2 | 0 | 1 | 3 | 0 | 4 | 4 | 3 | 4 |
| Tetrachlorophenol composition | 1:50 | 2 | 0 | 4 | 0 | 0 | 1 | 3 | 2 | 4 |
| DDBSA/Cu—8-Q solution | 1:120 | 0 | 0 | 1 | 3 | 0 | 1 | 2 | 2 | 2 |
| Tetrachlorophenol composition | 1:25 | 2 | 2 | 3 | 0 | 0 | 1 | 0 | 0 | 3 |

-continued

| | Use Dilution | C. fragans | | | T. virgatum | | | Mixed spores | | |
|---|---|---|---|---|---|---|---|---|---|---|
| | | A | B | C | A | B | C | A | B | C |
| DDBSA/Cu—8-Q solution | 1:60 | 0 | 0 | 0 | 1 | 0 | 0 | 0 | 0 | 0 |
| Tetrachlorophenol composition | 1:12.5 | 0 | 1 | 0 | 0 | 0 | 0 | 0 | 0 | 2 |
| DDBSA/Cu—8-Q solution | 1:30 | 0 | 0 | 0 | 0 | 0 | 0 | 0 | 0 | 0 |
| Control (no treatment) | | 4 | 4 | 4 | 3 | 4 | 4 | 4 | 4 | 4 |

A = Douglas fir
B = Amabilis fir
C = Ponderosa pine
0 = no growth
1 = no growth for 2 weeks
2 = medium growth
3 = heavy growth in 4 weeks
4 = heavy growth in 2 weeks Example 15

To further illustrate the antifungal properties of compositions of the invention, the formulation below was prepared and tested as a preservative against microbiological deterioration of 10 oz. cotton duck cloth and compared with untreated cotton duck as a control and with Cunilate 2174, a commercially available concentrate containing 10% Cu-8-Q which is made soluble in petroleum hydrocarbon solvents via use of nickel acetate and 2-ethyl hexoic acid. The previously described Nylate 10 also was tested.

| | |
|---|---|
| Oxine | 4.1 parts by weight |
| Copper hydrate | 1.4 parts by weight |
| DDBSA | 64.0 parts by weight |
| Propylene glycol methyl ether | 30.5 parts by weight |

This composition was use-diluted 1:24 with a water carrier; the Cunilate 2174 was diluted 1:19 and 1:9 with mineral spirits for use; the Nylate 10 was diluted 1:19 and 1:9 with water. The cotton samples were dipped to refusal in the test compositions, air-dried and buried at 75° F. for 29 days in sheep manure moistened with water. Microorganism attack on the cottom cloth in this test medium is both rapid and severe as can be noted from the essentially total destruction of the untreated control cloth sample. The results of this test are tabulated as follows:

| Composition (dilution) | Weight of Cu—8-Q in Cloth | Estimated Strength Loss* |
|---|---|---|
| Untreated control | 0 | 100% |
| Cunilate 2174 (1:19) | 0.41 gram | 50% |
| Cunilate 2174 (1:9) | 0.84 gram | 25% |
| Nylate 10 (1:19) | 0.61 gram | 50% |
| Nylate 10 (1:9) | 1.21 gram | 0% |
| DDBSA/Cu—8-Q (1:24) | 0.18 gram | 0% |

*As measured by tear strength reduction:
100% = total loss of strength
50% = moderately difficult to tear by hand
25% = difficult to tear by hand
0% = impossible to tear by hand The superiority of the formulation of the invention over other Cu-8-Q compositions is clearly evident.

SECTION 10

According to another embodiment of our invention we have discovered that the compositions of section 1 (hereinafter referred to as "the compositions of this invention") can be used to reduce the population growth of microorganisms.

DESCRIPTION OF THE PRIOR ART

Numerous antimicrobial agents are known to the prior art for use in treating water for sanitizing, sterilizing or reducing the growth of microorganisms. These treatments find utility for such purposes in conditioning circulation cooling water, waste water from pulp and paper processing, effluence from sewage treatment plants, water in swimming pools, drinking water, and many various discharges and wastes. One of the primary difficulties encountered in utilizing the prior art antimicrobial agents lies in the fact that many of them are quite toxic to animals and plants, and even the less toxic ones, when mixed in water in amounts necessary to obtain suitable performance, may irritate tissues such as the skin and eyes, and they may impart odors or tastes to the treated water. Further, many of the prior art antimicrobial activity which frequently results in controlling certain specific organisms at the expense of permitting overgrowth of other organisms by the removal of checks and balances. They also suffer in that they are often readily washed away and do not have high substantivity to provide ongoing antimicrobial protection for water-treating equipment such as cooling towers, conduits, vessels, basins and the like.

OBJECTS OF THE INVENTION

Accordingly, it is an object of this invention to provide a method for treating water to eliminate, reduce or otherwise control the microbe population in the water through the use of compositions that have low toxicity to animals and plants and low irritability to the skin and eyes.

Another object of this invention is to provide a method for the treatment of water and other substrates for purposes of sanitization and sterilization through the use of comparatively nontoxic, odor-free, nonirritating compositions.

Another object of this invention is to provide a method for inhibiting the growth of microorganisms in water by treating the water with compositions that are comparatively nontoxic, odor-free and nonirritating.

Another object of this invention is to provide a method for the sterilization of water and the inhibition of microorganisms that, through biological action, produce unwanted odors.

These and other objects of this invention are achieved by treating water, such as waste water, recirculating water, process water, swimming pool water, and drinking water, with antimicrobial agents solubilized with a disubstituted aryl compound having hydrophilic and oleophilic substituents. In one preferred embodiment, the antimicrobial agent is an organometallic compound, such as a metal chelate of 8-hydroxyquinoline (oxine), and the disubstituted aryl compound is an alkyl benzene sulfonic acid such as, for example, a commercial grade of dodecyl benzene sulfonic acid (DDBSA).

DESCRIPTION OF THE INVENTION

The utilization of the antimicrobial compositions of this invention are especially distinguished from prior art compositions due to their high efficacy against a broad spectrum of microorganisms while at the same time being comparatively nontoxic and nonirritating to animal and plant life. The antimicrobial compositions of this invention have high efficacy against a broad spectrum of microorganisms including both Gram-positive and Gram-negative bacteria, the four major classes of fungi (Ascomycetes, Basidiomycetes, Phycomycetes and *Fungi imperfecti*), algae, protozoa and viruses (naked and envelope types).

An unusual feature of the compositions used in the method of this invention is that they not only have broad antimicrobial activity, but they exhibit generally low mammalian toxicity and skin and eye irritation. When mixed in water for suitable performance in required amounts, they generally may be considered to have essentially zero levels of toxicity and skin and eye irritation.

Another advantage that accrues in the practice of this invention is that the antimicrobial compositions have low odor and taste and impart a low color to treated water. When mixed in water in concentrations far stronger than generally required for effective performance, the water has general acceptability since the compositions impart little or no taste, odor or color to the water.

Use of the compositions of this invention is also of utility since their active ingredients have specific affinity (substantivity) toward a broad range of substrates including materials such as cellulose (e.g., wood and natural fabrics), concrete and bricks. This is of particular value in reducing microorganisms in water-treating equipment since the adherence of the antimicrobial agents to various surfaces will provide some degree of permanence in preventing the growth of microorganisms in water-treating equipment, pipelines carrying water, and holding and storage devices such as pools, basins, tanks and the like. Particularly noteworthy of applications in which this invention finds utility is in the treatment of water such as recirculating cooling water, pulp and paper processing, sewage effluent control, sterilization or sanitation of drinking water, swimming pool treatment, and the general treatment of effluence and waste water to avoid environment contamination and prevent objectionable odors from being generated by bacterial and fungal processes.

The following examples illustrate the value of this invention in selected water treatment applications:

EXAMPLES

Example 1

For swimming pool use, antimicrobials serve two purposes: (1) elimination or reduction of pathogenic flora to an acceptable level, and (2) elimination or reduction of organisms that degrade the aesthetic appeal of the water, the container (pool walls and floor), and the surrounding area (diving boards, steps, safety rails and mats, etc.). Algae, nonpathogenic bacteria and fungal growths, for example, will turn clear sparkling water into turbid, slimy water.

The most common antimicrobial for pool use is free available chlorine supplied by a variety of compounds, the most widely used of which is calcium hypochlorite. This source of chlorine presents a number of complications in use, including need to maintain critically close water pH control and reaction with nitrogen-containing substances in the water to form objectionable reaction products such as chloramines which irritate the eyes of bathers. Also, a chlorine stabilizer may be needed to inhibit ultraviolet light degradation, and an algeal control agent.

The use of the compositions of this invention substantially simplifies pool treatment. This reduces the opportunity of improper maintenance and attendant health risks. Need for close pH control of the water is eliminated, sunlight stability is satisfactory, and algeal as well as bacterial control is provided. The compositions also provide satisfactory efficacy against *Alcaligenes faecalis* which, though not considered generally to be a true pathogen, is undesirable and can interfere with interpretation of total count tests for sanitary quality of the water.

Using standard microbiological antimicrobial testing techniques, the following composition was evaluated against representative organisms involved in swimming pool maintenance. Amounts are parts by weight.

| | |
|---|---|
| Oxine | 8.2 |
| Copper hydrate | 2.8 |
| DDBSA | 60.0 |
| Ethanol | 10.0 |
| Propylene glycol methyl ether | 19.0 |

| | Microbicidal Concentration (ppm) (based on Cu-8-Q |
|---|---|
| *Mycobacterium phlei* (ATCC 15610) | 10 |
| *Staphylococcus aureus* (ATCC 6538) | 10 |
| *Alcaligens faecalis* (ATCC 337) | 100 |
| *Esherichia coli* (ATCC 11229) | 1040 |
| *Klebsiella pneumoniae* (ATCC 4356) | 1040 |
| *Pseudomonas aeruginosa* (ATCC 15442) | 1040 |
| *Salmonella typhi* (ATCC 6539) | 1040 |
| *Candida albicans* (ATCC 10259) | 10 |
| *Aspergillis niger* (ATCC 9642) | 10 |

Example 2

The following composition was prepared (amounts are parts by weight):

| | |
|---|---|
| Oxine | 4.1 |
| Copper hydrate | 1.4 |
| DDBSA | 64.5 |
| Methanol | 30.0 |

The composition was tested for microorganism control in paper mill water. The water samples, with and without addition of the test composition, were subjected to a microbial count in accordance with standard mill quality control procedures.

| | % Composition in Mill Water | No. of Microbe Colonies/ml | | % Reduction |
|---|---|---|---|---|
| | | Before Aging | 1-hr. Aging | |
| Control water | 0 | 102,000 | 175,000 | — |
| Treated water | 0.09 | | 3,000 | 98.3 |
| Treated water | 0.19 | | 0 | 100.0 |

In addition to high antimicrobial efficacy, substantivity of the composition to cellulose removes much of the antimicrobial from the process water by affixation to the pulp. This serves two unique functions: (1) substantially reduces the quantity of antimicrobial that otherwise would be discharged with the paper mill effluent into the environment, and (2) provides, at no extra cost over that required to treat the water, an antifungal agent contained within the final products of the paper mill.

Example 3

To illustrate the substantivity of the compositions of this invention to cellulosic surfaces (pulp, paper and wood), the composition of the preceding example was diluted 1:500 with water and 5% green oak wood flour added and thoroughly mixed. Within five minutes, 20-30% of the active ingredients in the test composition became affixed to the wood particles as determined by testing the active ingredient concentration in the solution.

In a similar test, a 1:5 water dilution of the composition was prepared and a piece of smooth-surfaced, dry southern pine wood dipped in it for five seconds, removed and washed under running water for five seconds. A qualitative color test for copper (1% dithiooxamide in isopropanol) indicated the presence of copper on the wood surface.

This unique substantivity has utility in protection of wood cooling towers and other wooden components of recirculated water cooling systems. These wood parts are highly susceptible to fungal and bacterial degradation and to surface coatings of slime which reduces functional efficiency.

Example 4

The following composition was prepared (amounts are parts by weight):

| | |
|---|---|
| Oxine | 4.1 |
| Copper hydrate | 1.4 |
| DDBSA | 64.5 |
| Propylene glycol methyl ether | 30.0 |

A 1:400 use dilution in water was made up and 5% paper pulp admixed therewith. Analytical determination of the active ingredient retained in the solution was made after three periods of time:

| Time after Introduction of Pulp | Active Ingredient Reduction in the Solution (based on Cu-8-Q) |
|---|---|
| 3 minutes | 23% |
| 1 hour | 47% |
| 24 hours | 73% |

These results provide an indication of affinity of the cellulose pulp for the active antimicrobial ingredient.

SECTION 11

According to another embodiment of our invention we have discovered that the compositions of section 1 (hereinafter referred to as "the compositions of this invention") are useful for cleaning, sanitizing or disinfecting substrates by contacting the substrate with such compositions.

DESCRIPTION OF THE PRIOR ART

As a rule, disinfecting and sanitizing antimicrobials are included within cleaning agents only for specialty uses and the combination of antimicrobials with cleaning agents has comprised only a small portion of the over-all cleaner markets. A variety of factors have dictated against large-scale incorporation of antimicrobials into cleaning compounds for general usage because of the increased costs, various problems that arise, and limitations that are imposed upon their general use. Representative of the various problems that may be encountered in the use of antimicrobials in cleaning compounds are the taste and odor that they frequently impart to the cleaning compound; the lack of flexibility in using water and organic, polar and nonpolar carriers; the high danger of skin and eye irritation; high water resistance; poor heat and light stability; poor substantive properties which render the antimicrobials transient and readily washed away; loss of antimicrobial activity in the presence of organic matter and dirt; poor shelf life and stability; and high toxicity toward animal and plant life when the antimicrobials are used in efficacious amounts.

OBJECTS OF THE INVENTION

Accordingly, it is an object of this invention to provide methods for cleaning dirt from substrates with simultaneous sanitization, disinfection or sterilization.

Another object of this invention is to provide a composition which may be used not only to clean substrates from organic and inorganic dirt, but also to destroy or greatly reduce the population of microorgarisms on the substrate.

Another object of this invention is to prepare a composition for use in cleaning, sanitizing, disinfecting or sterilizing substrates, which compound has low odor and taste, high residual resistance to microbial activity, high resistance to loss of antimicrobial activity, high resistance to loss of antimicrobial activity in the presence of organic matter, substantivity to many substrates, inherently high cleaning properties over a wide range of substrates, high water resistance, low toxicity toward animal and plant life, low to zero skin or eye irritation, long-term shelf life and stability, and high compatibility with water and organic, polar and nonpolar carriers.

Briefly, these and other objects of this invention are achieved by treating substrates with the compositions of section 1.

DESCRIPTION OF THE INVENTION

The cleaning, sanitizing and disinfecting compositions of this invention are characterized in that they are effective for use both as cleaning agents to remove organic and inorganic dirt and as antimicrobials to kill or greatly reduce the population of microorganisms. The antimicrobial activity of these compounds has a very high per unit efficiency against a large group of microorganisms that are pathogenic to man and animals, that cause unpleasant odors, and that may cause the deterioration of a wide range of materials. The compositions of this invention are further unique in that they have a high order of safety relative both to mammals and plant life and to various substrates that are sensitive to damage from contact with acidic, alkaline or oxidizing chemicals.

The compositions of this invention also overcome the inherent limitations of many of the cleaning, sanitizing and disinfection compounds of the prior art in that they have low color, taste and odor; have a high residual resistance of antimicrobial activity; are usable in both water and organic, polar and nonpolar carriers; have low to zero skin and eye irritation characteristics; have high water resistance; have high heat and light stability; have inherently high surfactant, detergent and cleaning properties that may be modified with a large number of commercially available detergent, surfactant and wetting agents; are substantive agents to many substrates; retain significant antimicrobial activity in the presence of organic matter and dirt; have long-term shelf life and stability; and last, but by no means least, display relatively little toxicity toward animal and plant life.

The economy and safety of using the compositions of this invention, plus the range of their desirable properties, make it practical, unlike the compositions of the prior art, to incorporate antimicrobials in general cleaning compounds on a widespread basis. This upgrades and increases the utility of general cleaning compositions as, through their use, not only will dirt be removed, but control will be gained over the population and growth of microorganisms that cause disease, odors and destruction of organic materials.

The compositions of this invention are also unique in their high efficacy to cost ratio.

It may be noted that three classes of disinfectants are recognized by the federal government. They are, in order of increasing stringency of efficacy requirements:
(1) minimal claim
(2) general, and
(3) hospital type.

It is obvious that a hospital-type disinfectant should be the most desirable for all usage, but the other two classifications are made necessary as a practical concession to the economic, technical and safety problems encountered in having a single, most stringent only, category. Hence the need for a generally applicable cleaning, sanitizing, disinfecting or sterilizing compound has been compromised to accomodate present practical realities. This is not true of the compositions used in the practice of this invention since they generally avoid the limitations of products available in the marketplace and make practical and safe an antimicrobial cleaner that may be classified as a hospital-type disinfectant or disinfectant cleaner.

By way of explanation of terms, it is noted that sanitation is used to suggest a reduction in pathogenic organisms of selective genera to safe levels. The sanitization classification generally denotes a considerably lower level of antimicrobial action than products classified as disinfectants which, in turn, usually denotes a lower degree of antimicrobial activity than does sterilization. In most applications, the composition of this invention makes it practical to obtain disinfection instead of sanitization and, in some cases, even sterilization instead of sanitization or disinfection.

Cleaning agents having antimicrobial properties are generally recognized as providing superior odor control than do cleaners alone. The use of the compositions of this invention allows a broad upgrading in cleaning sanitation since a broad general improvement is achieved in odor control such as may be caused by fungal or bacterial decomposition. While control over bacterial odor is greatly improved by use of the compositions of this invention, improvement in the control of odors caused by fungi is even more significant due to the lack of presently available antifungals that are safe, cheap, practical enough from a safety standpoint for broad usage, and still efficacious against a broad spectrum of fungi. In contrast to the odor-controlling cleaning agents now available, the use of the compositions of this invention are highly effective at practical yet nontoxic levels in controlling the odors that arise, for example, in homes, farm buildings, commercial and public buildings, hospitals and institutions, animal quarters, zoos, foodstuff processing facilities, transportation equipment, fishing vessels, industrial plants and warehouses, subway facilities, mortuaries, restaurants, sewage, hospital and food-processing organic waste, recirculation water, air systems, and on through a host of other environments in which odor control may be desired.

It should be noted that in the application of the compositions of this invention to various substrates, the primary nature of the deodorant action is in the prevention and blockage of further odor generation by the destruction of microbial action and not in the destruction of existing odors.

To illustrate methods for practicing this invention and to demonstrate the use of the compositions of this invention, the following examples are given:

EXAMPLES

Example 1

The following composition was prepared (amounts given are parts by weight):

| Oxine | 4.1 |
|---|---|
| Copper hydrate | 1.4 |
| DDBSA | 64.0 |
| Propylene glycol methyl ether | 30.5 |

Thirty parts by weight of this composition were blended, at 130° F., with agitation, with:

| Laurel alcohol ethoxylate (20 EO) | 15 |
|---|---|
| Octyl phenol ethoxylate (9 EO) | 15 |
| Water, demineralized | 30 |
| Isopropanol | 10 |

This formulated concentrate was use-diluted with water. A nylon and a wool carpet, both of which were uncleaned after two years of regular service, were shampooed and placed back in use in a damp indoor location. Both came out of the shampoo operation clean and bright. Neither exhibited any bacterial- or fungal-caused odor after fourteen months in service.

Example 2

A preparation made from:

| Oxine | 2.0 parts by weight |
|---|---|
| Copper hydrate | 0.7 " |
| DDBSA | 40.0 " |
| Isopropanol | 30.0 " |
| Distilled water | 27.3 " | was diluted 1:100 with tap water, and strips of aluminum foil, lightweight cotton cloth and dry, smooth-surfaced southern yellow pine wood were dipped for three minutes therein.

Treated and untreated strips were allowed to air dry and remain exposed to the air for seven weeks. The strips then were tested by placing a *Staphylococcus aureus* culture on the test surfaces with these results:

| Sample | Average Zone of Inhibition (mm) |
|---|---|
| Untreated aluminum foil | 0 |

| Sample | Average Zone of Inhibition (mm) |
|---|---|
| Treated aluminum foil | 1.0 |
| Untreated cotton cloth | 0 |
| Treated cotton cloth | 2.5 |
| Untreated pine wood | 0 |
| Treated pine wood | 5.0 |

Examples 3–7

To demonstrate the antifungal properties of various metal-oxine chelates, compositions were prepared using 6 parts by weight of the indicated metal-oxine plus 64 parts DDBSA plus 31 parts methanol. These compositions were diluted 1:200 with a water carrier for use, and freshly cut pine boards were dip immersed in the formulation to be tested. The boards, along with an untreated control, were placed in a chamber for 28 days and maintained at a temperature of about 80° F. and a humidity of about 70%. After the test period, the specimen boards were evaluated in terms of percentage of total surface area covered by fungal stain and mold growth.

| Example | Metal-Oxine | % Fungal Growth |
|---|---|---|
| 3 | Copper | 17 |
| 4 | Tin | 20 |
| 5 | Aluminum | 28 |
| 6 | Nickel | 39 |
| 7 | Zinc | 46 |

The foregoing metal-oxines (metal-8-quinolinolates) also may be prepared in situ in the compositions by reacting oxine with any of a number of appropriate metal compounds. Although the copper chelate of oxine generally is the most effective and versatile for a broad range of end uses, other metal-oxine chelates have utility.

Example 8

The following DDBSA/Cu-8-Q solution was prepared by reacting copper hydrate and solubilizing the resulting Cu-8-Q in DDBSA and mixing in the remaining ingredients (amounts are parts by weight):

| Copper hydrate | 1.70 |
|---|---|
| Oxine | 4.44 |
| DDBSA | 64.81 |
| Methanol | 15.05 |
| Isopropanol | 14.00 |

This composition was diluted with a water carrier, as tabularized below, and tested in comparison with a sodium tetrachlorophenate (23%) liquid concentrate, also diluted in a water carrier, against organisms on three species of green lumber—Douglas fir, Amabilis fir and Ponderosa pine. The organisms were:

| *Cephaloascus fragans* | a brown mold that infects certain wood species |
|---|---|
| *Trichoderma virgatum* | a common cold |
| Mixed spores | a combination of two molds (Penicillium sp. and *Aspergillis niger*) and a fungus (*Ceratocystis pilifera*) that causes blue stain in wood. |

The freshly cut wood samples were dip treated (15-second immersion) with the test fungicides and then innoculated with spore suspensions of the above-described fungi. The test boards plus untreated control boards were then placed in a warm, humid chamber for four weeks. The results are set forth in the table below in which:

| | Use Dilution | C. fragans | | | T. virgatum | | | Mixed spores | | |
|---|---|---|---|---|---|---|---|---|---|---|
| | | A | B | C | A | B | C | A | B | C |
| Tetrachlorophenol composition | 1:100 | 4 | 4 | 4 | 0 | 0 | 3 | 3 | 4 | 4 |
| DDBSA/Cu—8-Q solution | 1:240 | 2 | 0 | 1 | 3 | 0 | 4 | 4 | 3 | 4 |
| Tetrachlorophenol composition | 1:50 | 2 | 0 | 4 | 0 | 0 | 1 | 3 | 2 | 4 |
| DDBSA/Cu—8-Q solution | 1:120 | 0 | 0 | 1 | 3 | 0 | 1 | 2 | 2 | 2 |
| Tetrachlorophenol composition | 1:25 | 2 | 2 | 3 | 0 | 0 | 1 | 0 | 0 | 3 |
| DDBSA/Cu—8-Q solution | 1:60 | 0 | 0 | 0 | 1 | 0 | 0 | 0 | 0 | 0 |
| Tetrachlorophenol composition | 1:12.5 | 0 | 1 | 0 | 0 | 0 | 0 | 0 | 0 | 2 |
| DDBSA/Cu—8-Q solution | 1:30 | 0 | 0 | 0 | 0 | 0 | 0 | 0 | 0 | 0 |
| Control (no treatment) | | 4 | 4 | 4 | 3 | 4 | 4 | 4 | 4 | 4 |

A = Douglas fir
B = Amabilis fir
C = Ponderosa pine
0 = no growth
1 = no growth for 2 weeks
2 = medium growth
3 = heavy growth in 4 weeks
4 = heavy growth in 2 weeks Example 9

The following composition was tested for minimum fungicidal concentration and compared to two well known antifungal chemicals—pentachlorophenol and 2,3,5 trichloro-4-propyl-sulfonyl pyridine—and DDBSA.

| Oxine | 8.2 parts by weight |
|---|---|
| Copper hydrate | 2.8 parts by weight |
| DDBSA | 59.0 parts by weight |
| Propylene glycol methyl ether | 30.0 parts by weight |

All of the test composition concentrations to be tested were incorporated in the fungal growth media (agar) in accordance with standard microbiological practices. Agar plugs containing the test fungicides then were inoculated with a sporulating culture and inoculated as the temperatures and times specified by The American Type Culture Collection (ATCC) recommendations. The plugs were then scored for absence or presence of organism growth. The results are shown in the following table. Minimum fungicidal concentrations were determined against a broad spectrum of fungi that are detrimental to man, foodstuffs and materials and which can result in metabolite formations (mycotoxins) of extreme toxicity to man and animals.

In the table below, Composition A is that of this Example 9 and the active ingredient is Cu-8-Q; Composition B is DDBSA; Composition C is pentachlorophenol; and Composition D is 2,3,5-trichloro-4-propylsulfonyl pyridine. Where no concentration is listed, no data is available. The stated value of "1" means 1 or fewer ppm.

|  | Minimum Fungicidal Concentration (ppm of active ingredient) | | | |
|---|---|---|---|---|
|  | A | B | C | D |
| Aspergillis niger (ATCC 9642) | 1 | 10,000 | 1-3 | — |
| Aspergillis terreus (ATCC 10609) | 1 | 100 | — | 36 |
| Aspergillis flavus (ATCC 11655) | 1 | 1,000 | 22-54 | — |
| Alternaria alternata (ATCC 13963) | 1 | — | — | — |
| Aureobasidium pullulans (ATCC 16624) | 1 | 100 | — | — |
| Lenzites trabea (ATCC 11539) | 1 | 100 | 1-3 | — |
| Polyporus tulipiferae (ATCC 11245) | 1 | 100 | 1-3 | — |
| Penicillium brevi compactum (ATCC 16024) | 1 | 100 | — | — |
| Rhizopus stolonifer (ATCC 24794) | 1 | 100 | 1-3 | — |
| Trichoderma viride (ATCC 8678) | 10 | 100 | — | — |
| Trichoderma sp. (ATCC 12668) | 1 | 100 | — | — |
| Candida albicans (ATCC 10259) | 1 | 1,000 | — | 3 |

These results illustrate the high efficacy of the composition of this invention and confirm the fact that an antifungal composition prepared from a Cu-8-Q/DDBSA solution is much superior to DDBSA alone. The results also indicate the favorable relative efficacy of the test composition compared to the two commercially available fungicides of recognized high performance.

Example 10

Test compositions were evaluated as wood preservatives via a standard soil block culture procedure (ASTM D4131-61) wherein the wood blocks were water-leached in accordance with standard technique prior to exposure to the test fungus. The test fungi were those specified for wood decay evaluation by the American Wood Preservers' Association (AWPA)—namely, Lenzites trabea (Madison 617, ATCC 11539) which is the standard test fungus for above-ground wood exposure, and Poria monticola (Madison 698, ATCC 11538) which is the standard copper-tolerant fungus for ground contact wood use.

In the table below, the results are expressed as percentage weight loss of the wood test blocks from decay fungi attack.

Composition A is comprised of:

| Oxine | 4.42 parts by weight |
|---|---|
| Copper hydrate | 1.51 parts by weight |
| DDBSA | 64.07 parts by weight |
| Methanol | 30.00 parts by weight |

The composition was diluted 1:110 in a water carrier for impregnation of the L. trabea test blocks and 1:55 for test against P. monticola.

Composition B was the same as Composition A except that it was diluted 1:55 with toluene carrier for block impregnation for test against both test fungi.

Composition C was the same as the DDBSA/Cu-8-Q solution of Example 25 diluted with a water carrier 1:220 for test against L. trabed and 1:55 against P. monticola.

Cunilate 2174 was diluted 1:110 with a toluene carrier.

The abbreviation "pcf" means pounds of Cu-8-Q per cubic foot of wood.

| Composition | Lenzites trabea | | Poria monticola | |
|---|---|---|---|---|
|  | Retention (pcf) | Weight Loss (%) | Retention (pcf) | Weight Loss (%) |
| A | 0.021 | 0.3 | 0.040 | 1.3 |
| B | 0.025 | 5.0 | 0.029 | 11.3 |
| C | 0.018 | 2.0 | 0.036 | 8.1 |
| Cunilate 2174 | 0.024 | 13.6 | 0.026 | 43.4 |
| Untreated control | 0 | 45.3 | 0 | 55.1 |

These results demonstrate the efficacy of the compositions of the invention in both a water and an organic solvent (toluene) carrier. Also illustrated is the greatly improved efficacy over Cunilate 2174, especially for wood in ground contact service. The wood protection results with Compositions A, B and C compare favorably with those of pentachlorophenol (PCP), tested simultaneously, wherein PCP, a world standard for wood preservation, exhibited 1.4% weight loss at 0.30 pcf retention against L. trabea and 3.1% weight loss at 0.27 pcf retention in the wood against P. monticola.

Employing AWPA Test Method M12-72 (revised 1973) for testing wood block resistance to termite (Reticulitermes flavipes) attack, it was determined that no attack occurred at retentions of Composition A adequate to protect the wood from decay.

Example 11

The purpose of this test was to determine antifungal efficacy of DDBSA/Cu-8-Q solutions and to compare their efficacy to that of a world standard, sodium pentachlorophenate, and a mixture of two well-known agricultural fungicides, Topsin M (a thiophenate) and Nabam (a thiocarbomate). The test method is designated as a proposal for the Finnish NWPC Standard No. 1.4.1.3/1974. The test substrate was fresh cut, green pine wood. The test fungi were:
Blue stain fungi—mixture of
  Ceratocystis pilifera Z11
  Sclerophoma entoxylina Z11
  Pullularia pullulans U2
Mold fungi—mixture of
  Paecilomyces varioti X15
  Cladosporium sphaerospermum R7
  Aspergillis amstelodami X19

In the table below, Composition A is the formulation of Example 3.

Composition B is the formulation of Example 3 except that the dilution with a water carrier was 1:100 rather than 1:200.

Composition C is a 1:5% concentration of sodium pentachlorophenate in water.

Composition D is a 0.4% concentration in water of a 47:53 weight ratio of Topsin M:Nabam.

E refers to untreated control pine boards.

The rating index is:

|  | Test Composition | | | | |
| --- | --- | --- | --- | --- | --- |
|  | A | B | C | D | E |
| Blue stain fungi growth | 0.8 | 0.3 | 0.5 | 2.5 | 3.9 |
| Mold fungi growth | 0.5 | 0 | 0.3 | 1.3 | 3.6 |

0 = no visible growth
1 = traces of growth
2 = slight growth
3 = moderate growth
4 = covered with fungi The demonstrated efficacy of Compositions A and B against the six listed fungal organisms has utility not only on the tested substrate—wood—but also for protection of a variety of other materials that are attacked by one or more of the fungi, including paint, concrete, brick, textiles and leather.

Example 12

Using the standard AOAC fungicidal test method (12th Edition, 1975), the composition below was evaluated against two widespread fungi.

| Oxine | 2.08 parts by weight |
| --- | --- |
| Copper hydrate | 0.70 parts by weight |
| DDBSA | 40.00 parts by weight |
| Isopropanol | 32.00 parts by weight |
| Demineralized water | 25.22 parts by weight |

The two fungi were *Aspergillis niger*, a ubiquitous black fungus which flourishes on a broad range of substrates, and *Trichophyton mentagrophytes*, a cause of "athlete's foot."

*A. niger*—at 1:200 use dilution in a water carrier, no growth after 10 minutes' exposure.

*T. mentagrophytes*—at 1:750 use dilution in a water carrier, no growth after 10 minutes' exposure.

Simular but somewhat lower efficacy results were obtained by substituting zinc-8-Q or aluminum-8-Q in the composition of this example, produced by reacting zinc oxide and aluminum hydroxide respectively with oxine.

Example 13

The DDBSA/Cu-8-Q solution of Example 9 was tested, along with a number of well known antimicrobial agents, agains a broad spectrum screen of economically important Gram-positive and Gram-negative bacteria. All antimicrobial agents were incorporated in the agar bacterial growth media according to standard microbiological practices. The bacterial species were grown in nutrient broth; 24-hour cultures, the inoculum, then were streaked onto the nutrient agar plates containing the test antimicrobials. After a 24-hour incubation at the appropriate temperature, the plates were rated for presence or absence of bacterial growth.

Minimum bactericidal concentrations for each of the tested agents are stated in the following tabulation of results in parts per million (ppm) of active ingredient as defined in the description of each agent.

|  | Antimicrobial Agent (ppm* of active ingredient) | | | | | | |
| --- | --- | --- | --- | --- | --- | --- | --- |
| Bacteria (ATCC No.) | A | B | C | D | E | F | G |
| Gram-positive: | | | | | | | |
| *Bacillus cereus* | 1 | 100 | — | 7 | 8 | 5-10 | — |
| *Bacillus lichenforms* (27326) | 1 | 100 | — | 7 | 8 | 2-5 | — |
| *Bacillus megaterium* (27327) | 1 | 100 | — | 7 | 8 | — | — |
| *Bacillus subtillis* (37328) | 1 | 100 | — | 750 | 8 | — | 3 |
| *Micrococcus flavus* (10240) | 1 | 100 | — | 7 | 8 | — | — |
| *Mycobacterium phlei* (15610) | 1 | 10 | — | 7 | 8 | — | 3 |
| *Staphylococcus aureus* (6538) | 1 | 100 | 2083 | 7 | 8 | 1-3 | 3 |
| Gram-negative: | | | | | | | |
| *Alcaligenes faecalis* (337) | 10 | 1000 | — | 750 | 80 | — | — |
| *Alcaligenes marshalii* (21030) | 104 | 100 | — | 7 | 8 | — | — |
| *Esherichia coli* (11229) | 104 | 10,000 | — | 750 | 80 | 250-500 | 165 |
| *Flavobacterium arboresceus* (4358) | 10 | 10 | 4166 | 7 | 8 | — | — |
| *Klebsiella pneumoniae* (4356) | 10 | 10,000 | — | 750 | 8 | — | — |
| *Proteus vulgaris* | 10 | 1000 | — | 750 | 800 | — | — |
| *Pseodomonas aeruginosa* (15442) | 104 | 1000 | 4166 | 750 | 800 | 1000-2500 | 165 |
| *Salmonella cholerasuis* (10708) | 104 | 1000 | — | 750 | 80 | 250-500 | 165 |
| *Salmonella typhi* (6539) | 104 | 1000 | 2083 | 750 | 80 | — | 165 | stated value of "1" means 1 or less
A = the DDBSA/Cu—8-Q solution of Example 9 with the active ingredient expressed in terms of Cu—8-Q.
B = DDBSA.
C = phenol
D = Betadine, an iodine/polyvinylpyrrolidone complex containing 0.75% iodine. The active ingredient is iodine.
E = Alkyl dimethyl ammonium chlorides (61% $C_{12}$, 23% $C_{14}$, 11% $C_{16}$ and 3% $C_{10}$).
F = sodium pentachlorophenate
G = 2,3,5-trichloro-4-propylsulfonyl pyridine.
See page 170 for list of antimicrobial agents These data demonstrate the high efficacy of the composition of Example 9. On the basis of the average of the efficacies against all the test organisms, Composition A is 45 times superior to Composition B; 88 times better than Composition C; 10.7 times better than Composition D; and 3.5 times superior to Composition E.

On the basis of the average of the efficacies against the three test bacteria (*Staphylococcus aureus, Salmonella cholerasuis* and *Pseudomonas aeruginosa* PRD-10) required by the Environmental Protection Agency of a "hospital grade" disinfectant, Composition A is 10 times better than Composition B; 7.2 times better than Composition D; and 1.6 times better than Composition E.

Example 14

The composition set forth below was prepared by previously described procedures:

| Oxine | 2.08 parts by weight |
|---|---|
| Copper hydrate | 0.70 parts by weight |
| Isopropanol | 32.00 parts by weight |
| DDBSA | 40.00 parts by weight |
| Water (demineralized) | 25.22 parts by weight |

When evaluated as a bactericide by the AOAC Use Dilution Method (12th Edition, 1975), 10 ring carriers per organism, the following results were obtained (A=subculture and B=resubculture):

| | Use Dilution in Water Carrier | Negative A | Negative B | Positive A | Positive B |
|---|---|---|---|---|---|
| *Staphylococcus aureus* | 1:1000 | 10 | 10 | 0 | 0 |
| *Salmonella cholerasuis* (PRD-10) | 1:1000 | 10 | 10 | 0 | 0 |
| *Pseudomonas aeruginosa* | 1:400 | 10 | 10 | 0 | 0 |
| *Aerobacter aerogenes* | 1:400 | 10 | 10 | 0 | 0 |

A ten-minute kill is required against the first three pathogens for sale as a hospital-grade disinfectant. Efficacy against the fourth organism, a major cause of slime in recirculated cooling water systems and pulp and paper mills, demonstrates utility of the composition as a slimicide.

Example 15

This composition was prepared and tested at one use dilution, 1:50 in water carrier, against the causal agent of potato ring rot bacteria (*Corynebacterium sepedonicum*):

| Oxine | 2.08 parts by weight |
|---|---|
| Copper hydrate | 0.70 parts by weight |
| DDBSA | 40.00 parts by weight |
| Triton X-100 | 20.00 parts by weight |
| Isopropanol | 22.00 parts by weight |
| Water (demineralized) | 15.22 parts by weight |

Infected potato seed readily contaminate potato seed cutters, sacks, bins, cellars, trucks and planting equipment with the highly infectious ring rot bacteria. The result may be infected potato plants, tubers and reduced yields.

The test procedure consisted of dipping unpainted, planed wood laths (6") into a slurry of infected ring rot tuber tissue, allowing excess slurry to drain off (3-5 minutes) and then spraying the contaminated lath with the test antibacterials. Three to five minutes later, healthy Norgold Russet potato seed pieces were rubbed vigorously against both sides of the contaminated and antibacterial-treated laths. The process was repeated using laths not contaminated with *C. sepedonicum* but treated with the test antibacterial agent. The rubbed seed pieces were stored in bags and later planted at the appropriate time.

In addition to the composition of the invention, untreated controls, 20% Clorox (1.05% sodium hypochlorite in water), formaldehyde (37% formalin diluted 1:120 in water) and Roccal (benzalkonium chloride or zephiran chloride) diluted with water to 800 ppm concentration were tested. The results of the test are tabulated below and refer to plants and tubers produced from the tubbed test seed pieces.

| Antimicrobial | Ring Rot Contaminated | % Plant Stored | % Ring Rot Plants | % Ring Rot Tubers | Yield cwt/acre |
|---|---|---|---|---|---|
| None (control) | Yes | 98 | 23 | 8 | 493 |
| None (control) | No | 95 | 0 | 0 | 609 |
| DDBSA/Cu—8-Q | Yes | 98 | 0 | 2 | 631 |
| DDBSA/Cu—8-Q | No | 100 | 0 | 0 | 602 |
| 20% Clorox | Yes | 98 | 20 | 9 | 500 |
| 20% Clorox | No | 98 | 0 | 0 | 602 |
| Roccal | Yes | 98 | 20 | 9 | 515 |
| Roccal | No | 98 | 0 | 0 | 638 |

The composition of this example demonstrates superior control of the ring rot bacterium. Other species of the genus Corynebacterium are causal agents of disease in man and a variety of plant life.

The above examples illustrates the basic high order inhibition characteristics of the disclosed compositions against a range of odor-producing fungi and bacteria.

We claim:

1. An antimicrobial composition for controlling bacterial and fungi comprising in combination:
   (a) a metal chelate of 8-hydroxy quinoline in which the metal is selected from the group consisting of copper, mercury, cadmium, nickel, tin, aluminum and zinc,
   (b) an alkyl benzene sulfonic acid wherein the alkyl group is $C_6$ to $C_{18}$, said metal chelate being solubilized by said sulfonic acid,
   (c) the weight ratio of said metal chelate to said alkyl benzene sulfonic acid being between about 1:5 and 1:14.

2. A composition according to claim 1 wherein the composition includes 1-50 parts by weight of a polar diluent.

3. A composition according to claim 2 wherein said polar diluent is methanol, ethanol, isopropanol, n-butanol, dimethylformamide, N-methyl-2-pyrrolidone, ethylene glycol or water.

4. A composition according to claim 1 wherein said metal chelate is copper-8-quinolinolate.

5. A composition according to claim 2 wherein said metal chelate is copper-8-quinolinolate.

6. A composition according to claim 1 wherein said sulfonic acid is dodecylbenzene sulfonic acid.

7. A composition according to claim 2 wherein said sulfonic acid is dodecylbenzene sulfonic acid.

8. A composition according to claim 3 wherein said sulfonic acid is dodecylbenzene sulfonic acid.

9. A composition according to claim 4 wherein said sulfonic acid is dodecylbenzene sulfonic acid.

10. A method for controlling the growth of microorganisms which comprises applying to the locus of said microorganisms an antimicrobially effective amount of a composition comprising:
    (a) a metal chelate of 8-hydroxy quinoline in which the metal is selected from the group consisting of copper, mercury, cadmium, nickel, tin, aluminum and zinc,
    (b) an alkyl benzene sulfonic acid wherein the alkyl group is $C_6$ to $C_{18}$, said metal chelate being solubilized by said sulfonic acid,
    (c) the weight ratio of said metal chelate to said sulfonic acid being between about 1:5 and 1:14.

11. A method according to claim 10 wherein said composition includes 1-50 parts by weight of a polar diluent.

12. A method according to claim 11 wherein said polar diluent is methanol, ethanol, isopropanol, n-butanol, dimethylformamide, N-methyl-2-pyrrolidone, ethylene glycol or water.

13. A method according to claim 10 wherein said metal chelate is copper-8-quinolinolate.

14. A method according to claim 11 wherein said metal chelate is copper-8-quinolinolate.

15. A method according to claim 12 wherein said metal chelate is copper-8-quinolinolate.

16. A method according to claim 10 wherein said sulfonic acid is dodecylbenzene sulfonic acid.

17. A method according to claim 11 wherein said sulfonic acid is dodecylbenzene sulfonic acid.

18. A method according to claim 12 wherein said sulfonic acid is dodecylbenzene sulfonic acid.

19. A method according to claim 13 wherein said sulfonic acid is dodecylbenzene sulfonic acid.

* * * * *